United States Patent [19]
Stork et al.

[11] Patent Number: 5,998,188
[45] Date of Patent: Dec. 7, 1999

[54] MITOGEN ACTIVATED PROTEIN KINASE PHOSPHATASE CDNAS AND THEIR BIOLOGICALLY ACTIVE EXPRESSION PRODUCTS

[75] Inventors: Philip J. S. Stork; Anita Misra-Press, both of Portland, Oreg.

[73] Assignee: Oregon Health Sciences University, Portland, Oreg.

[21] Appl. No.: 08/990,379

[22] Filed: Dec. 15, 1997

Related U.S. Application Data

[63] Continuation of application No. PCT/US96/10402, Jun. 14, 1996
[60] Provisional application No. 60/000,263, Jun. 16, 1995.
[51] Int. Cl.$^6$ .................................................. C12N 9/16
[52] U.S. Cl. ............................................................ 435/196
[58] Field of Search .................................. 435/196, 320.1

[56] References Cited

U.S. PATENT DOCUMENTS 5,512,434  4/1996  Aaronson et al. ........................ 435/6

FOREIGN PATENT DOCUMENTS

| 9307250 | 4/1993 | United Kingdom . |
| 9402573 | 2/1994 | United Kingdom . |
| WO 94/23039 | 10/1994 | WIPO . |
| WO 95/21923 | 8/1995 | WIPO . |

OTHER PUBLICATIONS

Pagés, G., et al., "Mitogen–activated protein kinases p42$^{mapk}$ and p44$^{mpak}$ are required for fibroblast proliferation," *Proc. Natl. Acad. Sci. U.S.A.* 90:8319–8323 (1993).
Blenis, J., "Signal Transduction via the MAP kinases: Proceed at your own Risk," *Proc. Natl. Acad. Sci. U.S.A.* 90:5889–5892 (1993).
Cowley, S. et al., "Activation of MAP Kinase Kinase Is Necessary and Sufficient for PC12 Differentiation and for Transformation of NIH 3T3 Cells," *Cell* 77:841–852 (1994).
Chao, M.V., "Growth Factor Signaling: Where Is The Specificity," *Cell* 68:995–997 (1992).
Nguyen, T.T. et al., "Co–regulation of the Mitogen–activated Protein Kinase, Extracellular Signal–Regulated Kinase 1, and the 90–kDa Ribosomal S6 Kinase in PC12 Cells," *Biol. Chem.* 268:9803–9810 (1993).
Wood, K.W. et al., "ras Mediates Nerve Growth Factor Receptor Modulation of Three Signal–Transducing Protein Kinases: MAP Kinase, Raf–1, and RSK," *Cell* 68:1041–1050 (1992).
Alema, S. et al., "Differentiation of PC12 phaeochromocytoma cells induced by v–src oncogene," *Nature* 316:557–559 (1985).
Thomas, S.M. et al., "Ras Is Essential for Nerve Growth Factor–and Phorbol Ester–Induced Tyrosine Phosphorylation of MAP Kinases," *Cell* 68:1031–1040 (1992).
Thomas, S.M. et al., "Induction of Neurite Outgrowth by v–src Mimics Critical Aspects of Nerve Growth Factor–Induced Differentiation," *Mol. Cell. Biol.* 11:4739–4750 (1991).

Lloyd, E.D. et al., "$pp42/44$MAP Kinase Is a Component of the Neurogenic Pathway Utilized by Nerve Growth Factor in PC12 Cells," *J. Neurochem.* 59:1099–1109 (1992).
Crews, C.M. et al., "Extracellular Signals and Reversible Protein Phosphorylation: What to Mek of It All," *Cell* 74:215–217 (1993).
Zheng, C.–F. et al., "Protein of MEKs, the Kinases That Phosphorylate and Activate the Extracellular Signal–regulated Kinases," *J. Biol. Chem.* 268:23933–23939 (1993).
Sun, H. et al., "MKP–1 (3CH134), an Immediate Early Gene Product, Is A Dual Specificity Phosphatase That Dephosphorylates MAP Kinase In Vivo," *Cell* 75:487–493 (1993).
Alessi, D.R. et al., "The human CL100 gene encodes a Tyr/Thr–protein phosphatase which potently and specifically inactivates MAP kinase and suppresses its activation by oncogenic ras in Xenopus oocyte extracts," *Oncogene* 8:2015–2020 (1993).
Ward, Y. et al., "Control of MAP kinase activation by the mitogen–induced threonine/tyrosine phosphatase PAC1," *Nature* 367:651–654 (1994).
Zheng, C.–F. et al., "Dephosphorylation and Inactivation of the Mitogen–activated Protein Kinase by a Mitogen–induced Thr/Tyr Protein Phosphatase," *J. Biol. Chem.* 268:16116–16119 (1993).
Traverse, S. et al., "Sustained activation of the mitogen–activated protein (MAP) kinase cascade made by required for differentiation of PC12 cells," *Biochem. J.* 288:351–355 (1992).
Kumagai, A. et al., "Regulation of the cdc25 Protein during the Cell Cycle in Xenopus Extracts," *Cell* 70:139–151 (1992).
Charles, C.H. et al., "cDNA sequence of a growth factor–inducible immediate early gene and characterization of its encoded protein," *Oncogene* 7:187–190 (1992).
Doi, K. et al., "MSG5, a novel protein phosphatase promotes adaptation to pheromone response in *S. cerevisiae*," *EMBO J.* 13:61–70 (1994).
Guan, K. et al., "Cloning and expression of a protein–tyrosine–phosphatase," *Proc. Natl. Acad. Sci. U.S.A.* 87:1501–1505 (1990).
Keyse, S.M. et al., "Oxidative stress and heat shock induce a human gene encoding a protein–tyrosine phosphatase," *Nature* 359:644–647 (1992).
Rohan, P.J. et al., "PAC–1: A Mitogen–Induced Nuclear Protein Tyrosine Phosphatase," *Science* 259:1763–1766 (1993).
Ishibashi, T. et al., "A Novel Dual Specificity Phosphatase Induced By Serum Stimulation and Heat Shock," *J. Biol. Chem.* 269:29897–29902 (1994).

(List continued on next page.)

*Primary Examiner*—Robert A. Wax
*Assistant Examiner*—Bradley S. Mayhew
*Attorney, Agent, or Firm*—Harness, Dickey & Pierce, P.L.C.

[57] ABSTRACT

The invention relates to a novel mitogen-activated protein kinase phosphatase, MKP-2. The invention further relates to methods and means for preparing and to nucleic acids encoding this protein. The MKP-2 of the present invention is useful in the control of cell growth, differentiation and apoptosis.

3 Claims, 24 Drawing Sheets

OTHER PUBLICATIONS

Sun, H. et al., "Inhibition of Ras–Induced DNA Synthesis by Expression of the Phosphatase MKP–1," *Science* 266:285–288 (1994).

Noguchi, T. et al., "Structure, Mapping, and Expression of erp, a Growth FActor–Inducible Gene Encoding a Nontransmembrane Protein Tyrosine Phosphatase, and Effect of ERP on Cell Growth," *Mol. Cell. Biol.* 13:5195–5205 (1993).

Boulton, T.G. et al., "ERKs: A Family of Protein–Serine/Tyreonine Kinases That Are Activated and Tyrosine Phosphorylated in Response to Insulin and NGF," *Cell* 65:663–675 (1991).

Thomas, K.R. et al., "Swaying Is a Mutant Allele of the Proto–Oncogene Wnt–1," *Cell* 67:969–976 (1991).

Druker, B. et al., "Tyrosine Phophorylation of rasGAP and Associated Proteins in Chronic Myelogenous Leukemia Cell Lines," *Blood* 79:2215–2220 (1992).

Sanger, F. et al., "DNA sequencing with chain–terminating inhibitors," *Proc. Natl. Acad. Sci. U.S.A.* 74:5463–5467 (1977).

Misra–Press, A. et al., "Complex Alternative Splicing Partially Inactivates the Human Chorionic Somatomammoropin–like (hCS–L) Gene," *J. Biol. Chem.* 269:23220–23229 (1994).

Arriza, J.L. et al., "The Neuronal Mineralocorticoid Receptor as a Mediator of Glucocorticoid Response," *Neuron* 1:887–900 (1988).

Bruder, J.T. et al., "Serum–, TPA–, and Ras–induced expression from Ap–1/Ets–driven promoters requires Raf1 kinase," *Genes & Develop.* 6:545–556 (1992).

Howley, P.M. et al., "Eukaryotic Cloning Vectors Derived from Bovine Papillomavirus DNA," *Methods Enzymol.* 101:387–402 (1983).

Luehrsen, K.R. et al., "Transient Expression Analysis in Plants Using Firefly Luciferase Reporter Gene," *Methods Enzymol.* 216:397–414 (1992).

Bradford, M.M., "A Rapid and Sensitive Method for the Quantitation of Microgram Quantities of Protein Utilizing the Principle of Protein–Dye Binding," *Anal. Biochem.* 72:248–254 (1976).

Bialojan, C. et al., "Inhibitory effect of a marine–sponge toxin, okadaic acid, on protein phosphatases," *Biochem J.* 256:283–290 (1988).

MacKintosh, C. et al., "Cyanobacterial microcystin–LR is a potent and specific inhibitor of protein phosphatases 1 and 2A from both mammals and higher plants," *FEBS Lett.* 264:187–192 (1990).

Marais, R. et al., "The SRF Accessory Protein Elk–1 Contains a Growth Factor–Regulated Transcriptional Activation Domain," *Cell* 73:381–393 (1993).

Kwak, S.P. et al., "Isolation and Chracterization of a Human Dual Specificity Protein–Tyrosine Phosphatase Gene," *J. Biol. Chem.* 269:3596–3604 (1994).

Shaw, G. et al., "A Conserved AU Sequence from the 3' Untranslated Region of GM–CSF mRNA Mediates Selective mRNA Degradation," *Cell* 46:659–667 (1986).

Fiore, R.S. et al., "p42 Mitogen–Activated Protein Kinase In Brain: Prominent Localization In Neuronal Cell Bodies And Dendrites," *Neurosci.* 55:463–472 (1993).

Boulton, T.G. et al., "ERKs: A Family Of Protein–Serine/Threomine Kinases That Are Activated And Tyrosine Phosphorylated In Response To Insulin And NGF," *Cell* 65:663–675 (1991).

Bading, H. et al., "Stimulation of Protein Tyrosine Phosphorylation by NMDA Receptor Activation," *Science* 253:912–914 (1991).

Friedman, L.K. et al., "Kainate–induced Status Epilepticus Alters Glutamate and $GABA_A$ Receptor Gene Expression in Adult Rat Hippocampus: An in situ Hybridization Study," *J. Neurosci.* 14:2697–2707 (1994).

Pennypacker, K.R. et al., "Kainate–Induced Changes in Opioid Peptide Genes and AP–1 Protein Expression in the Rat Hippocampus," *J. Neurochem.* 60:204–211 (1993).

Dérijard, B. et al., "JNK1: A Protein Kinase Stimulated by UV Light and Ha–Ras That Binds and Phosphorylates the c–Jun Activation Domain," *Cell* 76:1025–1037 (1994).

Loeb, D.M. et al., "A Trk Nerve Growth Factor (NGF) Receptor Point Mutation Affecting Interaction with Phospholipase C–τ1 Abolishes NFG–promoted Peripherin Induction but Not Neurite Outgrowth," *J. Biol. Chem.* 269:8901–8910 (1994).

Young, S.W. et al., "Differentiation of PC12 cells in response to a cAMP analogue is accompanied by sustained activation of mitogen–activated protein kinase," *FEBS Lett.* 338:212–216 (1994).

Wu, J. et al., "Rapid deactivation of MAP kinase in PC12 cells occurs independently of induction of phosphatase MKP–1," *FEBS Lett.* 353:9–12 (1994).

Brondello, J.M. et al., "Constitutive MAP kinase phosphatase (MKP–1) expression blocks G1 specific gene transcription and S–phase entry in fibroblasts," *Oncogene* 10:1895–1904 (1995).

Chu, Y. et al., "The Mitogen–activated Protein Kinase Phosphatases PAC1, MKP–1, and MKP–2 Have Unique Substrate Specificities and Reduced Activity in Vivo toward the ERK2 sevenmaker Mutation," *J. Biol. Chem.* 271(11):6497–6501 (1996).

Cowley, S. et al., "Activation of MAP Kinase Kinase Is Necessary and Sufficient for PC12 Differentiation and for Transformation of NIH 3T3 Cells," *Cell* 77:841–852 (1994).

Fillmore, H.L. et al., "Differentiation of PC12 Cells With Nerve Growth Factor Is Associated With Induction of Transin Synthesis and Release," *J. Neurosci Res.* 31:662–669 (1992).

Fukuda, M. et al., "Induction of neurite outgrowth by MAP kinase in PC12 cells," *Oncogene* 11:239–244 (1995).

Hill, C.S. et al., "Transcriptional Regulation by Extracellular Signals: Mechanisms and Specificity," *Cell* 80:199–211 (1995).

Jaiswal, R.K. et al., "Identification and Characterization of a Nerve Growth Factor–stimulated Mitogen–Activated Protein Kinase Activator in PC12 Cells," *J. Biol. Chem.* 268:7055–7063 (1993).

Janknecht, R. et al., "Activation of ternary complex factor Elk–1 by MAP kinases," *EMBO J.* 12:5097–5104 (1993).

Liu, Y. et al., "Role of Mitogen–activated Protein Kinase Phosphatase during the Cellular Response to Genotoxic Stress," *J. Biol. Chem.* 270:8377–8380 (1995).

Marshall, C.J., "Specificity of Receptor Tyrosine Kinase Signaling: Transient versus Sustained Extracellular Signal–Regulated Kinase Activation," *Cell* 80:179–185 (1995).

Minden, A. et al., "c–Jun N–Terminal Phosphorylation Correlates with Activation of the JNK Subgroup but Not the ERK Subgroup of Mitogen–Activated Protein Kinases," *Mol. Cell. Biol.* 14:6683–6688 (1994).

Qui, M.–S. et al., "NGF and EGF Rapidly Activate $p21^{ras}$ in PC12 Cells by Distinct, Convergent Pathways Involving Tyrosine Phosphorylation," *Neuron* 7:937–946 (1991).

Misra–Press, A. et al., "A Novel Mitogen–activated Protein Kinase Phosphatase," *J. Biol. Chem.* 270:14587–14596 (1995).

Roberson, M.S. et al., "A Role for Mitogen–Activated Protein Kinase in Mediating Activation of the Glycoprotein Hormone α–Subunit Promoter by Gonadotropin–Releasing Hormone," *Mol. Cell Biol.* 17:3531–3539 (1995).

Rosen, L.B. et al., "Membrane depolarization and Calcium Influx Stimulate MEK and MAP Kinase via Activation of Ras," *Neuron* 12:1207–1221 (1994).

Whitmarsh, A.J. et al., "Integration of MAP Kinase Signal Transduction Pathways at the Serum Response Element," *Science* 269:403–407 (1995).

Yao, H. et al., "Cyclic Adenosine Monophosphate Can Convert Epidermal Growth Factor into a Differentiating Factor in Neuronal Cells," *J. Biol. Chem.* 270:20748–20753 (1995).

Kyriakis, J.M. et al., "The stress–activated protein kinase subfamily of c–Jun kinases," *Nature* 369:156–160 (1994).

Sluss, H.K. et al., "Signal Transduction by Tumor Necrosis Factor Mediated by JNK Protein Kinases," *Mol. Cell. Biol.* 14:8376–8384 (1994).

Cano, E. et al., "Parallel signal processing among mammalian MAPKs," *TIBS* 20:117–122 (1995).

Yao, R. et al., "Requirement for Phosphatidylinositol–3 Kinase in the Prevention of Apoptosis by Nerve Growth Factor," *Science* 267:2003–2007 (1995).

Milne, D.M. et al., "p53 is Phosphorylated in Vitro and in Vivo by an Ultraviolet Radiation–induced Protein Kinase Characteristic of the c–Jun Kinase, JNK1," *J. Biol. Chem.* 270:5511–5518 (1995).

Liu, Y. et al., "Role of Mitogen–Activated Protein Kinase Phosphatase during the Cellular Response to Genotoxic Stress," *J. Biol. Chem.* 270:8377–8380 (1995).

Minden, A. et al., "Differential Activation of ERK and JNK Mitogen–Activated Protein Kinases by Raf–1 and MEKK," *Science* 266:1719–1723 (1994).

Kallunki, T. et al., "JNK2 contains a specificity–determining region responsible for efficient c–Jun binding and phosphorylation," *Genes & Dev.* 8:2996–3007 (1994).

Thompson, C.B., "Apoptosis in the Pathogenesis and Treatment of Disease," *Science* 267:1456–1462 (1995).

Kharbanda, S. et al., "Ionizing Radiation Stimulates a Grb2–mediated Association of the Stress–Activated Protein Kinase with Phosphatidylinositol 3–Kinase," *J. Biol. Chem.* 270:18871–18874 (1995).

Kerr, J.F.R. et al., "Apoptosis: Its Significance in Cancer and Cancer Therapy," *Cancer* 73:2013–2026 (1994).

Duff, J.L. et al., "Angiotensin II Induces 3CH134, a Protein–tyrosine Phosphatase, in Vascular Smooth Muscle Cells," *Journal of Biological Chemistry* 268:26037–26040 (1993).

Guan, Kun–Liang et al., "Isolation and Characterization of a Novel Dual Specific Phosphatase, HVH2, Which Selectively Dephosphorylates the Mitogen–Activated Protein Kinase," *J. Biol. Chem.* 270(13):7197–7203 (1995).

Charles, C.H. et al., "The growth factor–inducible immediate–early gene 3CH134 encodes a protein–tyrosine–phosphatase," *PNAS (USA)* 90:5292–5296 (1993).

King, A.G. et al., "Isolation and characterisation of a uniquely regulated threonine, tyrosine phosphatase (TYP 1) which inactivates ERK2 and $p54^{jnk}$," *Oncogene* 11:2553–2563 (1995).

(-377) cggccggctgctgcagctccggcggcagtggggaaaacggcggtgctaagctggagcagcagcctagcagaacctagcaaaacacaccagggc
acaaaccgagaggagccctctctcgtaaacatactccctcctgctccactctcggttcactcgcgtccgtgcgcctgcttggcgccagagaagg
ctcggactgctatgtaacgtcgaggctgcgggaggaggaaggggtgttgggaagagccttgggccaagtttgcggtcacttcggcagcc
gccttcttagccttccctgttccttcttgccttgtcccttgtcttcccggctccgtcctgtcctgtgcttgccggcgac         60

ATG GTG ACG ATG GAG ATG GAC CTG CGG GAG CAG TGC AGC GTG CTC AAA AGG CTG ATG AAC        60
MET Val Thr Met Glu Met Asp Leu Arg Glu Gln Cys Ser Val Leu Lys Arg Leu Met Asn         20

CGA GAT GAG AAC GGC ACG GGC GCG GGC AGC GGC CAC AGC GCC CTG GGC CTG AGC GGC             129
Arg Asp Glu Asn Gly Thr Gly Ala Gly Ser Gly His Ser Ala Leu Gly Leu Ser Gly              43

GGC AAG TGC TTG CTG CTG GAC TGC AGG CCG TTT CTG GCT CAC AGC GCG GGC TAC ATC CGA GGC TCG GTG    198
Gly Lys Cys Leu Leu Leu Asp Cys Arg Pro Phe Leu Ala His Ser Ala Gly Tyr Ile Arg Gly Ser Val    66

AAC GTG CGC TGC AAT ACC ATC GTG CGG AGG CGG AAG GCC TCC GTG AGC CTG GAG CAG ATT CTG CCC        267
Asn Val Arg Cys Asn Thr Ile Val Arg Arg Arg Lys Ala Ser Val Ser Leu Glu Gln Ile Leu Pro        89

GCC GAG GAA GAG GTG CGC CCC TGC GCT CTG GCC TCT ACT CGG TCA TCG TCT ACG CAG CCC GAG            336
Ala Glu Glu Glu Val Arg Pro Cys Ala Leu Ala Ser Thr Arg Ser Ser Ser Thr Met Thr Gln Pro Glu    112

GCG CGC CGA GAG TCT CCG GGA CAC CAG GGT GCT CGT GGT GCA GCG TTG CGC CGG AAC GCG GAG            405
Ala Arg Arg Glu Ser Pro Gly His Gln Gly Ala Arg Gly Ala Ala Leu Arg Arg Asn Ala Glu            135

CGC ACA GAC ATC TGC CTG CTT AAA GGT GGC TAT GAG AGG TTT TCT TCT GAG TAC CCA GAA TTC TGC TCT    474
Arg Thr Asp Ile Cys Leu Leu Lys Gly Gly Tyr Glu Arg Phe Ser Ser Glu Tyr Pro Glu Phe Cys Ser    158

AAA ACT AAG GCC GCC CTG GCC GCC ATC GCC ATA CCA GTA CCT CCC AGC ACA AAT GAG TCC TTG GAT CTG GGC 543
Lys Thr Lys Ala Ala Leu Ala Ala Ile Ala Ile Pro Pro Val Pro Pro Ser Thr Asn Glu Ser Leu Asp Leu Gly 181

TGC AGC TCC TGT GGG ACC CCA CTG CAC GAC CAG GGG GGT CCT GTG GAG ATC CTT CCT TTC CTC TAC CTC    612
Cys Ser Ser Cys Gly Thr Pro Leu His Asp Gln Gly Gly Pro Val Glu Ile Leu Pro Phe Leu Tyr Leu    204

GGC AGT GCC TAC CAC GCT GCC CGC AGG GAC ATG GAC CTT GAT GCC CTG GGG ATC ACG CTA CTG AAT GTC    681
Gly Ser Ala Tyr His Ala Ala Arg Arg Asp Met Asp Leu Asp Ala Leu Gly Ile Thr Leu Leu Asn Val    227

FIGURE 1B

```
TCC TCA GAC TGC CCC AAT CAC TTT GAG GGA CAT TAC CAG TAC AAG TGC ATC CCG GTA GAA GAT AAC CAC    750
Ser Ser Asp Cys Pro Asn His Phe Glu Gly His Tyr Gln Tyr Lys Cys Ile Pro Val Glu Asp Asn His    250

AAG GCT GAC ATC AGC TCC TGG TTC ATG GAA TAC ATA GAC GCA GTG AAG GAC TGC CGA GGG    819
Lys Ala Asp Ile Ser Ser Trp Phe Met Glu Tyr Ile Asp Ala Val Lys Asp Cys Arg Gly    273

CGA GTG CTG GTT CAC TGC CAG GCC ATC TCT AGA TCA GCC ATC TGC CTG GCC TAC CTG ATG    888
Arg Val Leu Val His Cys Gln Ala Ile Ser Arg Ser Ala Ile Cys Leu Ala Tyr Leu Met Met    296

AAG CGG GTG AGG CTG GAG GAG GCT TTC GTC AAG CAG CGC ATC ATC TCG CCC AAC    957
Lys Arg Val Arg Leu Glu Glu Ala Phe Val Lys Gln Arg Ile Ile Ser Pro Asn    319

TTC AGC TTC ATG GGC CAG TTG CTG CAG TTC GAG TCT CAG GTG CTC ACC TGC GCA GCG GAG GCC    1026
Phe Ser Phe Met Gly Gln Leu Leu Gln Phe Glu Ser Gln Val Leu Thr Cys Ala Ala Glu Ala    342

GCC AGC CCT TCC GTG CCC CTG CGG GAG AGG GGG AAG GCC ACT CCC ACC TCG CAG TTC GTC TTC    1095
Ala Ser Pro Ser Gly Pro Leu Arg Glu Arg Gly Lys Ala Thr Pro Thr Ser Gln Phe Val Phe    365

AGC TTC CCC GTG TCC GTG GGT GTG CAC GCG GCT CCC AGT AAC CTG CCG TAC CTG CAC AGC CCC ATC ACC    1164
Ser Phe Pro Val Ser Val Gly Val His Ala Ala Pro Ser Asn Leu Pro Tyr Leu His Ser Pro Ile Thr    388

ACC TCC CCC AGC TGT TAG    1182
Thr Ser Pro Ser Cys Stop.    393 gactagtcacggacaccgagtcggccagagtcggccagagtcggcccatgccagtccacatgtgaggagcgaatagggactgaccagtggggaccagg
tgaccgtcccatccattctcctggccgaccacaggccagcaggatgcaatacctatgacttgatatgctccgttcttccccttgcaggtagaattacctca
acaccacagctagagcaataagagcagcttccgcctgcagagaagacttggatttgtcgtcctgccaaatgtgccaccagttttattgatgggagag
ttattattattatttttttaaagcaatcaagctttgccagaaagtgcctggttct......(~3kb).......atcattcaaggacttcagaagataacaatg
ggaggaggagaaagttgagttgtgtaaatagcccccgtctttctgagtgtgtcattctacattgatatgctcgtattctgtaggttgtacctgtttc
aatacttgtaactgtgtgtaaatagcccccgtctttctgagtgtgtcattctacattgatatgctcgtattctgtaggttgtacctgtttc
tagaagagtcaaacagtctgtttattattattgcttgaaaaagatcattgaagaaaataaatacattttcaccattaaaaaaaa    (~4800)
```

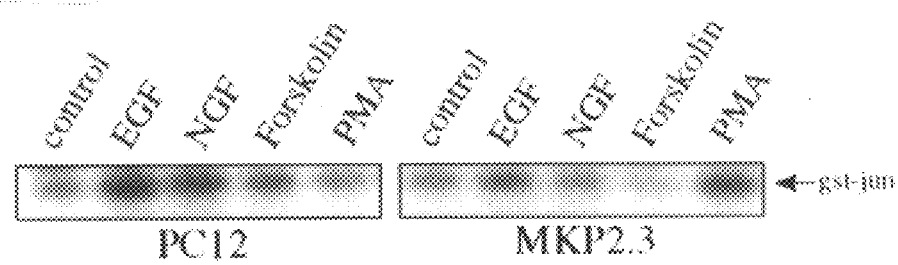
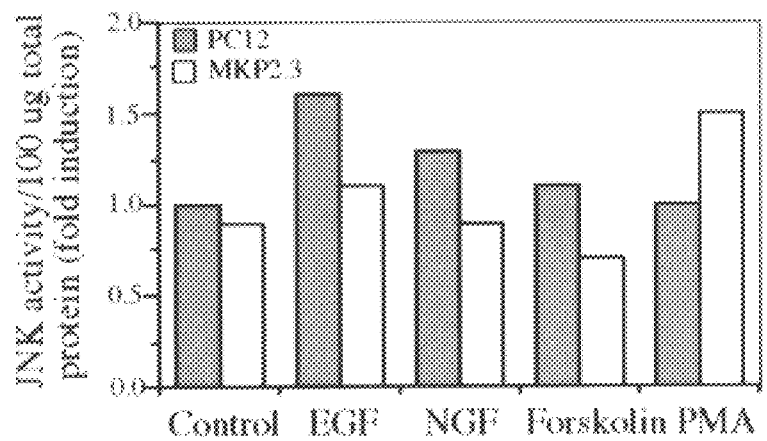
FIG. 14A.
FIG. 14B.
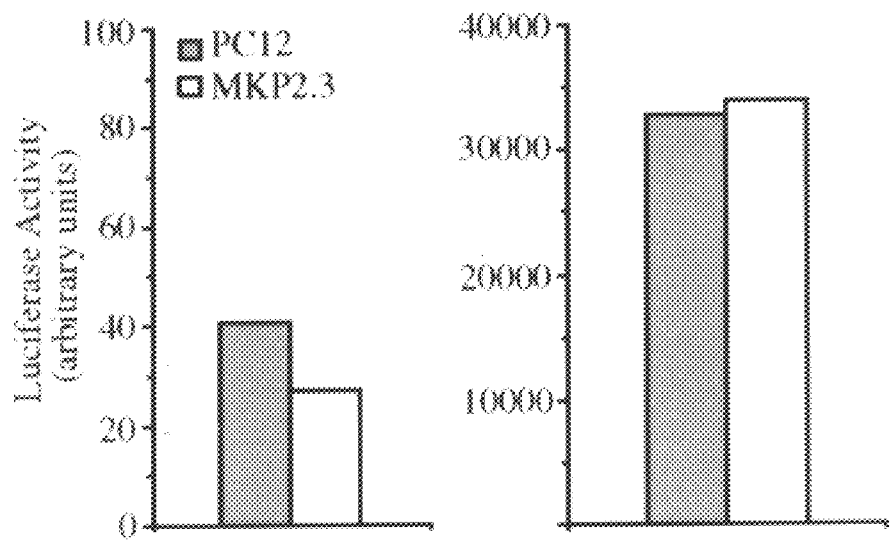

FIGURE 22

```
(-377) cggccggctgctgcagctccggcggcggcagttggggaaaacggcggtgcctaaggctggagcagctgcctagctagcaaacaccaggggc
       aacaaacgagaggagccctctctcgtaaacatactccctcctcgtcacttgctcccggtgtgccgtgccgcctctttgccgccagagaagg
       ctcggactgctatgtaacgtcgaggctgcggaggaggaagggtgttgggagaagcctggggcaagtttgcgggtcacttcggcagcc
       gccttcttagcctcgcctgttcctcttgtagcctgctggcttggctgccctgtcttctccgctcttctccccagctgctgttgccggcgac
```

|                                                                                                                                  |     |     |
|----------------------------------------------------------------------------------------------------------------------------------|-----|-----|
| ATG GTG ACG ATG GAG GAA CTG CGG GAG ATG GAC TGC AGC GTG CTC AAA AGG CTG ATG AAC                                                  | 60  |     |
| MET Val Thr Met Glu Glu Leu Arg Glu Met Asp Cys Ser Val Leu Lys Arg Leu Met Asn                                                  | 20  |     |
| CGA GAT GAG AAC GGC GGC ACG GCG AGC AGC GGC CTG GGG CTG CTG AGC GGC                                                              | 129 |     |
| Arg Asp Glu Asn Gly Gly Thr Ala Ser Ser Gly Gly Ala Leu Gly Leu Leu Ser Gly                                                      | 43  |     |
| GGC AAG TGC TTG CTG CTG GAC TGC AGG CCG TTT CTG GCT CAC AGC GCG GGC TAC ATC CGA GGC TCG GTG                                      | 198 |     |
| Gly Lys Cys Leu Leu Leu Asp Cys Arg Pro Phe Leu Ala His Ser Ala Gly Tyr Ile Arg Gly Ser Val                                      | 66  |     |
| AAC GTG CGC TGC AAT ACC ATC GTG CGG CGG AGG GCC AAG GGC TCC GTG AGC CTG GAG CAG ATT CTG CCC                                      | 267 |     |
| Asn Val Arg Cys Asn Thr Ile Val Arg Arg Arg Ala Lys Gly Ser Val Ser Leu Glu Gln Ile Leu Pro                                      | 89  |     |
| GCC GAG GAA GAG GTG CGC GCC CGC CTG CGC TCT GGC CTC TAC TCG GCT GTC ATC GTC TAC GAT GAG CGC AGC CCG                              |     |     |
| Ala Glu Glu Glu Val Arg Ala Arg Leu Arg Ser Gly Leu Tyr Ser Ala Val Iso Val Tyr Asp Glu Arg Ser Pro                              |     |     |
| CGC GCC GAG AGT CTC CGG GAG GAC AGC GAG ACA GTG TCG         CTG GTC GTG CAG GCG TTG CGC CGG AAC GCG GAG                         |     |     |
| Arg Ala Glu Ser Leu Arg Glu Asp Ser Glu Thr Val Ser              Leu Val Val Gln Ala Leu Arg Arg Asn Ala Glu                    |     |     |
| CGC ACA GAC ATC TGC CTG CTT AAA GGT GGC TAT GAG AGG TTT TCT TCT GAG TAC CCA GAA TTC TGC TCT                                      |     |     |
| Arg Thr Asp Ile Cys Leu Leu Lys Gly Gly Tyr Glu Arg Phe Ser Ser Glu Tyr Pro Glu Phe Cys Ser                                      |     |     |
| AAA ACT AAG GCC CTG GCC GCC ATC CCA CCT CCC GTA CCC AGC ACA AAT GAG TCC TTG GAT CTG GGC                                          |     |     |
| Lys Thr Lys Ala Leu Ala Ala Ile Pro Pro Pro Val Pro Ser Thr Asn Glu Ser Leu Asp Leu Gly                                          |     |     |
| TGC AGC TCC TGT GGG ACC CCA CTG CAC CTG CAC CAG GGT CCT GTG GGA GAT CTT CCT TTC CTC TAC CTC                                      |     |     |
| Cys Ser Ser Cys Gly Thr Pro Leu His Asp Gln Gly Pro Val Gly Ile Leu Leu Pro Phe Leu Tyr Leu                                      |     |     |
| GGG AGT GCC TAC CAC GCT GCC CGC CGC AGG GAC ATG CTT GAT GCC CTG GGG ATC ACG GCT CTA CTG AAT GTC                                  |     |     |
| Gly Ser Ala Tyr His Ala Ala Arg Arg Asp Met Leu Asp Ala Leu Gly Ile Thr Ala Leu Leu Asn Val                                      |     |     |

FIGURE 22 cont.

```
TCC TCA GAC TGC CCC AAT CAC TTT GAG GGA CAT TAC CAG TAC AAG TGC ATC CCG GTA GAA GAT AAC CAC
Ser Ser Asp Cys Pro Asn His Phe Glu Gly His Tyr Gln Tyr Lys Cys Ile Pro Val Glu Asp Asn His

AAG GCT GAC ATC AGC TCC TGG TTC ATG GAA GCC ATC GAA TAC ATA GAC GCA GTG AAG GAC TGC CGA GGG
Lys Ala Asp Ile Ser Ser Trp Phe Met Glu Ala Ile Glu Tyr Ile Asp Ala Val Lys Asp Cys Arg Gly

CGA GTG CTG GTT CAC TGC GGC CAG GCC ATC TCT AGA TCA GCC ACC ATC TGC CTG TAC CTG ATG ATG
Arg Val Leu Val His Cys Gln Ala Gly Ile Ser Arg Ser Ala Thr Ile Cys Leu Tyr Leu Met Met

AAG CGG GTG AGG CTG GAG GAG GCT TTC GAG TTC GTC AAG CAG CGC CGT AGC ATC ATC TCG CCC AAC
Lys Arg Val Arg Leu Glu Glu Ala Phe Glu Phe Val Lys Gln Arg Arg Ser Ile Ile Ser Pro Asn

TTC AGC TTC ATG GGC CAG TTG CTG CAG TCT CAG GTG CTC ACC ACG TCC TGC GCA GGG GAG GCC
Phe Ser Phe Met Gly Gln Leu Leu Gln Ser Gln Val Leu Thr Thr Ser Cys Ala Ala Glu Ala

GCC AGC CCT TCC GGG CCC CTG CGG GAG AGG GGG AAG GCC ACT CCC ACC TCG CAG TTC GTC TTC
Ala Ser Pro Ser Gly Pro Leu Arg Glu Arg Gly Lys Ala Thr Pro Thr Ser Gln Phe Val Phe

AGC TTC CCC GTG TCC GTG GGT GTG CAC GCG GCT CCC AGT AAC CTG CCG TAC CTG CAC AGC CCC ATC ACC
Ser Phe Pro Val Ser Val Gly Val His Ala Ala Pro Ser Asn Leu Pro Tyr Leu His Ser Pro Ile Thr

ACC TCC CCC AGC TGT TAG
Thr Ser Pro Ser Cys Stop.
```

```
gactagtcacgggacaccgagtccagagtcggccgacaccgagtccagagtcggcccagagtcggcccatgccagtgtgcaagtgtgcaagtccacatgtgaggagcgaatagga gactgaccagtgggggaccagg
tgaccgtcccatccattctcctggccgccacagggccagctagagtgccaggccagctgcaataactgactctagagtgcaataactgactgacttgaatacacacatttaaaacaaacacagcta
aacacccacagcctagagcaataagagacagcttccgcctgcagagaagactggagaagacttccgcctgcagagaagactggatttgtgtccgtttttccttgcagtagaaatttacctca
ttattattattatttttttaaagcaatcaagcttgaaagttatgaagccacagatcctgcaaatgtgccaaccagttttattgagtggagag
ggaggaggagaaagttgagtttgccagaaaagtgcctggttct......(~3kb).......atcattcaaggacttcagaagataacaatg
aatacttgtaacgtgtgtaaatagcccccgtcttctgagtgctgctcatttctacattgatatgctcgtattctgtaggttgtacctgttctc
tagaagagtcaaacagtctgtttttatttgcttgaaaaaagatcattgaagaaaataaatacattttcaccatttaaaaaaaa   (~4800)
```

FIGURE 23

SEQUENCE LISTING

<160> NUMBER OF SEQ ID NOS: 19

<210> SEQ ID NO 1
<211> LENGTH: 1987
<212> TYPE: DNA
<213> ORGANISM: Rattus norvegicus

<400> SEQUENCE: 1

```
cggccggctg ctgcagctcc ggcggcagtt gggggaaaac ggcggtgcct aaggctggag      60
cagcctagct agcaaaacac accagggggca acaaaccgag aggagccctc tctctcgtaa    120
acatactccc ctcctcggtc acttgctccg ggtgccgtgc gcgcctgctt tggcgccaga    180
gaaggctcgg actgctatgt aacgtcgagg ctgcgggagg aggaggaagg ggtgttggga    240
gaagagcctt ggggccaagt ttgcgggtca cttcggcagg cgccttctta gccttcgcct    300
gttccttctt gtagcctagc tggcttgggt gcccttggtc ttctccggct ccccagctgc    360
```

```
tgtgctttgc cggcgacatg gtgacgatgg aggaactgcg ggagatggac tgcagcgtgc    420
tcaaaaggct gatgaaccga gatgagaacg gcggcacggc gggcagcagc ggcggcagcc    480
acggcgccct gggctgctg agcggcggca agtgcttgct gctggactgc aggccgtttc     540
tggctcacag cgcgggctac atccgaggct cggtgaacgt gcgctgcaat accatcgtgc    600 ggcgagggc caaggctcc gtgagcctgg agcagattct gcccgccgag gaagaggtgc      660 gccctgcgc tctggcctct actcggctgt catcgtctac gatgacgcag cccgcgcgcc     720
gagagtctcc gggaggacag cacagtgtcg ctggtcgtgc agcgttgcgc cggaacgcgg    780
agcgcacaga catctgcctg cttaaaggtg gctatgagag gttttcttct gagtacccag    840
aattctgctc taaaactaag gccctggccg ccatcccacc ccccgtacct cccagcacaa    900
atgagtcctt ggatctgggc tgcagctcct gtgggacccc actgcacgac caggggggtc    960
ctgtggagat ccttccttc ctctacctcg gcagtgccta ccacgctgcc cgcagggaca   1020
tgcttgatgc cctggggatc acggctctac tgaatgtctc ctcagactgc cccaatcact   1080
ttgagggaca ttaccagtac aagtgcatcc cggtagaaga taaccacaag gctgacatca   1140
gctcctggtt catggaagcc atcgaataca tagacgcagt gaaggactgc cgagggcgag   1200
tgctggttca ctgccaggcc ggcatctcta gatcagccac catctgcctg gcctacctga   1260
tgatgaagaa acgggtgagg ctggaggagg ctttcgagtt cgtcaagcag cgccgtagca   1320
tcatctcgcc caacttcagc ttcatgggcc agttgctgca gttcgagtct caggtgctca   1380
ccacgtcctg cgcagcggag gccgccagcc cttccgggcc cctgcgggag aggggggaagg   1440 ccactcccac ccccacctcg cagttcgtct tcagcttccc cgtgtccgtg ggtgtgcacg   1500
cggctcccag taacctgccg tacctgcaca gccccatcac cacctcccc agctgttagg    1560 actagtcacg ggacaccgag tccagagtcg gccccatgcc agtgtgcaag tccacatgtg   1620
aggagcgaat agggactgac cagtggggga ccaggtgacc gtccccatcc atttctcctt   1680
ggccgaccac agggccagct aggatggcaa taactatgac tttgaataca catttaaaac   1740
aaacacagct aaacacccac agcctagagc aataagagca gcttccgcct gcagagaaga   1800
cttggatttt gtgtccgttt ttcctttgca ggtagaaatt tacctcatta ttattattat   1860
tattttttaa agcaatcaag cttgaaagtt atgaagccca cagatcctgg caaatgtgcc   1920 aaccagttt attgagtgga gagggaagga ggagaaagtt gagtttgcca gaaaagtgcc    1980
tggttct                                                           1987
```

<210> SEQ ID NO 2
<211> LENGTH: 1993
<212> TYPE: DNA
<213> ORGANISM: Rattus norvegicus

<400> SEQUENCE: 2

```
cggccggctg ctgcagctcc ggcggcagtt gggggaaaac ggcggtgcct aaggctggag     60
cagcctagct agcaaaacac accaggggca acaaaccgag aggagccctc tctctcgtaa    120
acatactccc ctcctcggtc acttgctccg ggtgccgtgc gcgcctgctt tggcgccaga    180
gaaggctcgg actgctatgt aacgtcgagg ctgcggagg aggaggaagg ggtgttggga    240
gaagagcctt ggggccaagt ttgcgggtca cttcggcagg cgccttctta gccttcgcct    300
gttccttctt gtagcctagc tggcttgggt gcccttggtc ttctccggct ccccagctgc    360
tgtgctttgc cggcgacatg gtgacgatgg aggaactgcg ggagatggac tgcagcgtgc    420
tcaaaaggct gatgaaccga gatgagaacg gcggcacggc gggcagcagc ggcggcagcc    480
```

```
acggcgccct ggggctgctg agcggcggca agtgcttgct gctggactgc aggccgtttc    540
tggctcacag cgcgggctac atccgaggct cggtgaacgt gcgctgcaat accatcgtgc    600
ggcggagggc caagggctcc gtgagcctgg agcagattct gcccgccgag gaagaggtgc    660
gcgcccgcct gcgctctggc ctctactcgg ctgtcatcgt ctacgatgag cgcagcccgc    720
gcgccgagag tctccgggag gacagcacag tgtcgctggt cgtgcaggcg ttgcgccgga    780
acgcggagcg cacagacatc tgcctgctta aggtggcta tgagaggttt tcttctgagt    840
acccagaatt ctgctctaaa actaaggccc tggccgccat cccaccccc gtacctccca    900 gcacaaatga gtccttggat ctgggctgca gctcctgtgg accccactg cacgaccagg     960 ggggtcctgt ggagatcctt cctttcctct acctcggcag tgcctaccac gctgcccgca   1020
gggacatgct tgatgccctg gggatcacgg ctctactgaa tgtctcctca gactgcccca   1080
atcactttga gggacattac cagtacaagt gcatcccggt agaagataac cacaaggctg   1140
acatcagctc ctggttcatg gaagccatcg aatacataga cgcagtgaag gactgccgag   1200
ggcgagtgct ggttcactgc caggccgca tctctagatc agccaccatc tgcctggcct    1260
acctgatgat gaagaaacgg gtgaggctgg aggaggcttt cgagttcgtc aagcagcgcc   1320
gtagcatcat ctcgcccaac ttcagcttca tgggccagtt gctgcagttc gagtctcagg   1380
tgctcaccac gtcctgcgca gcggaggccg ccagcccttc cgggcccctg cgggagaggg   1440
ggaaggccac tcccaccccc acctcgcagt tcgtcttcag cttccccgtg tccgtgggtg   1500
tgcacgcggc tcccagtaac ctgccgtacc tgcacagccc catcaccacc tcccccagct   1560
gttaggacta gtcacgggac accgagtcca gagtcggccc catgccagtg tgcaagtcca   1620
catgtgagga gcgaataggg actgaccagt ggggaccag gtgaccgtcc ccatccattt    1680
ctccttggcc gaccagggg ccagctagga tggcaataac tatgactttg aatacacatt   1740
taaaacaaac acagctaaac acccacagcc tagagcaata agagcagctt ccgcctgcag    1800
agaagacttg gattttgtgt ccgttttttcc tttgcaggta gaaatttacc tcattattat   1860
tattattatt ttttaaagca atcaagcttg aaagttatga agcccacaga tcctggcaaa    1920
tgtgccaacc agttttattg agtggagagg gaaggaggag aaagttgagt ttgccagaaa   1980
agtgcctggt tct                                                       1993

<210> SEQ ID NO 3
<211> LENGTH: 210
<212> TYPE: DNA
<213> ORGANISM: Rattus norvegicus

<400> SEQUENCE: 3
atcattcaag ggacttcaga agataacaa tgaatacttg taacgtgtgt aaatagcccc      60 cgtcttctg agtgctgtca tttctacatt tgatatgctc gtatttctgt aggttgtacc     120
ttgttttcta gaagagtcaa acagtctgtt tttttgcttg aaaaaagatc attgaagaaa    180
aataaataca ttttcaccat taaaaaaaaa                                     210

<210> SEQ ID NO 4
<211> LENGTH: 393
<212> TYPE: PRT
<213> ORGANISM: Rattus norvegicus

<400> SEQUENCE: 4

Met Val Thr Met Glu Glu Leu Arg Glu Met Asp Cys Ser Val Leu Lys
 1               5                  10                  15
```

```
Arg Leu Met Asn Arg Asp Glu Asn Gly Gly Thr Ala Gly Ser Ser Gly
            20                  25                  30

Gly Ser His Gly Ala Leu Gly Leu Leu Ser Gly Gly Lys Cys Leu Leu
        35                  40                  45

Leu Asp Cys Arg Pro Phe Leu Ala His Ser Ala Gly Tyr Ile Arg Gly
    50                  55                  60

Ser Val Asn Val Arg Cys Asn Thr Ile Val Arg Arg Ala Lys Gly
65                  70                  75                  80

Ser Val Ser Leu Glu Gln Ile Leu Pro Ala Glu Glu Val Arg Pro
                85                  90                  95

Cys Ala Leu Ala Ser Thr Arg Leu Ser Ser Thr Met Thr Gln Pro
                100                 105                 110

Ala Arg Arg Glu Ser Pro Gly Gly Gln His Ser Val Ala Gly Arg Ala
            115                 120                 125

Ala Leu Arg Arg Asn Ala Glu Arg Thr Asp Ile Cys Leu Leu Lys Gly
        130                 135                 140

Gly Tyr Glu Arg Phe Ser Ser Glu Tyr Pro Glu Phe Cys Ser Lys Thr
145                 150                 155                 160

Lys Ala Leu Ala Ala Ile Pro Pro Val Pro Pro Ser Thr Asn Glu
                165                 170                 175

Ser Leu Asp Leu Gly Cys Ser Ser Cys Gly Thr Pro Leu His Asp Gln
            180                 185                 190

Gly Gly Pro Val Glu Ile Leu Pro Phe Leu Tyr Leu Gly Ser Ala Tyr
        195                 200                 205

His Ala Ala Arg Arg Asp Met Leu Asp Ala Leu Gly Ile Thr Ala Leu
    210                 215                 220

Leu Asn Val Ser Ser Asp Cys Pro Asn His Phe Glu Gly His Tyr Gln
225                 230                 235                 240

Tyr Lys Cys Ile Pro Val Glu Asp Asn His Lys Ala Asp Ile Ser Ser
                245                 250                 255

Trp Phe Met Glu Ala Ile Glu Tyr Ile Asp Ala Val Lys Asp Cys Arg
            260                 265                 270

Gly Arg Val Leu Val His Cys Gln Ala Gly Ile Ser Arg Ser Ala Thr
        275                 280                 285

Ile Cys Leu Ala Tyr Leu Met Met Lys Lys Arg Val Arg Leu Glu Glu
290                 295                 300

Ala Phe Glu Phe Val Lys Gln Arg Arg Ser Ile Ile Ser Pro Asn Phe
305                 310                 315                 320

Ser Phe Met Gly Gln Leu Leu Gln Phe Glu Ser Gln Val Leu Thr Thr
                325                 330                 335

Ser Cys Ala Ala Glu Ala Ala Ser Pro Ser Gly Pro Leu Arg Glu Arg
            340                 345                 350

Gly Lys Ala Thr Pro Thr Pro Thr Ser Gln Phe Val Phe Ser Phe Pro
        355                 360                 365

Val Ser Val Gly Val His Ala Ala Pro Ser Asn Leu Pro Tyr Leu His
    370                 375                 380

Ser Pro Ile Thr Thr Ser Pro Ser Cys
385                 390

<210> SEQ ID NO 5
<211> LENGTH: 395
<212> TYPE: PRT
<213> ORGANISM: Rattus norvegicus

<400> SEQUENCE: 5
```

Met Val Thr Met Glu Glu Leu Arg Glu Met Asp Cys Ser Val Leu Lys
1               5                   10                  15

Arg Leu Met Asn Arg Asp Glu Asn Gly Gly Thr Ala Gly Ser Ser Gly
            20                  25                  30

Gly Ser His Gly Ala Leu Gly Leu Ser Gly Gly Lys Cys Leu Leu
        35                  40                  45

Leu Asp Cys Arg Pro Phe Leu Ala His Ser Ala Gly Tyr Ile Arg Gly
    50                  55                  60

Ser Val Asn Val Arg Cys Asn Thr Ile Val Arg Arg Ala Lys Gly
65                  70                  75                  80

Ser Val Ser Leu Glu Gln Ile Leu Pro Ala Glu Glu Val Arg Ala
                85                  90                  95

Arg Leu Arg Ser Gly Leu Tyr Ser Ala Val Ile Val Tyr Asp Glu Arg
            100                 105                 110

Ser Pro Arg Ala Glu Ser Leu Arg Glu Asp Ser Thr Val Ser Leu Val
    115                 120                 125

Val Gln Ala Leu Arg Arg Asn Ala Glu Arg Thr Asp Ile Cys Leu Leu
    130                 135                 140

Lys Gly Gly Tyr Glu Arg Phe Ser Ser Glu Tyr Pro Glu Phe Cys Ser
145                 150                 155                 160

Lys Thr Lys Ala Leu Ala Ala Ile Pro Pro Val Pro Pro Ser Thr
            165                 170                 175

Asn Glu Ser Leu Asp Leu Gly Cys Ser Ser Cys Gly Thr Pro Leu His
            180                 185                 190

Asp Gln Gly Gly Pro Val Glu Ile Leu Pro Phe Leu Tyr Leu Gly Ser
    195                 200                 205

Ala Tyr His Ala Ala Arg Arg Asp Met Leu Asp Ala Leu Gly Ile Thr
    210                 215                 220

Ala Leu Leu Asn Val Ser Ser Asp Cys Pro Asn His Phe Glu Gly His
225                 230                 235                 240

Tyr Gln Tyr Lys Cys Ile Pro Val Glu Asp Asn His Lys Ala Asp Ile
            245                 250                 255

Ser Ser Trp Phe Met Glu Ala Ile Glu Tyr Ile Asp Ala Val Lys Asp
            260                 265                 270

Cys Arg Gly Arg Val Leu Val His Cys Gln Ala Gly Ile Ser Arg Ser
    275                 280                 285

Ala Thr Ile Cys Leu Ala Tyr Leu Met Met Lys Lys Arg Val Arg Leu
    290                 295                 300

Glu Glu Ala Phe Glu Phe Val Lys Gln Arg Arg Ser Ile Ile Ser Pro
305                 310                 315                 320

Asn Phe Ser Phe Met Gly Gln Leu Leu Gln Phe Glu Ser Gln Val Leu
            325                 330                 335

Thr Thr Ser Cys Ala Ala Glu Ala Ala Ser Pro Ser Gly Pro Leu Arg
            340                 345                 350

Glu Arg Gly Lys Ala Thr Pro Thr Pro Thr Ser Gln Phe Val Phe Ser
            355                 360                 365

Phe Pro Val Ser Val Gly Val His Ala Ala Pro Ser Asn Leu Pro Tyr
    370                 375                 380

Leu His Ser Pro Ile Thr Thr Ser Pro Ser Cys
385                 390                 395

<210> SEQ ID NO 6
<211> LENGTH: 367
<212> TYPE: PRT
<213> ORGANISM: Mus sp.

<400> SEQUENCE: 6

```
Met Val Met Glu Val Gly Ile Leu Asp Ala Gly Gly Leu Arg Ala Leu
 1               5                  10                  15

Leu Arg Glu Gly Ala Ala Gln Cys Leu Leu Asp Cys Arg Ser Phe
             20                  25                  30

Phe Ala Phe Asn Ala Gly His Ile Ala Gly Ser Val Asn Val Arg Phe
         35                  40                  45

Ser Thr Ile Val Arg Arg Ala Lys Gly Ala Met Gly Leu Glu His
     50                  55                  60

Ile Val Pro Asn Ala Glu Leu Arg Gly Arg Leu Leu Ala Gly Ala Tyr
 65                  70                  75                  80

His Ala Val Val Leu Leu Asp Glu Arg Ser Ala Ser Leu Asp Gly Ala
                 85                  90                  95

Lys Arg Asp Gly Thr Leu Ala Leu Ala Ala Gly Ala Leu Cys Arg Glu
                100                 105                 110

Ala Arg Ser Thr Gln Val Phe Phe Leu Gln Gly Gly Tyr Glu Ala Phe
            115                 120                 125

Ser Ala Ser Cys Pro Glu Leu Cys Ser Lys Gln Ser Thr Pro Thr Gly
130                 135                 140

Leu Ser Leu Pro Leu Ser Thr Ser Val Pro Asp Ser Ala Glu Ser Gly
145                 150                 155                 160

Cys Ser Ser Cys Ser Thr Pro Leu Tyr Asp Gln Gly Pro Val Glu
                165                 170                 175

Ile Leu Ser Phe Leu Tyr Leu Gly Ser Ala Tyr His Ala Ser Arg Lys
                180                 185                 190

Asp Met Leu Asp Ala Leu Gly Ile Thr Ala Leu Ile Asn Val Ser Ala
            195                 200                 205

Asn Cys Pro Asn His Phe Glu Gly His Tyr Gln Tyr Lys Ser Ile Pro
        210                 215                 220

Val Glu Asp Asn His Lys Ala Asp Ile Ser Ser Trp Phe Asn Glu Ala
225                 230                 235                 240

Ile Asp Phe Ile Asp Ser Ile Lys Asp Ala Gly Gly Arg Val Phe Val
                245                 250                 255

His Cys Gln Ala Gly Ile Ser Arg Ser Ala Thr Ile Cys Leu Ala Tyr
            260                 265                 270

Leu Met Arg Thr Asn Arg Val Lys Leu Asp Glu Ala Phe Glu Phe Val
        275                 280                 285

Lys Gln Arg Arg Ser Ile Ile Ser Pro Asn Phe Ser Phe Met Gly Gln
    290                 295                 300

Leu Leu Gln Phe Glu Ser Gln Val Leu Ala Pro His Cys Ser Ala Glu
305                 310                 315                 320

Ala Gly Ser Pro Ala Met Ala Val Leu Asp Arg Gly Thr Ser Thr Thr
                325                 330                 335

Thr Val Phe Asn Phe Pro Val Ser Ile Pro Val His Pro Thr Asn Ser
            340                 345                 350

Ala Leu Asn Tyr Leu Lys Ser Pro Ile Thr Thr Ser Pro Ser Cys
        355                 360                 365
```

<210> SEQ ID NO 7
<211> LENGTH: 313
<212> TYPE: PRT
<213> ORGANISM: Mus sp.

<400> SEQUENCE: 7

-continued

```
Met Gly Leu Glu Thr Ala Cys Glu Leu Glu Cys Ala Ala Leu Gly Ala
  1               5                  10                  15

Leu Leu Arg Glu Pro Arg Glu Ala Glu Arg Thr Leu Leu Leu Asp Cys
             20                  25                  30

Arg Pro Phe Leu Ala Phe Cys Arg Ser His Val Arg Ala Ala Arg Pro
             35                  40                  45

Val Pro Trp Asn Ala Leu Leu Arg Arg Arg Ala Pro Gly Thr Pro Ala
 50                  55                  60

Ala Ala Leu Ala Cys Leu Leu Pro Asp Arg Ala Leu Arg Ala Arg Leu
 65                  70                  75                  80

Gly Arg Gly Glu Leu Ala Arg Ala Val Val Leu Asp Glu Ser Ser Ala
                 85                  90                  95

Ser Val Thr Glu Leu Pro Pro Asp Gly Pro Ala His Leu Leu Leu Ala
                100                 105                 110

Ala Leu Gln His Glu Met Arg Gly Gly Pro Thr Val Cys Phe Leu Arg
                115                 120                 125

Gly Gly Phe Lys Ser Phe Gln Thr Tyr Cys Pro Asp Leu Cys Ser Glu
130                 135                 140

Ala Pro Ala Gln Ala Leu Pro Pro Ala Gly Ala Glu Asn Ser Asn Ser
145                 150                 155                 160

Asp Pro Arg Val Pro Ile Tyr Asp Gln Gly Gly Pro Val Glu Ile Leu
                165                 170                 175

Pro Tyr Leu Tyr Leu Gly Ser Cys Asn His Ser Ser Asp Leu Gln Gly
                180                 185                 190

Leu Gln Ala Cys Gly Ile Thr Ala Val Leu Asn Val Ser Ala Ser Cys
            195                 200                 205

Pro Asn His Phe Glu Gly Leu Phe His Tyr Lys Ser Ile Pro Val Glu
            210                 215                 220

Asp Asn Gln Met Val Glu Ile Ser Ala Trp Phe Gln Glu Ala Ile Ser
225                 230                 235                 240

Phe Ile Asp Ser Val Lys Asn Ser Gly Gly Arg Val Leu Val His Cys
                245                 250                 255

Gln Ala Gly Ile Ser Arg Ser Ala Thr Ile Cys Leu Ala Tyr Leu Ile
            260                 265                 270

Gln Ser His Arg Val Arg Leu Asp Glu Ala Phe Asp Phe Val Lys Gln
            275                 280                 285

Arg Arg Gly Val Ile Ser Pro Asn Phe Ser Phe Met Gly Gln Leu Leu
290                 295                 300

Gln Leu Glu Thr Gln Val Leu Cys His
305                 310
```

<210> SEQ ID NO 8
<211> LENGTH: 397
<212> TYPE: PRT
<213> ORGANISM: Homo sapiens

<400> SEQUENCE: 8

```
Met Lys Val Thr Ser Leu Asp Gly Gly His Val Arg Lys Met Leu Arg
  1               5                  10                  15

Lys Glu Ala Ala Ala Arg Cys Val Val Leu Asp Cys Arg Pro Tyr Leu
             20                  25                  30

Ala Phe Ala Ala Ser Asn Val Arg Gly Ser Leu Asn Val Asn Leu Asn
             35                  40                  45

Ser Val Val Leu Arg Arg Ala Arg Gly Gly Ala Val Ser Ala Arg Tyr
 50                  55                  60
```

-continued

```
Val Leu Pro Asp Glu Ala Arg Ala Arg Leu Leu Gln Glu Gly Gly
 65                  70                  75                  80

Gly Gly Val Ala Ala Val Val Leu Asp Gln Gly Ser Arg His Trp
                 85                  90                  95

Gln Lys Leu Arg Glu Glu Ser Ala Phe Val Val Leu Thr Ser Leu Leu
            100                 105                 110

Ala Cys Leu Pro Ala Gly Pro Arg Val Tyr Phe Leu Lys Gly Gly Tyr
            115                 120                 125

Glu Thr Phe Tyr Ser Glu Tyr Pro Glu Cys Cys Val Asp Val Lys Pro
130                 135                 140

Ile Ser Gln Glu Lys Ile Glu Ser Glu Arg Ala Leu Ile Ser Gln Cys
145                 150                 155                 160

Gly Lys Pro Val Val Asn Val Ser Tyr Arg Pro Ala Tyr Asp Gln Gly
                165                 170                 175

Gly Pro Val Glu Ile Leu Pro Phe Leu Tyr Leu Gly Ser Ala Tyr His
            180                 185                 190

Ala Ser Lys Cys Glu Phe Leu Ala Asn Leu His Ile Thr Ala Leu Leu
            195                 200                 205

Asn Val Ser Arg Arg Thr Ser Glu Ala Cys Met Thr His Leu His Tyr
210                 215                 220

Lys Trp Ile Pro Val Glu Asp Ser His Thr Ala Asp Ile Ser Ser His
225                 230                 235                 240

Phe Gln Glu Ala Ile Asp Phe Ile Asp Cys Val Arg Glu Lys Gly Gly
                245                 250                 255

Lys Val Leu Val His Cys Glu Ala Gly Ile Ser Arg Ser Pro Thr Ile
            260                 265                 270

Cys Met Ala Tyr Leu Met Lys Thr Lys Gln Phe Arg Leu Lys Glu Ala
            275                 280                 285

Phe Asp Tyr Ile Lys Gln Arg Arg Ser Met Val Ser Pro Asn Phe Gly
290                 295                 300

Phe Met Gly Gln Leu Leu Gln Tyr Glu Ser Glu Ile Leu Pro Ser Thr
305                 310                 315                 320

Pro Asn Pro Gln Pro Pro Ser Cys Gln Gly Glu Ala Ala Gly Ser Ser
                325                 330                 335

Leu Ile Gly His Leu Gln Thr Leu Ser Pro Asp Met Gln Gly Ala Tyr
            340                 345                 350

Cys Thr Phe Pro Ala Ser Val Leu Ala Arg Cys Leu Pro Thr Gln Gln
            355                 360                 365

Ser Gln Ser Ser Ala Glu Ala Leu Trp Gln Arg Pro Asn Pro Ala Lys
370                 375                 380

Thr Gly Met Glu Glu Ser Ala Gln Pro Gln Glu Gln Leu
385                 390                 395

<210> SEQ ID NO 9
<211> LENGTH: 6
<212> TYPE: PRT
<213> ORGANISM: Mus sp.

<400> SEQUENCE: 9

Trp Phe Asn Glu Ala Ile
  1               5

<210> SEQ ID NO 10
<211> LENGTH: 17
<212> TYPE: DNA
<213> ORGANISM: Artificial Sequence
<220> FEATURE:
```

-continued

```
<223> OTHER INFORMATION: Description of Artificial Sequence:Degenerate
      primer sequence for amino acid sequence WFNEAI

<400> SEQUENCE: 10
tggttyaayg argcnat                                                    17

<210> SEQ ID NO 11
<211> LENGTH: 6
<212> TYPE: PRT
<213> ORGANISM: Mus sp.

<400> SEQUENCE: 11

Asn Phe Ser Phe Met Gly
 1               5

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:Degenerate
      primer sequence to NFSFMG

<400> SEQUENCE: 12
ccatraansw raartt                                                     16

<210> SEQ ID NO 13
<211> LENGTH: 6
<212> TYPE: PRT
<213> ORGANISM: Rattus norvegicus

<400> SEQUENCE: 13

Tyr Asp Gln Gly Gly Pro
 1               5

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:Degenerate
      primer sequence to YDQGGP

<400> SEQUENCE: 14
taygaycarg gnggncc                                                    17

<210> SEQ ID NO 15
<211> LENGTH: 6
<212> TYPE: PRT
<213> ORGANISM: Rattus norvegicus

<400> SEQUENCE: 15

Met Lys Lys Arg Val Arg
 1               5

<210> SEQ ID NO 16
<211> LENGTH: 18
<212> TYPE: DNA
<213> ORGANISM: Rattus norvegicus

<400> SEQUENCE: 16
atgaagaaac gggtgcgg                                                   18

<210> SEQ ID NO 17
<211> LENGTH: 8
<212> TYPE: PRT
```

```
<213> ORGANISM: Artificial Sequence
<220> FEATURE:
<223> OTHER INFORMATION: Description of Artificial Sequence:MKP
      catalytic core consensus sequence

<400> SEQUENCE: 17

His Cys Xaa Ala Gly Xaa Xaa Arg
 1               5

<210> SEQ ID NO 18
<211> LENGTH: 9
<212> TYPE: PRT
<213> ORGANISM: Rattus norvegicus

<400> SEQUENCE: 18

Val His Cys Gln Ala Gly Ile Ser Arg
 1               5

<210> SEQ ID NO 19
<211> LENGTH: 5
<212> TYPE: DNA
<213> ORGANISM: Rattus norvegicus

<400> SEQUENCE: 19 attta                                                              5
```

MITOGEN ACTIVATED PROTEIN KINASE PHOSPHATASE CDNAS AND THEIR BIOLOGICALLY ACTIVE EXPRESSION PRODUCTS

RELATED APPLICATIONS

The present application claims priority under 35 U.S.C. §120 from PCT International Application No. PCT/US96/10402, filed Jun. 14, 1996, which is a continuation of U.S. Provisional Ser. No. 60/000,263, filed Jun. 16, 1995, all hereby expressly incorporated by reference.

GOVERNMENT RIGHTS

This invention was made with government support under grant number ROI DK 45921 from the NIH. The government has certain rights in this invention.

FIELD OF THE INVENTION

This invention relates to mitogen activated protein kinase phosphatases and the nucleic acid sequences that encode them. The present invention comprises novel enzymes and the cDNA encoding them. The invention further provides nucleic acid hybridization probes, recombinant expression constructs capable of expressing the mitogen activated protein kinase phosphatases of the invention, homogeneous compositions of the disclosed mitogen activated protein kinase phosphatases, and antibodies against epitopes of each of the mitogen activated protein kinase phosphatases of the present invention.

GENBANK ACCESSION INFORMATION

| GENE | ACCESSION NO. |
| --- | --- |
| Mitogen-activated protein kinase phosphatase-2 (MKP-2) | U23438 |

BACKGROUND OF THE INVENTION

Mitogen-activated protein kinases (MAP kinases) mediate multiple cellular pathways regulating growth (1) and differentiation (2, 3). In neuronal cells, MAP kinase activity mediates the actions of growth factors like EGF that stimulate cellular proliferation as well as factors like NGF that maintain neuronal survival and differentiation (4–6). Such ligand-activated signal transduction pathways involve activation of receptor tyrosine kinases which initiates a series of phosphorylation events that activate a cascade of serine/threonine kinases converging on the MAP kinase (also called extracellular signal regulated kinase (ERK)) isoforms, ERK1 and ERK2 (7–9).

Activation of MAP kinase involves specific phosphorylations on threonine and tyrosine residues within the Thr-Glu-Tyr motif (10) by MAP kinase kinase (MAP kinase and ERK kinase or MEK) (2, 11). Phosphorylation of both these residues is required for MAP kinase activation (11, 12). It has been suggested that the inactivation of MAP kinase is a critical event that regulates the physiological response to MAP kinase activation (13). This inactivation is mediated, in part, by dephosphorylation of MAP kinases by dual specificity phosphatases called MKPs (MAP kinase phosphatases) that dephosphorylate both the threonine and tyrosine residues phosphorylated by MEK (13–16). The activation of MAP kinase appears to be tightly regulated through the coordinate action of MEK and MKPs. By regulating the extent of MAP kinase activation, these MKPs may dictate the choice of differentiation or proliferation within a developing cell (17).

The prototype dual-specificity phosphatase, VH1, was identified in vaccinia and showed similarity to cdc25, a protein that controls cell entry into mitosis (18). VH1 homologues from human (PAC-1, CL100, and most recently B23), mouse [MKP-1 (3CH134 or erp)], and yeast (Yop51, MSG5) have also been isolated (19–24.) All are dual-specificity phosphatases that specifically dephosphorylate MAP kinase in vitro (25) and in vivo (13, 15, 26). MKP-1 (also called 3CH134 or erp) was discovered as an immediate early gene whose rapid transcription and subsequent translation are suggested to provide a feed-back loop to terminate growth factor signals (13, 19, 26). Overexpression of mouse MKP-1 was shown to inhibit dramatically fibroblast proliferation suggesting that the inactivation of MAP kinase in vivo by MKP-1 has a profound negative effect on cellular proliferation (25, 26).

MAP kinase activation by growth factors has been extensively studied in PC12 cells (27). PC12 cells originate from a rat pheochromocytoma and retain many features of neural crest-derived cells, most notably the ability to undergo neuronal differentiation upon stimulation by NGF (28). Transfection with activated forms of the oncogenes ras, raf-1 and src into PC12 cells is sufficient for differentiation in the absence of NGF stimulation (6, 8, 29). As each of these genes has been shown to converge on MAP kinase activation, this implies that components of the MAP kinase cascade are required for neuronal differentiation. More recently it has been shown that the activation of MAP kinase kinase, MAPKK-1, is required and sufficient for PC12 cell differentiation (3). Despite our understanding of MAP kinase activation in neuronal differentiation, we know relatively little about MAP kinase inactivation.

Because of the important role of MAP kinases in controlling cell growth and differentiation, it is desirable to have molecular tools useful for inactivation of these enzymes. The present invention presents such tools.

SUMMARY OF THE INVENTION

An object of the present invention is the development of useful molecular tools for determining and controlling the role of MAP kinases in cell growth and differentiation. Neuronal cells are of particular interest. A further object of the present invention is to provide novel nucleic acids and MAP kinase phosphatases useful in the study and development of drugs aimed at regulating cell growth, differentiation, metabolism, and tumor suppression.

Accordingly, the first aspect of the present invention comprises novel, active homogeneous MAP kinase phosphatase enzyme compositions and the cDNAs encoding them. These compounds are useful for developing hybridization probes and antibodies for assaying MAP kinase phosphatase activity in cells and tissues. Another aspect of the invention provides nucleic hybridization probes, epitopes and antibodies to MAP kinase phosphatase.

Yet another aspect of the invention provides recombinant expression constructs capable of expressing the MAP kinase phosphatases of the invention and homogeneous compositions of the disclosed MAP kinase phosphatases. In this manner, the present invention allows one to obtain large amounts of highly pure protein expression product without resort to the costlier and more time consuming methods involved in purifying the enzymes from tissues.

BRIEF DESCRIPTION OF THE DRAWINGS

The foregoing and other aspects and advantages of the invention will be apparent on consideration of the following detailed description and the accompanying drawings, wherein:

FIGS. 1A and 1B are a representation of the restriction map and sequence of the MKP-2 cDNA. A. The 4.8 kb MKP-2 cDNA was digested with various restriction enzymes and a schematic representation of some of these sites is shown. The following abbreviations are used—RI, EcoRI; Pst, PstI; A, ApaI; H, HindIII; RV, EcoRV; Sma, SmaI; Bam, BamHI; 5' UT, 5' untranslated region; 3' UT, 3' untranslated region; ATG, translation start site; TAG, translation stop site. The coding region of MKP-2 is shown as a rectangular box with 2 different domains highlighted. The stippled box represents CH2 domains (cdc2 homology 2) (42) while the hatched box represents the catalytic domain. B. Nucleotide sequence and the encoded amino acid sequence of rat MKP-2 cDNA is shown (SEQ ID NOS:1,3 and 4). The translation tart site is denoted as +1. The consensus catalytic site, the AU-sequence motifs in the 3' untranslated region, and the putative polyadenylation signal are underlined. The 5' and 3' untranslated regions are depicted in lower case letters.

FIG. 2 shows the amino acid homology between MKP-2 (SEQ ID NO:4), MKP-1 (SEQ ID NO:6), PAC-1 (SEQ ID NO:7), and B23 (SEQ ID NO:8). The amino acid sequences of rat MKP-2, mouse MKP-1, mouse PAC-1, and human B23 are aligned with each other and the areas of homology are shown as shaded boxes. The catalytic domain is boxed. Dots represent spaces put in for alignment. The dark grey boxes represent the two CH2 domains present in all MKPs. Arrows correspond to the primers used in the RT/PCR screening strategy for cloning MKPs.

FIGS. 6A and 6B show the expression of MKPs in rat tissues. A filter containing 2 µg of Poly A+mRNA isolated from the indicated tissues (Clonetech Lab, Inc., Palo Alto, Calif.) was probed with a MKP-2 specific riboprobe (panel A), stripped, and re-probed with a MKP-1 specific riboprobe (panel B). The molecular weight markers are indicated to the right.

FIGS. 8A, 8B, 8C, 8D, 8E and 8F show the localization of MKP-2 mRNA in the rat brain using in situ hybridization. Light field (A,C, and E are thionin counterstains) and dark field (B,D, and F) photomicrographs showing representative distribution of MKP-2 mRNA (32×). DG; dentate gyrus of the hippocampus, Pir; piriform cortex, 3V; Third ventricle, and Sch; suprachiasmatic nucleus of the hypothalamus. Sense MKP-2 riboprobe did not hybridize (data not shown).

FIGS. 14A and 14B show the comparison of JNK activity in PC12 versus MKP2.3 cells. A. PC12 and MKP2.3 cells were serum starved for 24 hours and treated for 15 minutes with the indicated drugs. JNK-1 immune complex assays were performed in duplicate as described using gst-c-jun as a substrate. Quantitative representation of JNK activity assays from an average of two independent experiments is shown. Presented values for all treatments represent fold induction compared with untreated control PC12 cells which were normalized as 1. B. PC12 and MKP2.3 cells were transiently transfected with or without MEKK in the presence of both Gal4-c-jun and 5XGal4-E1B-luciferase as indicated. Luciferase activity was determined and represents an average of three independent experiments.

FIG. 22 is a representation of the corrected sequence of the MKP-2 DNA (SEQ ID NOS:2 and 3) and amino acid sequence (SEQ ID NO:5) (see description of FIGS. 1A and 1B).

FIG. 23 shows the corrected amino acid homology between MKP-2 (SEQ ID NO:5), MKP-1 (SEQ ID NO:6), PAC-1 (SEQ ID NO:7), and B23 (SEQ ID NO:8)(see description of FIG. 2).

DETAILED DESCRIPTION OF THE PREFERRED EMBODIMENTS

Figure 1A:
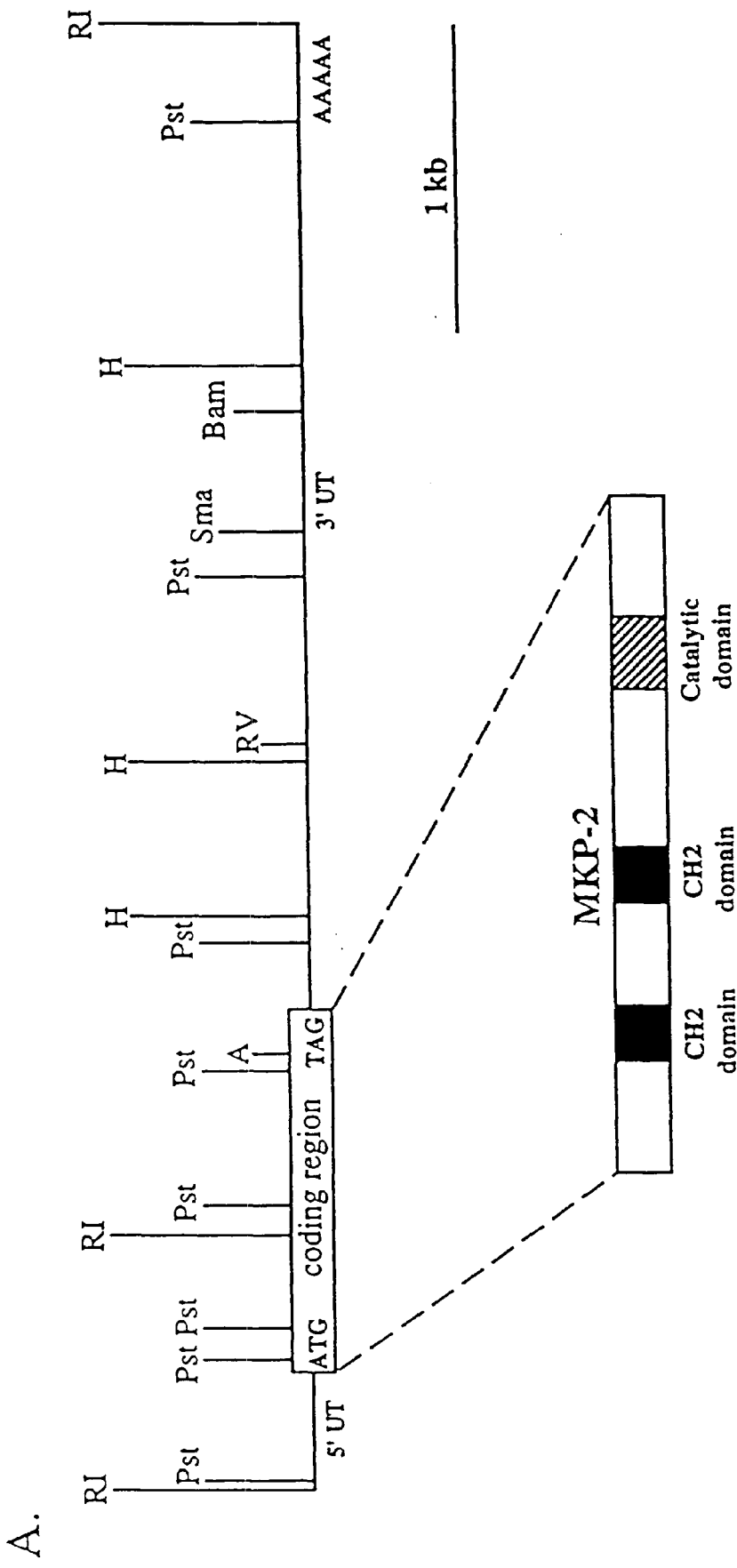

In one aspect, the present invention provides a method of recovering MKP-2 protein in substantially pure form comprising the steps of removing the supernatant from unlysed cells that express MKP-2 protein, introducing the supernatant to an affinity matrix containing immobilized antibody capable of binding to MKP-2 protein, permitting the MKP-2 protein to bind to the antibody of the matrix, washing the matrix to remove unbound contaminants, and recovering the MKP-2 protein in substantially pure form by eluting said MKP-2 protein from said matrix.

The term "substantially pure" indicates a protein or composition that is essentially free of contaminants similar to the protein. In the present case, the normal contaminants associated with rat MKP-2 protein predominately include rat proteins. Thus, rat MKP-2 protein is substantially pure if it is free of rat proteins. "Essentially free" is determined by weight. In general, a composition containing 70% or more by weight rat MKP-2 protein and less than 30% of other rat proteins may be considered substantially pure. Preferably, the composition will be at least 80% rat MKP-2 protein, more preferably at least 90%, and most preferably at least 95% rat MKP-2 protein. The presence of dissimilar components does not affect the determination of purity, thus a composition containing 0.7 mg/mL rat MKP-2 protein in PBS will still be considered substantially pure if it contains less than 0.3 mg/mL other rat proteins. In addition, further purification utilizing a lectin or wheat germ agglutinin column may be used before or after the antibody matrix step. Other purification steps could include, for example, sizing chromatography, ion chromatography, and gel electrophoresis. Further purification by velocity sedimentation through sucrose gradients may be used.

In another aspect of the invention, nucleotide sequences are provided that encode MKP-2 protein, as well as the use of such sequences or fragments thereof in the production of recombinant MKP-2 protein, as hybridization probes, or for other purposes. It will be appreciated that alternate nucleic acid forms, such as genomic DNA, cDNA, and DNA prepared by partial or total chemical synthesis from nucleotides, as well as DNA with deletions or mutations, are also within the contemplation of the invention. Also provided are novel messenger RNA (mRNA) sequences corresponding to these DNA sequences.

Figure 23:
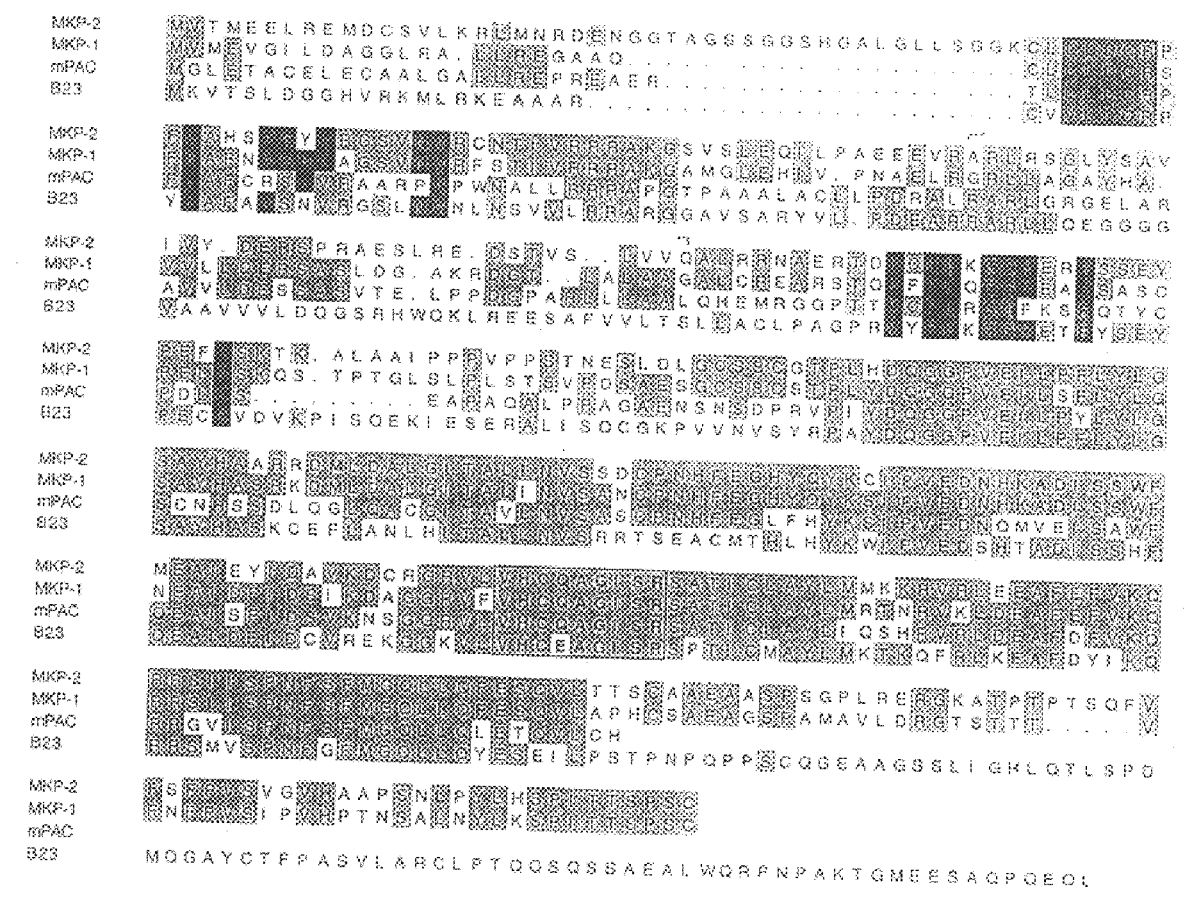

FIG. 22 sets forth the nucleic acid and deduced amino acid sequence of MKP-2 (SEQ ID NOS:2 and 3). FIG. 22 differs from FIG. 1B by six nucleic acid additions and corresponding amino acid changes which are boxed in FIG. 22. FIG. 23 also contains the corrected amino acid sequence for MKP-2 (SEQ ID NO:5).

It will be appreciated that the invention includes nucleic acids having substantial sequence homology with the nucleotide sequence shown in FIG. 22 or encoding proteins having substantial homology to the amino acid sequence shown in FIG. 22. Homology refers to sequence similarity between sequences and can be determined by comparing a position in each sequence which may be aligned for purposes of comparison. When a position in the compared sequence is occupied by the same nucleotide base or amino acid, then the molecules are homologous at that position. A degree of homology between sequences is a function of the number of matching or homologous positions shared by the sequences.

The term "sequences having substantial sequence homology" means those nucleotide and amino acid sequences which have slight or inconsequential sequence variations from the sequences specifically set forth herein, i.e., the homologous nucleic acids function in substantially the same manner to produce substantially the same polypeptides as the actual sequences. The variations may be attributable to local mutations or structural modifications. It is expected that substitutions or alterations can be made in various regions of the nucleotide or amino acid sequence without affecting protein function, particularly if they lie outside the regions predicted to be of functional significance.

Proteins comprising an amino acid sequence which is 90% homologous with the amino acid sequence shown in FIG. 22 may provide proteins having MKP-2 activity. The biological activity of MKP-2 is discussed in greater detail in Examples 1, 2, and 3 below, and is generally defined as the ability of the protein to inactivate MAP kinase.

Isolated nucleic acids encoding a protein having the biological activity of MKP-2 and having a sequence which differs from a nucleotide sequence shown in FIG. 22 (SEQ ID NOS:2 and 3) due to degeneracy in the genetic code are also within the scope of the invention. Such nucleic acids encode functionally equivalent proteins (e.g., a protein having MKP-2 activity) but differ in sequence from the sequence of FIG. 22 due to degeneracy in the genetic code. For example, a number of amino acids are designated by more than one triplet. Codons that specify the same amino acid, or synonyms (for example, CAU and CAC are synonyms of histidine) may occur due to degeneracy in the genetic code. As one example, DNA sequence polymorphisms within the nucleotide sequence of an MKP-2 protein (especially those within the third base of a codon) may result in "silent" mutations in the DNA which do not affect the amino acid encoded. However, it is expected that DNA sequence polymorphisms that do lead to changes in the amino acid sequences of an MKP-2 protein will exist within a population. It will be appreciated by one skilled in the art that these variations in one or more nucleotides (up to about 3–4% of the nucleotides) of the nucleic acids encoding proteins having the biological activity of MKP-2 may exist among individuals within a population due to natural allelic variation. Any and all such nucleotide variations and resulting amino acid polymorphisms are within the scope of the invention. Furthermore, there may be one or more isoforms or related, cross-reacting family members of MKP-2 described herein. Such isoforms or family members are defined as proteins related in biological activity and amino acid sequence to MKP-2, but encoded by genes at different loci.

In another aspect, the invention further includes a method for producing an antibody which is capable of binding to MKP-2 protein or DNA comprising the steps of preparing a peptide-protein or nucleotide-protein conjugate, said conjugate comprising at least 10, more preferably at least 14, and most preferably at least 18 consecutive amino acid or nucleic acid residues present in MKP-2 protein or DNA, immunizing an animal with said peptide-protein or nucleotide-protein conjugate, boosting the animals, and obtaining the antisera. In connection with this aspect, the present invention further includes monoclonal and polyclonal antibodies specific for MKP-2 protein and DNA, i.e., capable of binding to a MKP-2 protein or nucleic acid molecule, as well as hybridoma cell lines capable of producing such an antibody.

In other aspects, the invention includes the use of antibodies specifically directed to MKP-2 protein or nucleotides, such as to isolate MKP-2 protein from sources producing the protein, for purposes of determining the presence or amount of MKP-2 protein in a sample, and for other purposes apparent to those skilled in the art.

This invention further includes a method of diagnosis of the presence and location of an MKP-2 protein expressing cell using labelled nucleotide probe sequences or labeled antibodies of the invention.

The use of rat MKP-2 DNA, or fragments thereof, as a probe in the isolation, purification, and study of other MKP-2 proteins from other organisms is contemplated. Oligonucleotide fragments of MKP-2 DNA can also be used as primers to amplify (with specific DNA polymerase) genomic DNA, isolated, for example, from bacteria, fungi, avian, and mammalian sources. The amplified genomic DNA can then be analyzed to identify sequence variation/abnormality using the polymerase chain reaction assay (Saiki et al., *Science* 230:1350 (1985). See also, Mullis, K. B., U.S. Pat. No. 4,683,202, Jul. 28, 1987; and Mullis, K. B., U.S. Pat. No. 4,683,195, Jul. 28, 1987).

For analysis of mRNA for MKP-2, or mRNA for related proteins, dot hybridization and Northern hybridization analyses can be used to characterize mRNA encoding MKP-2 protein or MKP-2 protein-like molecules quantitatively and qualitatively. From these studies valuable information can be obtained about the number of different forms of MKP-2 genes and their expression in various cell types, e.g., bacteria, fungi, avian, and mammalian.

In the nucleic acid hybridization method according to the present invention, the nucleic acid probe is conjugated with a label, for example, a fluorophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labeled probe or by chemiluminescence. The detection of hybridizable RNA sequences can be accomplished by Northern blot analysis, RNase protection assays, dot blot methodology or an in situ hybridization methodology. Methods of these last two techniques are described by Gillespie and Bresser, "mRNA Immobilization in NaI: Quick Blots," *Biotechniques*, 184–192, (Nov/Dec 1983) and Lawrence and Singer, "Intracellular Localization of Messenger RNAs for Cytoskeletal Proteins," *Cell* 45:407–415 (1986), respectively. The readout systems capable of being employed in these assays are numerous and non-limiting examples of such systems include fluorescent and colorimetric enzyme systems, radioisotopic labeling and detection and chemiluminescent systems.

Another aspect of the invention provides a nucleic acid which hybridizes under high or low stringency conditions to a nucleic acid which encodes a protein having all or a portion of an amino acid sequence shown in FIG. 22. Appropriate stringency conditions which promote DNA hybridization, for example, 6.0× sodium chloride/sodium citrate (SSC) at about 45° C., followed by a wash of 2.0× SSC at 50° C. are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C. to high stringency conditions, at about 65° C.

The foregoing and other aspects of the invention may be better understood in connection with the following examples, which are presented for purposes of illustration and not by way of limitation.

EXAMPLE 1

Materials. Restriction and modification enzymes were purchased from New England Biolabs (Beverly, Mass.), Boehringer Mannheim (Indianapolis, Ind.), and Promega Biotech. (Madison, Wis.). Superscript reverse transcriptase was from Gibco BRL (Gaithersburg, Md.), Taq DNA polymerase from Perkin-Elmer and Sequenase from U.S. Biochemical Corp. (Cleveland, Ohio.). All enzymes were used according to the instructions from the manufacturer. [a-$^{32}$P] dATP (3000 Ci/mmol), $^{35}$S-dATP, $^{35}$S-UTP (1500 Ci/mmol), [g-$^{32}$P]-ATP (800 Ci/mmol), $^{35}$S-Cysteine (1075 Ci/mmol) and [a-$^{32}$P]UTP (800 Ci/mmol at 40 mCi/ml) were purchased from Dupont/New England Nuclear. Oligonucleotides were synthesized by a core facility at Oregon Health Sciences University. Antisera to MKP-1 was purchased from Santa Cruz Biotechnology Inc. An antibody to phosphotyrosine (clone 4G10) was kindly provided by Brian Druker (OHSU, Portland, Oreg.) (30).

Figure 2:
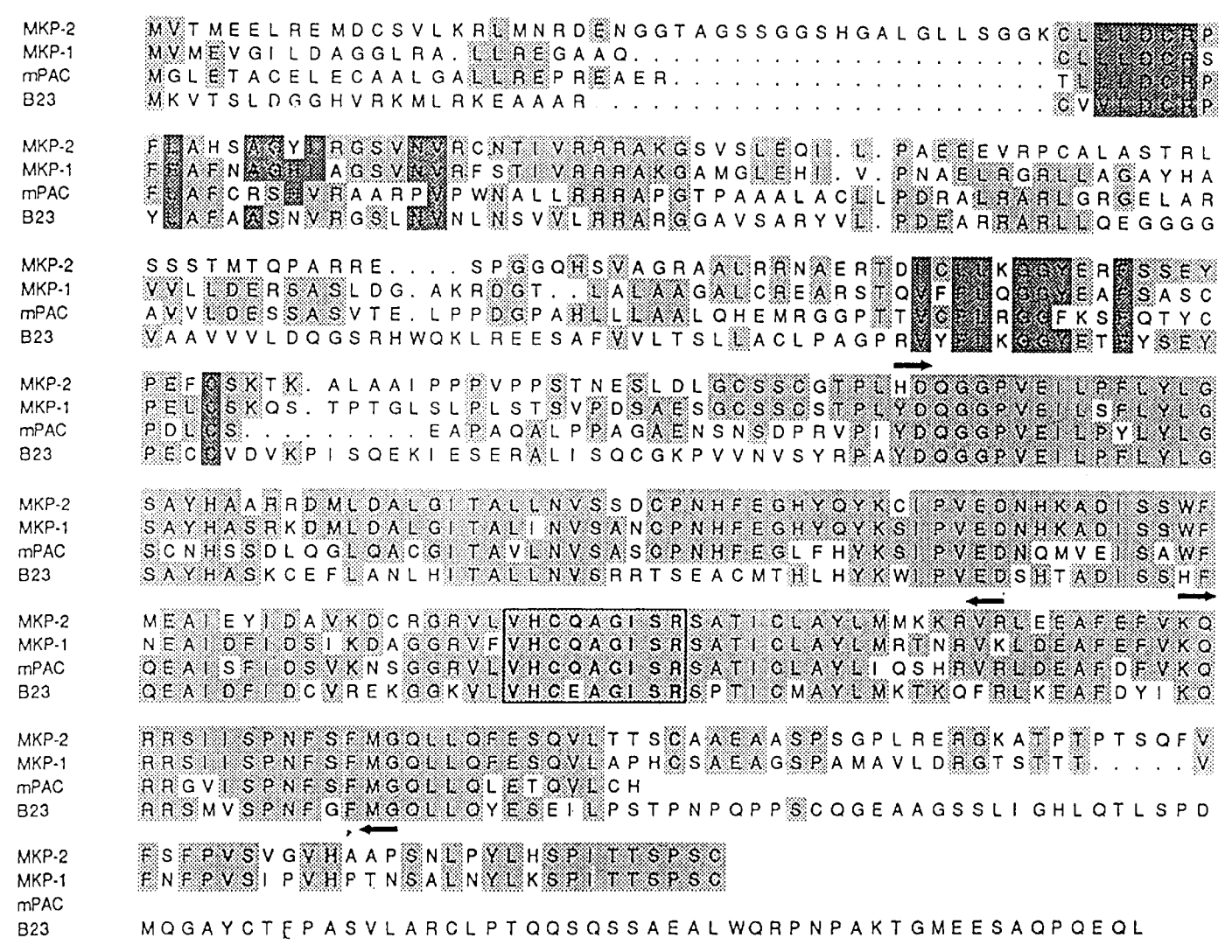

RTIPCR Amplification. One mg of total RNA from PC12 cells was used to generate first strand cDNA after an initial annealing reaction to 0.1 mg of random hexamers at 70° C. for 10 min. Following equilibration to ambient temperatures, a buffer containing 50 mM Tris-HCl pH 8.3, 75 mM KCl, 3 mM MgCl$_2$, 10 mM DTT, 500 mM of each of four dNTPs, and 200 units/mg of Superscript reverse transcriptase (RT) was added and the mix was incubated at 37° C. for 1 hr. The reaction was terminated by placing the tubes on ice and the cDNA was recovered by ethanol precipitation. The pellet was washed with 70% ethanol and resuspended in 100 ml of 5 mM Tris, 0.5 mM EDTA mix. Five ml of this cDNA was used as a template for PCR amplification. Initially, two degenerate oligonucleotides were synthesized that generated a 204 bp cDNA fragment. The 5' primer corresponded to the conserved WFNEAI sequence (SEQ ID NO:9) present in MKP-1 (26) and PAC-1 (23) (5'-TGG-TT(TC)-M(TC)-GA (GA)-GC(GATC)-AT-3', SEQ ID NO:10), while the 3' primer corresponded to the conserved NFSFMG sequence (SEQ ID NO:11) present in MKP-1 (26) and PAC-1 (23) (5'-C-CAT-(AG)AA-(GATC)(GC)(AT)-(AG)AA-(AG)TT-3' (SEQ ID NO:12)) (FIG. 2). Two additional oligonucleotides were made to confirm the novelty of MKP-2. The 5' primer was a degenerate primer corresponding to the conserved YDQGGP sequence (SEQ ID NO:13) (5'-TA(TC)-GA(TC)-CA(AG)-GG(GATC)-GG (GATC)-CC-3', SEQ ID NO:14), while the 3' primer was specific for MKP-2 (5'-ATGAAGAAACGGGTGCGG-3', SEQ ID NO:16) corresponding to MKKRVR sequence (SEQ ID NO:15) (FIGS. 1B, 2). This setqof primers generated a 336 bp cDNA fragment corresponding to nucleotides 628–963 (FIG. 1B, SEQ ID NOS:1, 3). The PCR reaction consisted of 50 mM KCl, 1.5 mMgCl$_2$, 0.2 mM dNTPs, 15 mM Tris-HCl, pH 8.4, and 0.5 mg of each primer pair. PCR was allowed to proceed for 30 cycles. Each cycle consisted of 1 min at 94° C., 1 min at 55° C., and 1 min at 72° C. in a thermocycler (Perkin-Elmer Cetus). The PCR products were purified and subcloned into pBluescript (SK-) (Stratagene) using restriction enzymes engineered at the ends of each of the primers.

Screening of the PC12 CDNA library and isolation of the full length clone. The 336 bp PCR fragment generated by using the specific MKP-2 primer (described above) was labeled by random primed synthesis and used to screen a PC12 oligo dT primed cDNA library in lgt10 with 5×10$^6$ individual recombinants that had been size selected prior to ligation for clones greater than 2 kb. The library was iplated onto 20 LB plates and allowed to grow at 42° C. to a concentration of 50,000 recombinants/plate. The plaques were then transferred onto nitrocellulose filters in duplicate. The filters were soaked in prehybridization/hybridization buffer (6× SSC, 5× Denhardt's, 1% SDS, 0.01M EDTA, 50% Formamide, 100 mg/ml denatured salmon sperm DNA)

at 42° C. for 1–2 hrs with gentle agitation. Random primed probe was made as described in the Boehringer Mannheim kit. One to two million cpm/ml of boiled MKP-2 specific probe was added directly to the prehybridization/hybridization mix and hybridization was allowed to proceed at 42° C. for 24 hrs. The filters were washed in 2× SSC and 1% SDS for 2 hrs at 65° C. with frequent changes in the wash solution. The final wash was in 1× SSC and 1% SDS after which the filters were air dried and put on film. After the tertiary screen, three positive plaques were obtained. Phage DNA was isolated by standard methods and digested with EcoRI to release the insert. The inserts obtained were cloned into pBluescript (SK-) and subjected to restriction enzyme mapping and sequencing.

Sequencing. MKP-2 cDNA inserts obtained were sequenced on both strands by the method of Sanger (31) using sequenase reagents (U.S. Biochemical Corp.) according to the protocol suggested by the manufacturer. Multiple internal primers were made to allow sequencing of the complete 800 bp insert. The 4 kb insert was also sequenced using multiple internal primers on both strands through the termination codon and partially into the 3' untranslated region. Sequences proximal to the polyadenylation signal were also obtained, as shown (FIG. 1B)."

Cell culture and drug treatments. PC12-GR5 cells (courtesy of Rae Nishi, OHSU, Portland, Oreg.) were grown at 5% $CO_2$ in Dulbecco's modified Eagle's medium (DMEM), containing 5% fetal calf serum, 10% horse serum, and L-glutamine. Prior to drug treatments, the cells were serum-starved for 24 h with DMEM containing no serum and treated with either 100 ng/ml NGF or 20 ng/ml EGF for the indicated times.

RNA Isolation. Total cellular RNA was isolated using RNAzol™B (Biotecx Lab, Inc.) according to the manufacturer's protocol. Briefly, cells were grown to 30 to 50% confluency in a 100 mm plate, rinsed with cold phosphate-buffered saline, and scraped into 1 ml of RNAzol B. After vortexing, 0.1 ml of chloroform was added and incubated on ice for 15 minutes. The suspension was centrifuged and the RNA was precipitated from the upper aqueous layer with an equal volume of isopropanol. After pelleting, the RNA was resuspended in water, quantitated at $OD_{260}$, and used directly for RT/PCR or Northern analysis.

Northern blot analysis. Ten μg of total RNA was electrophoresed through a 1.2% agarose formaldehyde gel and transferred onto Magna NT filter (MSI, Westboro, Mass.) using standard methodology in 6× SSC. Filters were prehybridized in three ml of hybridization buffer (5% SDS, 400 mM $NaPO_4$ pH 7.2, 1 mM EDTA, 1 mg/ml BSA, 50% formamide) at 65° C. for 4 hours in a rotating hybridization oven. 2–5×$10^7$ cpm/ml of the antisense riboprobe was then directly added to the hybridization buffer and hybridization was allowed to proceed for 24 hrs. The next day, filters were initially washed in 1× SSC at room temperature for 15 min. and then washed in (0.05× SSC, 0.1% SDS, 5mM EDTA pH 8) at 70° C. for 34 hrs. Filters were autoradiographed at −70° C. on Kodac XAR-5 film using Dupont intensifying screens. Quantitations were performed using a Molecular Dynamics phosphorimager 445 SF and all signals were normalized to the 18S and cyclophilin signals respectively.

Riboprobe Synthesis. The 336 bp cDNA fragment generated by using the specific MKP-2 primer (described under RT/PCR amplification in Experimental Procedures) was subcloned in pBluescript (SK-) and was used to synthesize antisense riboprobes by linearizing the plasmid with Sal I that was engineered into the 5' primer. Full length MKP-1 cDNA (kindly provided by Nicholas Tonks, Cold Spring Harbor Laboratory, Cold Spring Harbor, N.Y.) was subcloned into pBluescript (SK-) and then linearized with Bam HI to generate a 1.9 kb MKP-1 riboprobe. Rat cyclophilin (pSP65 1B15) and 18S ribosomal RNA (18SpSP65) plasmids (kindly provided by James Douglass, Vollum Institute, Portland, Oreg.) were linearized using Pst I and Hind III respectively to generate linear antisense riboprobes. Antisense riboprobes were synthesized as described (32). Briefly, 1 μg of template DNA was incubated in transcription reaction mix (40 mM Tris-HCl pH 7.5, 6 mM $MgCl_2$, 2 mM spermidine, 10 mM NaCl, 10 mM dithiothreitol, 20 units of RNasin, 0.5 mM each of rATP, GTP, and CTP, 12 μM rUTP, 50μM [a-$^{32}$P]UTP; 800 Ci/mmol, and 15 units of the appropriate RNA polymerase) at 37° C. for 60 min. The reaction was stopped by the addition of 2 units of RNase-free DNase and incubated at 37° C. for 15 min. 25 mM EDTA was then added, samples were phenol-chloroform extracted, and ethanol precipitated. Antisense riboprobes were resuspended in water at a concentration of 1–2×$10^6$ cpm/μl.

In situ Hybridization. Male Sprague-Dawley rats (200–300 g) were anesthetized and perfused with 1000 ml of 4% paraformaldehyde in borate buffer, pH 9.5 at 4° C. (fixation buffer). Brains were dissected and incubated in fixation buffer for 8 hrs and then incubated overnight in fixation buffer with 10% sucrose. Brains were sectioned serially into 5 series of 30 mm slices with a sliding microtome. Sections were prepared and hybridized as described (33). The 336 bp MKP-2 specific cDNA fragment was used to synthesize antisense and sense riboprobes. Sections were hybridized with $^{35}$S-labeled riboprobes ($10^7$ cpm/ml) in 66% formamide, 0.26M NaCl, 1.32× Denhardt's solution, 13.2 mM Tris pH 8.0,1.32 mM EDTA, 13.2% dextran sulfate pH 8.0, at 65° C. for 24 hrs. Slides were washed in 4× SSC, digested with RNase A (20 mg/ml for 30 min at 37° C.), and then rinsed in a stringent wash containing 0.1× SSC at 65° C. for 30 min. Sections were dehydrated, dipped in NTB-2 emulsion (Kodak), and developed after 21 days. Light and dark field photomicrographs were taken with a Dialux 22 EB at 32× magnification.

In vitro transcription and translation reactions. Full length MKP-1 and MKP-2 cDNAs were used in a coupled in vitro transcription and translation reaction using TNT™ coupled reticulocyte lysate system (Promega Corp., Madison, Wis.) as per the manufacturer's instructions. Briefly, 1 μg of circular DNA was incubated with 27.5 μl TNT rabbit reticulocyte lysate, 2 μl TNT reaction buffer, 1 μl T7 RNA polymerase, 1 μl 1 mM amino acid mix minus cysteine, 2 μl [$^{35}$S]-cysteine (1075 Ci/mmol at 11 mCi/ml), and 1 μl RNAsin at 40 units/μl in a final volume of 50 μl. The reaction was incubated at 30° C. for 1–2 hrs. The synthesized proteins were separated by SDS-PAGE and analyzed by autoradiography.

PC12 transfection assays. PC12 cells were grown to approximately 60% confluence prior to transfection. For transient transfection experiments, 3 μg of 5xGal4-E1B luciferase and 3 μg of cytomegalovirus (CMV) Gal4-Elk1 transactivation domain (Roberson et al., manuscript in preparation) were used in combination with either 6 μg of Rous sarcoma virus (RSV) promoter coupled to globin (control) or constitutively active form of Raf kinase (Raf BxB); (34) and 30 μg of either pCDNA3(Invitrogen, Inc.) containing the CMV promoter, CMV MKP-1, or CMV MKP-2. Cells were transfected by calcium phosphate-mediated DNA transfer as described (35). Cell lysates were prepared 20–24 hrs following transfection and luciferase activity was determined as described (36).

Western blotting of PC12 proteins. PC12 cells were lysed in 200 μl of a 1% NP-40 lysis buffer (25 mM Tris pH 7.4, 150 mM NaCl, 1 mM EDTA, 1.5 mM MgCl$_2$, 10% glycerol, 1 mM EGTA, 1 mM PMSF (phenylmethylsulfonyl fluoride), 10 upg/ml leupeptin, and 2 mM vanadate). Protein concentrations were determined by the method of Bradford (37). One hundred μg of total protein was resolved on a 12% SDS-polyacrylamide gel and transferred onto Immobilon P membrane. The membranes were probed with an MKP-1 antibody (diluted at 1:2000) (Santa Cruz Biotech., Inc.). A HRP-conjugated secondary antibody was used to allow detection of the appropriate bands using enhanced chemiluminescence (Amersham, U. K.).

Bacterial Expression of MKP-2. The catalytic domain of MKP-2 encoded within a carboxyl-terminal 690 bp fragment (C-MKP-2), extending from amino acids 163–393(SEQ ID NO:4), was subcloned into the PET 23b vector (Novagen) using specific PCR oligonucleotides. This vector provides an amino-terminal epitope tag derived from the T7 capsid protein (T7 tag) that can be detected using specific antibodies (T7 antibody, Novagen). The frame of the resultant cDNA was confirmed by sequencing. This plasmid and the vector alone were used to transform BL21 bacteria (Novagen). A protein of the expected size (28 kD) was induced upon incubation with 0.4 mM Isopropyl-b-8-thiogalactopyranoside (IPTG) and was detected using anti-T7 capsid antibodies. Prior to phosphatase assays, bacterial extracts were prepared in lysis buffer (50 mM Tris-HCl, pH 8.0; 2 mM EDTA) and sonicated. Insoluble debris was pelleted and the supernatant assayed directly.

ERK2 dephosphotylation assay. Activated ERK2 was prepared by incubating 10 ng of recombinant ERK2 (kindly provided by Dr. Edwin Krebs, University of Washington, Seattle, Wash.) with 0.1 mg active MAP kinase kinase (MEK) (Santa Cruz Biotechnology, Inc.) in 1× MEK buffer (25 mM Hepes, pH 7.5; 10 mM MgCl$_2$; 1 mM DTT; and 50 mM [$^{32}$P]-g-ATP) at 30° C. for 30 min. The activation of ERK2 was confirmed by Western blot analysis using an antibody directed against phospho-tyrosine (30). Ten ng of activated ERK2 was incubated with 10 mg of bacterial lystates from MKP-2 expressing and non-expressing cells in 1× Phosphatase buffer (50 mM Tris-HCl, pH 7.5; 1 mM EDTA; 10 mM DTT) for 15 min at 30° C. The reaction was stopped by the addition of an equal volume of 2× Laemmli sample buffer and the samples were separated by 13% SDS-PAGE. The dephosphorylation of ERK2 was confirmed by Western blotting with the phospho-tyrosine antibody using enhanced chemiluminescence for detection of the signal.

Phospho-tyrosine phosphatase assay. The synthetic peptide Raytide (Oncogene Sciences) was phosphorylated on a unique tyrosine using src tyrosine kinase activity immunoprecipitated from C3H10T1/2 cells (kindly provided by Sally Parsons, University of Virginia) as described (38). Bacterial extracts containing 10 to 60 mg of bacterial proteins were incubated at 30° C. for 30 min with labeled peptide (10$^4$ cpm) in 100 ml of 1× phosphatase buffer (described above). Additional reagents [10 mM vanadate, 20 nM microsystin-leucine-arginine (M-LR) and 1 mM okadaic acid] were added without prior incubation. The reaction was terminated by the addition of 0.75 ml of Stop solution (2 mM NaHPO$_4$, 90 mM sodium pyrophosphate, 0.9M HCl, 4% (v/v) Norit A). Following brief centrifugation, 400 ml of the supernatant was added to 2.5 ml of scintillant and the released counts from phosphatase activity were measured on a scintillation counter. All phosphatase assays were performed in duplicate.

RESULTS

PC12 cells express multiple MKPs; identification and cloning of a novel MKP. To identify potential MKPs that are expressed in PC12 cells, a screening strategy involving RT/PCR amplification was employed. Alignment of the sequences of the known members of the MKP family [human PAC-1, mouse PAC-1, mouse 3CH134 and VH1] showed areas of high sequence homology particularly surrounding the catalytic core consensus site (HCXAGXXR, where X=any amino acid) ((23) and FIG. 2 and SEQ ID NO:17). Degenerate primers were designed to the conserved amino acid sequence WFNEAI (5' primer) (SEQ ID NO:9) and the conserved amino acid sequence NFSFMG (3' primer) (SEQ ID NO:11) surrounding the catalytic core site (FIG. 2 SEQ ID NOS:4,6,8). RT/PCR on total RNA from PC12 cells with these two degenerate primers revealed the expected 204 bp product that contained a representative population of MKPs expressed in PC12 cells (data not shown). This PCR product was gel purified, digested with restriction enzymes engineered at the primer ends, and subcloned into the appropriate sites in Bluescript. Five positive clones were obtained that were analyzed by sequencing. One clone was identified as the rat homolog of MKP-1 or 3CH134 (19). The remaining four clones were identical and showed some unique features in comparison to the other known MKPs. To analyze this clone further, two additional primers were designed. The 3' primer was directed to a unique stretch in the cloned novel sequence (MKKRVR, SEQ ID NO:15) (FIG. 2). The 5' degenerate primer was designed to another stretch of conserved sequence between the MKP family members (YDQGGP, SEQ ID NO:13), 5' to the sequence already obtained (FIG. 2). Subsequent amplification using these two primers resulted in a 336 bp amplicon (data not shown). Sequencing this fragment confirmed the novelty of this cDNA sequence (FIGS. 1B, 2 SEQ ID NOS:1,3,4). These results demonstrate that PC12 cells express at least two potential MKPs, MKP-1 and the novel cDNA that we have called MKP-2.

These RT/PCR partial fragments of the novel MKP-2 cDNA were labeled and used as probes to screen an oligo dT-primed PC12 cDNA library in lgt10. This library contained 5×10$^6$ individual recombinants that had been size selected prior to ligation for clones greater than 2 kb. The three positive clones obtained with this screen were plaque-purified and the phage DNA obtained was digested with Eco R1 to release the insert. Upon digestion, two of the three positive clones each revealed two insert fragments of approximately 4 kb and 800 bp while the other clone contained a single 3 kb insert fragment. The 3 kb insert was never successfully subcloned and therefore not analyzed further. The two contiguous insert fragments (4 kb and 800 bp) were cloned separately into Bluescript and characterized by restriction analysis (FIG. 1A) and sequencing (FIG. 1B). The 5' untranslated region and the first 135 amino acids of the novel MKP were contained within the 800 bp fragment, while the remaining 3' end of the clone was contained in the 4 kb fragment. The cDNA encoding MKP-2 contained at least 377 bp of 5' untranslated region and a translation start site with a 11/13 match with the Kozak consensus sequence (FIG. 1B, SEQ ID NOS:1,3,4). The open reading frame extends 1182 bp and encodes a protein product of 393 amino acids with a predicted molecular weight of 42.6 kD and an isoelectric point of 7.86. The open reading frame was followed by an unusually large 3' untranslated region of greater than 3.0 kb. In comparison, the size of full length mouse MKP-1 (3CH134, erp) and its human homolog (CL100) is only 2.4 kb (19, 22, 26) similar to the recently cloned member of this family, B23, which is 2.5 kb (24). The large 3' untranslated region of MKP-2 (SEQ ID NOS:1,3,4) contains several AU sequence motifs (FIG. 1B) that are thought to regulate mRNA stability and are also present in MKP-1 (26).

Figure 3A:
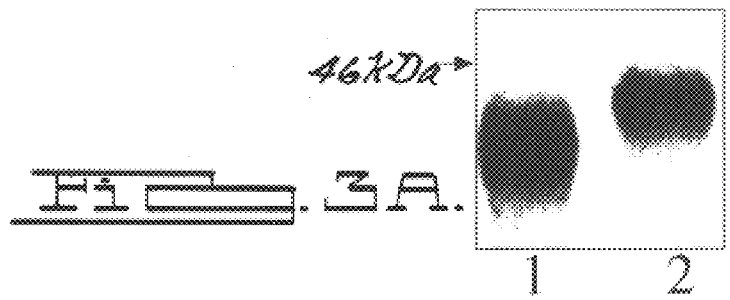
FIGS. 3A and 3B show the in vitro translation of MKP-1 and MKP-2 cDNAs. A) Autoradiogram of $^{35}$S-cysteine labeled products of a coupled in vitro transcription-translation reaction are shown using cDNAs encoding MKP-1 (lane 1) and MKP-2 (lane 2). B) Western blot analysis of PC12 cell lysates (100 µg total protein) using antisera directed to a MKP-1 peptide with significant identity to the C-terminal residues of MKP-2 (Santa Cruz Biotech). A 46 kD protein molecular weight marker is indicated.
Figure 3B:
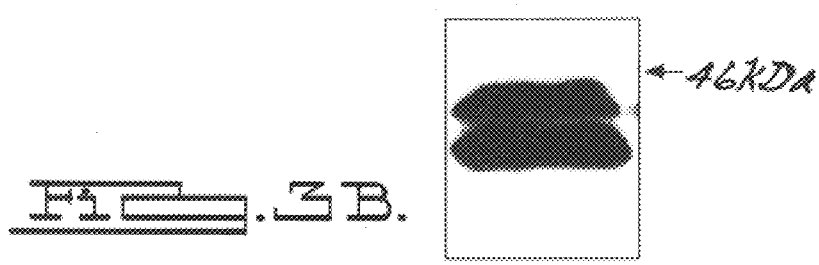
Figure 5A:
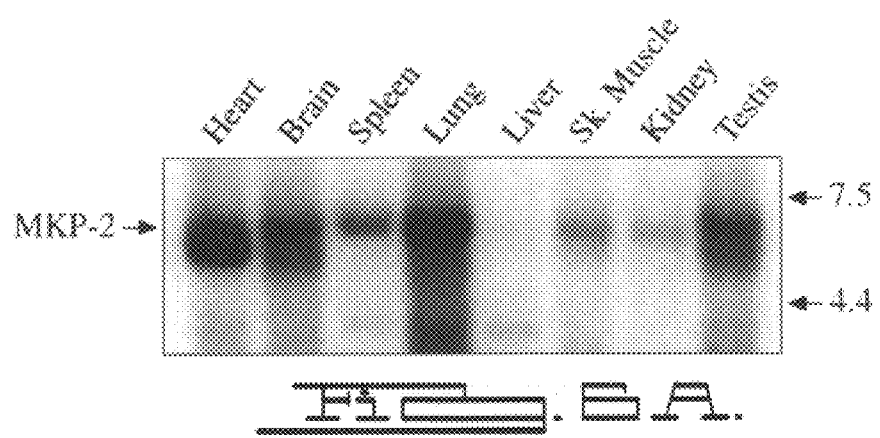
FIG. 5 shows the ability of MKP-2 to block MAP kinase-dependent gene transcription. PC12 cells were transfected with 6 µgs of either RSV-globin (control) (white bars) or Raf B×B (constitutively active Raf) (grey bars) in the presence of 30 µgs of vector alone (CMV), CMV-MKP-1 (MKP-1) or CMV-MKP-2 (MKP-2). In addition all cells received 3 µgs of the reporter 5x Gal4-E1B luciferase and 3 µgs of Gal4-Elk-1. Activity is shown as light units/100 µg protein. Note the activities of cells transfected with RSV-globin and either MKP are below the limits of detection.
Figure 5B:
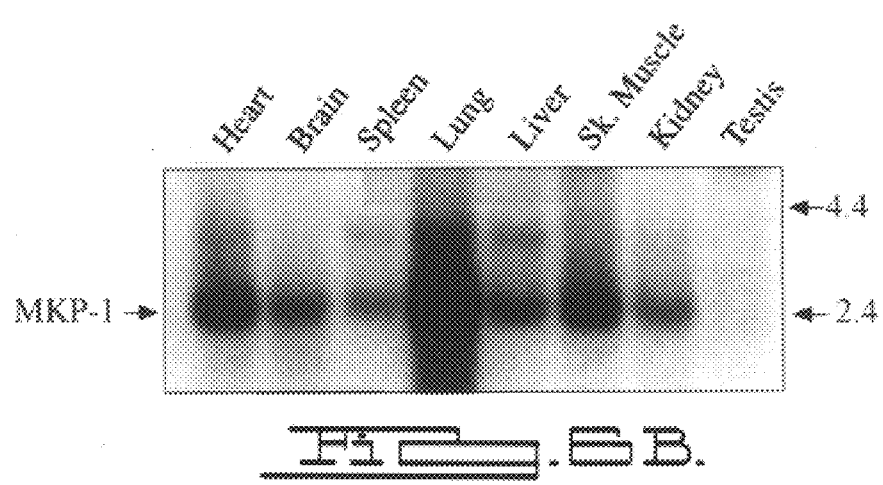

The putative 393 amino acid MKP-2 protein shares 58.8% identity to the 367 amino acid MKP-1 protein, 62.3% identity to the 314 amino acid MPAC protein, and 33% identity to the 397 amino acid human B23 protein (FIG. 2, SEQ ID NO:4, 6–8). The similarities are greatest at the 3' end near the catalytic domain. In contrast, however, the 5' end has significant sequence differences compared to the other members of this family. The N-terminal half of MKP-2 (amino acids 1–187) shares only 33% identity to MKP-1 while the C-terminal half (188–393) shows much greater homology (76%) with nearly 100% identity around the catalytic core (FIG. 2). The complete coding region of MKP-2 was subcloned into Bluescript to generate a full length cDNA (MKP2FL-6) to allow transcription from the T7 promoter. In vitro transcription and translation of MKP-1 and MKP-2 cDNA revealed the expected 39.4 kD and 42.6 kD proteins respectively (FIG. 3A). Antisera directed to an MKP-1 C-terminal peptide sequence (amino acids 348–366) detected proteins of sizes similar to MKP-1 and -2 from PC12 cell lysates (FIG. 3B). This cross-reactivity is likely the result of the significant homology between MKP-1 and -2 in this region (FIG. 2).

Figure 4A:
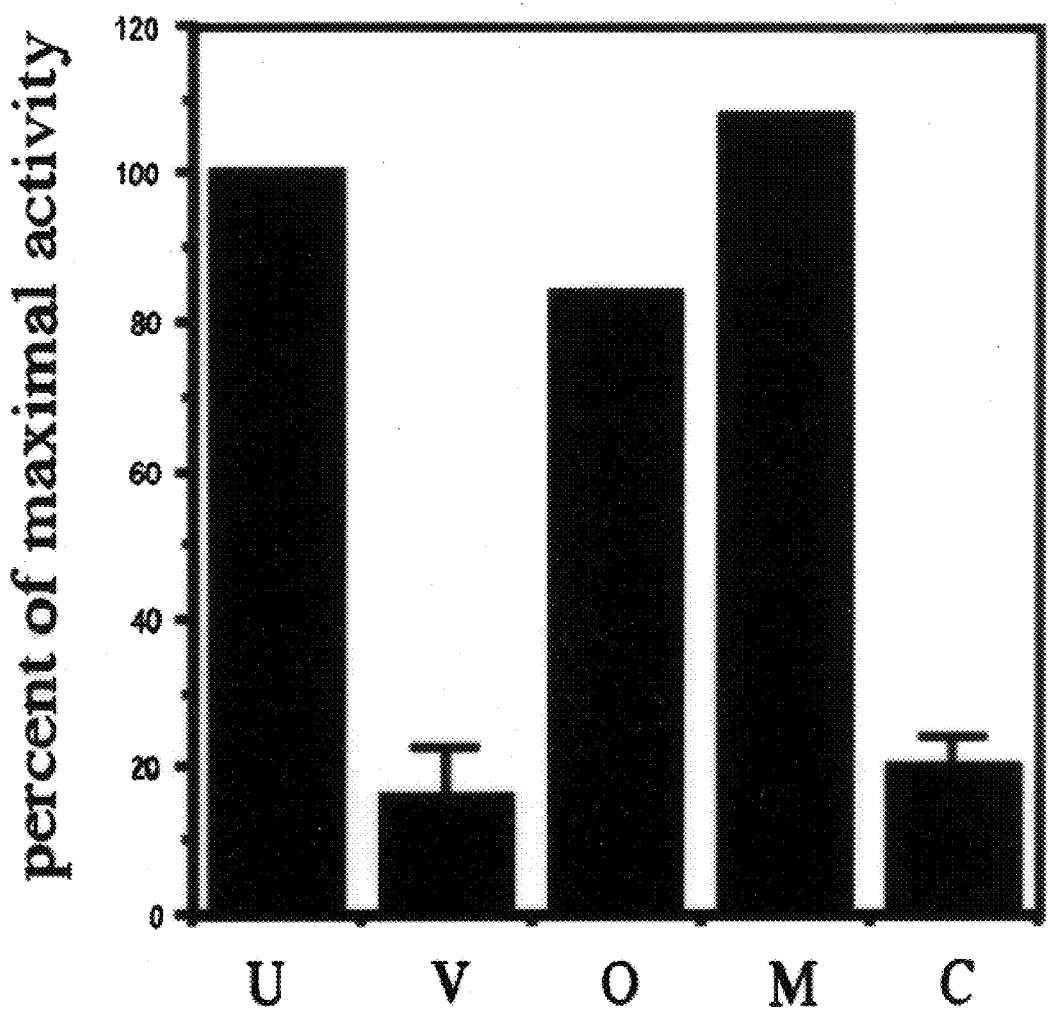
FIGS. 4A and 4B show that MKP-2 contains phosphotyrosine phosphatase activity. A) Dephosphorylation of the synthetic peptide Raytide by bacterial lysates expressing a truncated MKP-2 protein (amino acids 163–393). U; untreated extracts from bacteria expressing MKP-2, V; vanadate-treated extracts, O; okadaic acid treated, M; microcystine treated extracts, and C; control extracts from bacteria expressing vector alone. The activity is represented as percent of maximal stimulation. B. Dephosphorylation of ERK2 by MKP-2 is shown. Activated ERK2 (pp42) (see Experimental Procedures) was incubated with phosphatase buffer alone (lane 1), bacterial lysates expressing vector alone (lane 2), bacterial lysates expressing truncated MKP-2 protein (lane 3), bacterial lysates expressing MKP-2, assayed in the presence of vanadate (lane 4). Phosphorylation was assayed by Western blotting with a phosphotyrosine antibody as described.
Figure 4B:

The MKP-2 protein contains phosphotyrosine phosphatase activity. A carboxy terminal fragment of MKP-2 (amino acids 163–393) comprising the entire catalytic domain was subcloned into the bacterial expression vector PET-23b and expressed in the E. coli strain BL21 (LysS). Induction of bacterially expressed truncated MKP-2 by IPTG was confirmed by Western blotting using an antibody directed to the T7 capsid epitope (data not shown). Bacterial extracts expressing the truncated MKP-2 fusion protein displayed phosphotyrosine phosphatase activity that was inhibited by vanadate, but not by okadaic acid nor microcystine-LR, inhibitors of serine/threonine phosphatases (39, 40) (FIG. 4A). These extracts, but not extracts expressing vector alone, could dephosphorylate activated ERK2 protein in vitro as monitored by phospho-tyrosine Western blotting (FIG. 4B). This dephosphorylation was blocked by vanadate (FIG. 4B).

Figure 5:
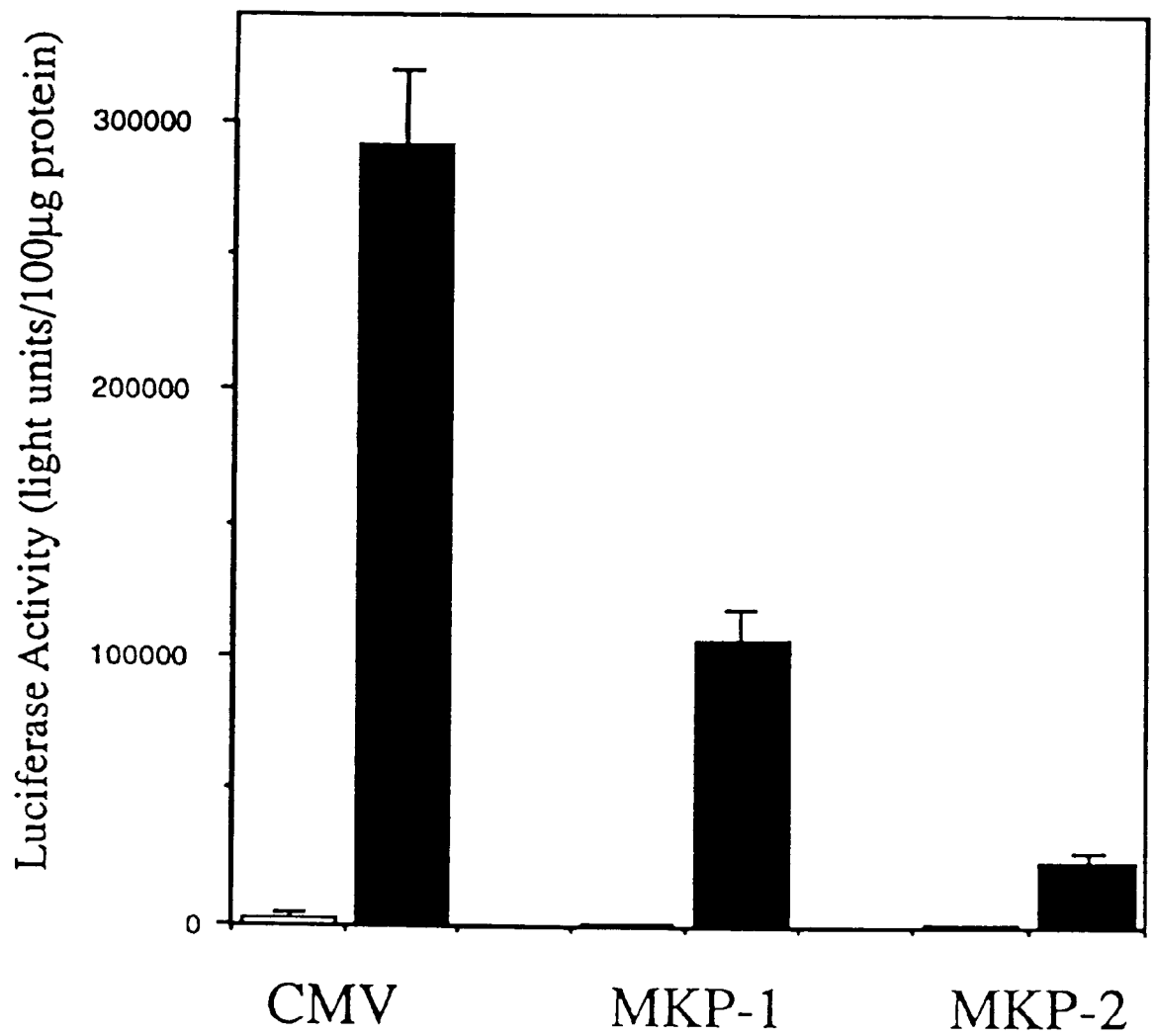

MKP-2 blocked MAP kinase-dependent activation of the Elk-1 transactivation domain. To demonstrate biologically significant activity towards ERKs in vivo, the full-length cDNA encoding MKP-2 (MKP-2FL-6 cDNA) was subcloned into a CMV driven expression vector (CMV-MKP-2) and expressed in PC12 cells with a Gal4-Elk-1 fusion protein used to direct expression of a Gal4-luciferase reporter. Transcriptional activation by the Elk-1 transactivation domain requires activated MAP kinase (41). In these cells, a constitutively active Raf-1 mutant, Raf BxB, induced Elk-1 dependent transcription of the luciferase reporter by greater than 100-fold (FIG. 5). Co-transfection with a MKP-1 expression vector under the control of a CMV promoter (CMV-MKP-1) blocked the activation by greater than 60% of maximally stimulated levels. Co-transfection with similar amounts of CMV-MKP-2 reduced expression by greater than 90% of maximal levels (FIG. 5). These studies demonstrate that MKP-2 can potently inhibit transcriptional activation that is dependent on MAP kinase. Unstimulated activation of Elk-1 was assayed in the presence of serum. Both MKPs inhibited this "basal" expression of luciferase activity to undetectable levels, presumably by blocking serum-induced MAP kinase activity.

MKP-2 is expressed in most tissues and cell lines examined; distinct expression compared to MKP-1. To determine the distribution of MKP-2 in various tissues, Northern blot analysis using a 336 bp MKP-2 specific riboprobe (described in Experimental Procedures) revealed expression in most tissues obtained from 10–12 week rats (FIG. 6A). MKP-2 mRNA was detected in most tissues including brain, spleen, and testes with the highest expression in the heart and lung and lower expression in skeletal muscle and kidney. No MKP-2 expression was detected in the liver. The same blot was stripped and reprobed with a riboprobe made to the entire coding region of MKP-1 (FIG. 6B). This probe did not cross react with the 6 kb MKP-2 transcript. A 2.4 kb mRNA corresponding to MKP-1 was detected in all tissues but testes. The highest expression of MKP-1 was seen in the lung, as previously reported (19, 26), and in the heart (similar to MKP-2). In the testes, MKP-2 is abundantly expressed but not MKP-1. In the liver, the inverse expression pattern is found. These opposite expression patterns in two different tissues suggests different physiological roles for the members of the MKP family. These results show a fairly abundant basal expression of MKP-1 and MKP-2 in most tissues with distinct tissue distribution patterns between MKP-1 and MKP-2. MKP-2, as expected from the 4.8 kb cDNA which was missing a portion of the 5' untranslated region, encodes an approximate 6 kb transcript distinct from the 2.4 kb MKP-1 mRNA detected in the same tissues.

Figure 7A:
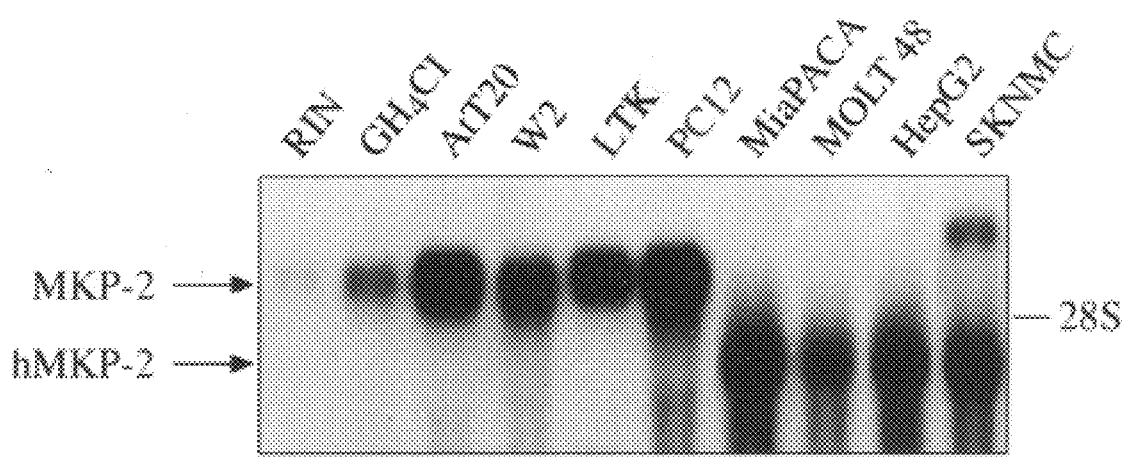
FIGS. 7A and 7B show the expression of MKPs in cell lines. 10 µg of total RNA was isolated from each of the cell lines indicated and probed with an MKP-2 specific riboprobe (panel A), stripped, and re-probed with a MKP-1 specific riboprobe (panel B). The migration of the ribosomal bands is indicated to the right. hMKP-2 refers to an MKP-2 specific transcript detected only in cells of human origin. Abbreviations for the cell lines include: RIN, rat insulinoma; $GH_4Cl$, rat pituitary tumor; AtT20, mouse pituitary tumor; W2, rat medullary thyroid carcinoma; LTK, mouse fibroblasts; PC 12, rat adrenal medullary tumor; MiaPACA, human pancreatic carcinoma; MOLT48, human lymphoblasts; HepG2, human hepatoblastoma; SKNMC, human neuroblastoma.
Figure 7B:
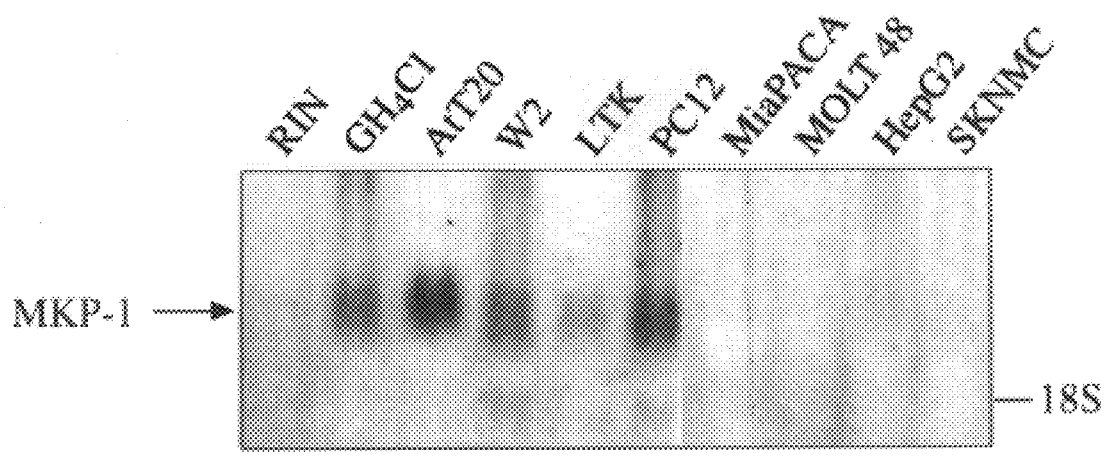
Figure 5A:
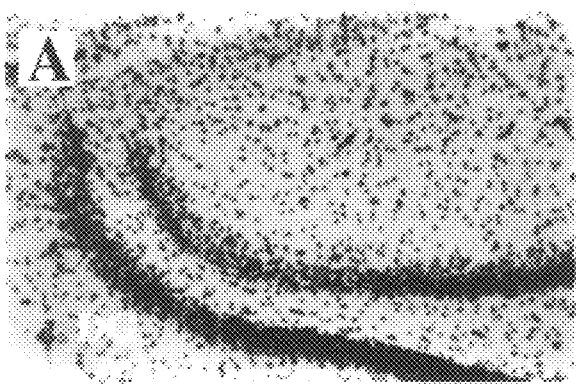
Figure 5B:
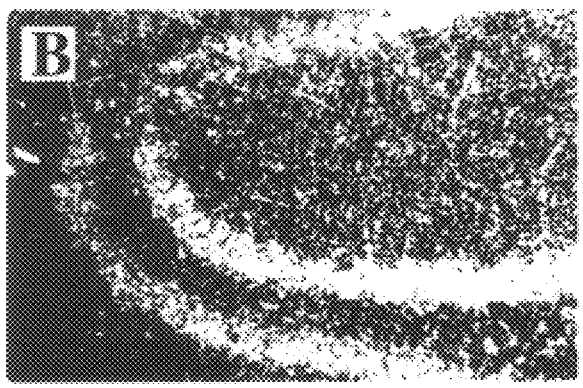
Figure 5C:
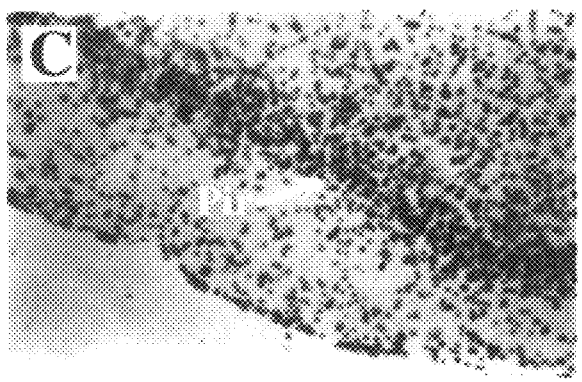
Figure 5D:
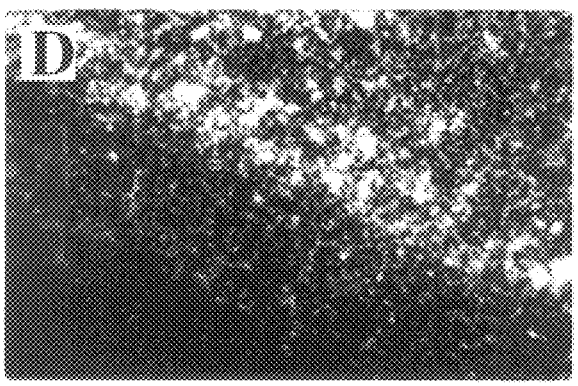
Figure 5E:
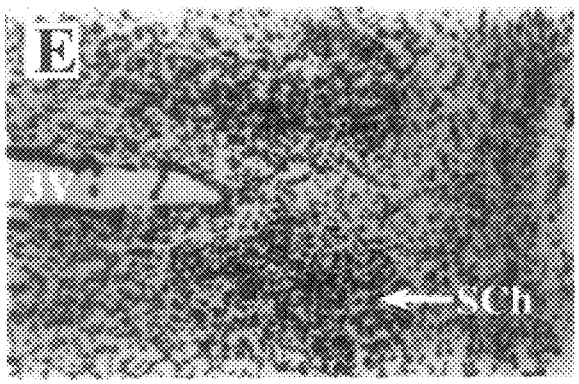
Figure 5F:
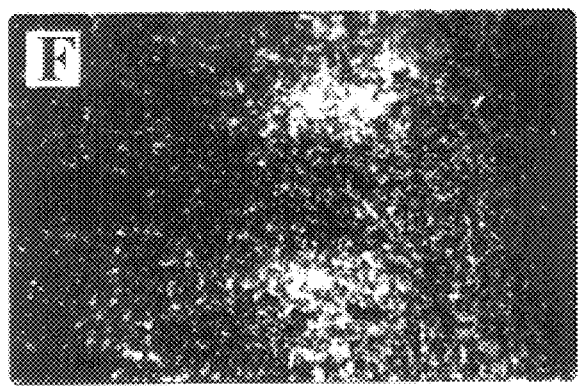

RNA was also isolated from cell lines of different lineages and 10 mg of total RNA from various cell lines was analyzed by Northern analysis using the 336 bp MKP-2 specific riboprobe (FIG. 7A). A single 6 kb MKP-2 transcript was detected in all rat and mouse derived cell lines of different lineages while a single ~4 kb MKP-2 transcript was detected in all cells of human origin. The same blot was stripped and reprobed with an MKP-1 riboprobe (FIG. 7B). No MKP-1 was detected in cells of human origin. This may reflect the inability of the mouse MKP-1 riboprobe to hybridize across species to cells of human origin under the stringent conditions used. A rat MKP-1 probe was also used with similar results (data not shown).

Distribution of MKP-2 in the CNS. It has been shown that ERK1 mRNA is expressed in all areas of the brain with the strongest expression in the hippocampus and piriform cortex while there was no overlapping expression of CL100 (human MKP-1) in those same areas (42). In order to determine the distribution of MKP-2 mRNA in the brain, we performed in situ hybridization analysis on rat brain sections with an $^{35}$S-antisense and sense MKP-2 riboprobe. MKP-2 appeared to be expressed in many areas of the brain with very strong staining of the hippocampus, piriform cortex, and the suprachiasmatic nucleus (FIG. 8). The sense riboprobe did not show any specific staining (data not shown). These results suggest the colocalization of an ERK isoform, ERKI, and a MKP isoform, MKP-2, in specific areas of the brain where MKP-1 is not expressed.

Regulation of MKP-1 and MKP-2 in PC12 cells. MKPs have been shown to be immediate early genes and are transcriptionally regulated by a variety of agents. For example, MKP-1 mRNA appears to be induced by bombesin, EGF, TPA, cAMP, and FGF to different extents and with different kinetics suggesting the involvement of this phosphatase in various signaling pathways (26). A recent member of the MKP family, B23, has also been shown to be regulated by serum in human skin fibroblasts (24). In order to determine the involvement of MKP-2 in different neuronal signal transduction cascades in PC12 cells, Northern blot analysis was performed to determine the levels of MKP-1 and -2 mRNA following growth factor stimulation.

Figure 9A:
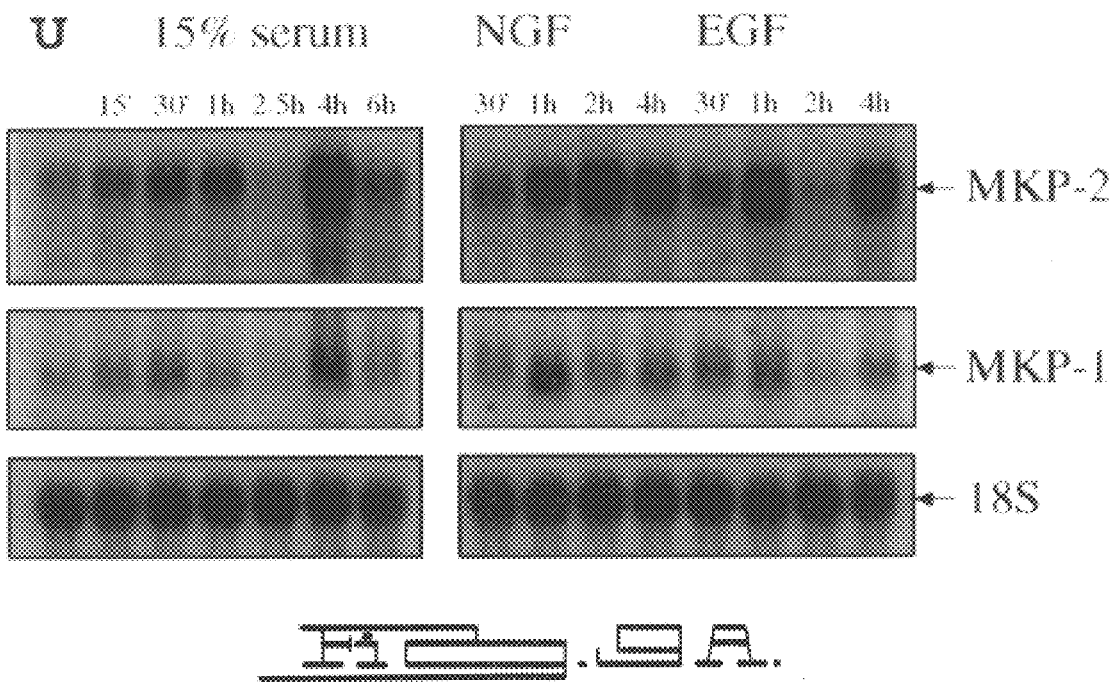
FIGS. 9A and 9B show the effect of serum and growth factors on MKP-1 and MKP-2 mRNA. A. PC12 cells were serum starved for 24 h (U, untreated control) and were treated with medium containing 15% serum for the indicated times (left panel) or with NGF (100 ng/ml) or EGF (20 ng/ml) for the indicated times (right panel). 10 µg of total RNA from each treatment was analyzed by Northern blot analysis using an MKP-2 specific riboprobe, the filter was stripped and re-probed with MKP-1, stripped again and re-probed with a 18S ribosomal RNA probe. The results from each probe are shown. B. Quantitative representation of MKP-1 and -2 mRNA levels normalized to the 18S ribosomal RNA from an average of two independent experiments, one of which is shown in A. Presented values for all treatments represent fold induction compared to untreated cells (lane U) which was normalized as 1. The columns are aligned so as to be directly underneath the treatments indicated in A. Black boxes represent MKP mRNA levels in PC12 cells serum stimulated for the indicated times, grey boxes represent MKP mRNA levels from serum starved PC12 cells treated with NGF for the indicated times, and the white boxes represent MKP mRNA levels from serum starved PC12 cells treated with EGF for the indicated times.

To determine whether MKP-2 mRNA is serum-inducible, total RNA was isolated from PC12 cells that were serum starved overnight and then stimulated with media containing 15% serum for various times. Ten mg of RNA from each treatment was analyzed by Northern analysis using an MKP-2 specific riboprobe as described above. Both MKP-1 and MKP-2 were expressed in unstimulated PC12 cells (FIGS. 7A, B and FIG. 9). Serum stimulation caused a biphasic stimulation of MKP-2 with a gradual increase by 1 hr followed by a transient decrease and then a subsequent increase in expression of MKP-2 by 4 hr. The same blot was stripped and reprobed with MKP-1 and the MKP-1 transcript followed a similar but less robust stimulation (FIGS. 9A, B, left panel). All quantitations were normalized to the 18S ribosomal RNA as an internal control.

Figure 9B:
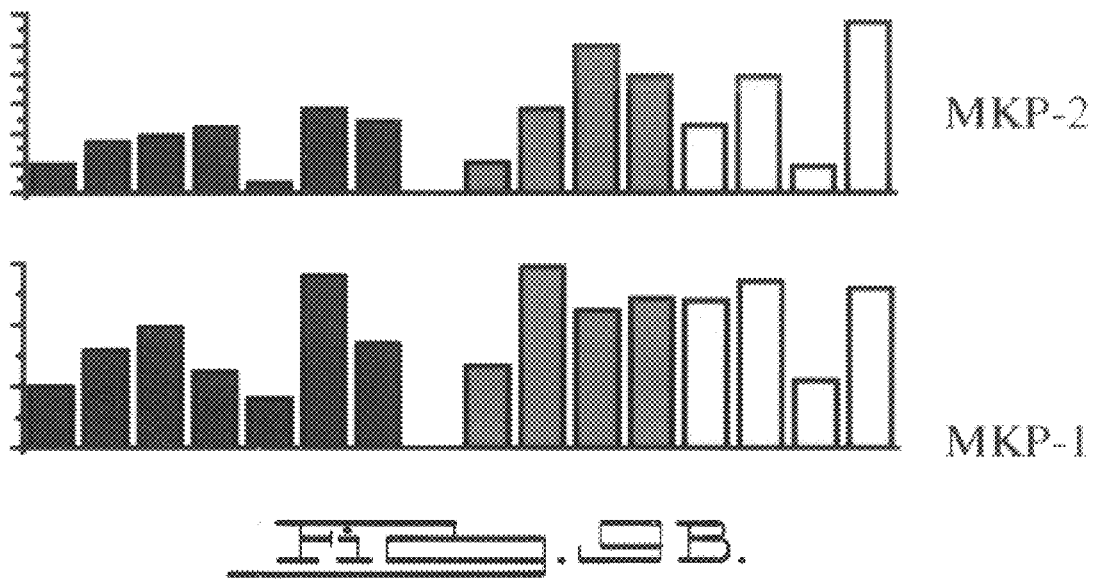

To address whether differences in the induction of distinct MKPs may account for the differences observed in the kinetics of MAP kinase activation seen following NGF and EGF treatment of PC12 cells (5), PC12 cells were serum-starved and treated with NGF or EGF for various times. Ten mg of total RNA from each of these treatments was analyzed by Northern blot analysis for MKP-1 and -2 expression (FIG. 9A, right panel). All quantitations were normalized to 18S ribosomal RNA which was used as an internal control for amount of RNA loaded (FIG. 9B, right panel). NGF induced expression of MKP-1 and MKP-2 by 1 hr. Continued stimulation by NGF resulted in a maximum of 5-fold increase in MKP-2 expression by 2 hr and a 3-fold increase in MKP-1 expression by 1 hr. Both MKP-1 and -2 were maintained at slightly elevated levels upon NGF stimulation. 1 hr of EGF also induced expression of MKP-1 by 2.7-fold and MKP-2 by 4-fold. In contrast to NGF, this induction however was inhibited after 2 hr of EGF treatment in both cases. Additional incubation with EGF resulted in a second induction of both MKP-1 (2.6-fold) and MKP-2 (5.7-fold) by 4 hr. This bi-phasic kinetic pattern was also seen following stimulation with serum, with a minimum RNA level seen at 2–2.5 hr, as well (FIG. 9B). These results show that growth factors that activate members of the MAP kinase cascade also result in the transcriptional activation of MKPs. The significance of the different kinetic pattern of MKP induction by NGF and EGF has yet to be determined.

Figure 10A:
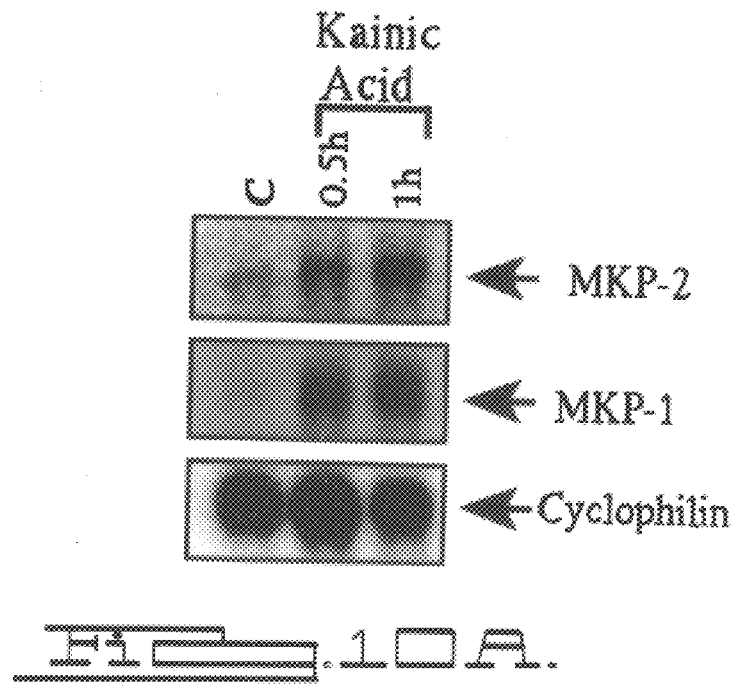
FIGS. 10A and 10B represent the induction of MKPs in the hippocampus by Kainic acid. 10 µg of total hippocampal RNA was isolated from control rats (C) or rats treated with 8 mg/kg Kainic acid for the indicated times (kindly provided by Drs. James Douglass and Pastor Couceyro). A. Northern blot analysis was performed with a MKP-2 specific riboprobe, the filter was stripped and probed with MKP-1, stripped again, and re-probed with cyclophilin as an internal control. B. The blot was quantitated and the results were normalized to cyclophilin and are shown graphically. The black box is the amount of MKP-1 mRNA and the grey box represents the levels of MKP-2 mRNA.
Figure 10B:
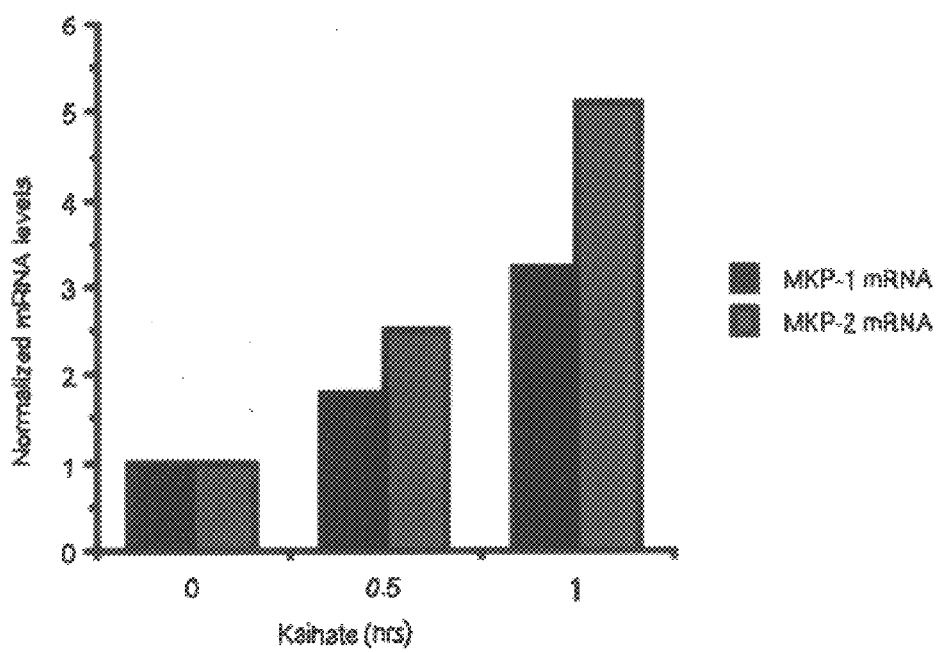

Regulation of hippocampal expression. Due to the high expression of MKP-2 mRNA in the hippocampus (FIG. 8), we analyzed MKP-2 expression after adult rats (250–300 g) had been subjected to the global seizure inducing drug, kainic acid (8 mg/kg). RNA from the hippocampus of rats subjected to kainic acid was extracted 0.5 and 1 hr after drug treatment and analyzed by Northern blot analysis (FIG. 10A). Quantitations were normalized to the amount of cyclophilin in each case. MKP-2 mRNA was induced 5.1-fold by 1 hr of kainic acid treatment while MKP-1 mRNA was induced 3.2-fold (FIG. 10B). This kainic acid induced transcriptional stimulation of MKPs shows the involvement of these genes in the stress-induced pathways in the brain.

DISCUSSION

We have identified a second widely-expressed MAP kinase phosphatase we term MKP-2. It is co-expressed with MKP-1 in a large number of tissues but also shows distinct differences. In contrast, the MKP PAC-1, is expressed only in lymphoid cells (23). Like MKP-1 and PAC-1, MKP-2 shows homology to other yrosine phosphatases. Its sequence is most conserved with MKP-1 and PAC-1 ithin the C-terminus and less so within the N-terminus (FIG. 2, SEQ ID NOS:4, 6–8). All three share identity within the catalytic core (VHCQAGISR, SEQ ID NO:18), and display phostyrosine phosphatase activity against synthetic peptides and purified MAP kinase. The dual specificity of MKP-2 towards a phospho-threonine has yet to be proven. However, we have shown that both MKP-2 and MKP-1 block MAP kinase-dependent gene transcription in vivo, as been shown for PAC-1 (15). All four MKPs contain the CH2 domains (cdc25 homology 2) which are regions present in members of the cdc25 family that flank the catalytic domain (42). In MKPs, the catalytic domain is situated at the C-terminus and not at the N-terminus where the CH2 domains are found (FIG. 2). Whether these CH2 domains are functional has yet to be proven but they have been speculated to either increase substrate selectivity or to be involved in localizing proteins to nuclear or cytoskeletal locations (42).

The large (>3 kb) 3' untranslated region in MKP-2 differs from the shorter (697 bp) 3' untranslated region present in MKP-1 and may play a regulatory role in post-transcriptional events such as transcript stability. Several AUUUA motifs (SEQ ID NO:19) are found in the 3' untranslated region of both MKP-1 (19, 26) and MKP-2 (FIG. 1B, SEQ ID NOS:1,3). MKP-2 also has a 25 nucleotide stretch of AU sequences which might also contribute to posttranscriptional control. These AU sequence motifs have been implicated in the short half life (~10 min) of MKP-1 mRNA(19). Such runs of AU sequences occur in the 3' untranslated regions of lymphokines, cytokines and proto-oncogenes and are thought to be recognition signals for selective mRNA degradation (43). The role of these motifs in MKP-2 regulation has yet to be determined.

In contrast to the expression of PAC-1 which is limited to lymphoid cells (23), MKP-1 and MKP-2 show expression in a broad range of tissues with distinct differences. These distinct tissue distribution profiles may dictate unique roles of the members of this family in the regulation of MAP kinases and might reflect their co-expression with certain MAP kinase isoforms. MKP-1, ERK-1 (42) and MKP-2 mRNA are expressed in discrete areas of the brain. ERK2 expression is also prominent in neuronal cell bodies and dendrites particularly within the superficial layer of the neocortex, the hippocampal CA3 region, dentate gyrus, and cerebellar Purkinje cells (44). The co-localization of MKP-2 and the ERK isoforms in certain discrete areas of the brain suggests that ERK1 and ERK2 may be physiological substrates for MKP-2. However, MKP-1 and MKP-2 also show overlapping expression which suggests that co-expression of MKPs and ERKs is not the only criterion for substrate specificity.

The function of MAP kinase in post-mitotic neuronal cells is unclear. MAP kinases within the developing and adult central nervous system (45) are activated by both neurotrophic growth factors and neurotransmitters. For example, activation of the N-methyl-D-aspartate (NMDA) receptor leads to increased tyrosine phosphorylation of an ERK isozyme in hippocampal cultures (46). Kainate is an NMDA receptor antagonist that induces seizures and immediate-early genes within the hippocampus (47, 48). The induction of CL100 (human MKP-1) and B23 mRNA by oxidative stress and heat shock has been reported (22, 24) and the induction of MKP-1 and -2 observed with kainic acid treatment may represent a regulatory role these genes might play in response to cellular stress. It is not known whether the stress activated kinases are substrates for the MKPs (49).

Basal expression of MKPs may be important for the resting cell. Vanadate stimulates MAP kinase activity in resting PC12 cells (data not shown). This suggests that a constitutive tyrosine phosphatase activity may inhibit basal MAP kinase activity. In addition, the introduction of dominant negative mutants of MKP-1 into unstimulated COS cells activates MAP kinases in the absence of serum (13). Therefore MKPs may be active in resting cells and might function to minimize the level of basal MAP kinase activity in the resting cell.

In PC12 cells, both NGF and EGF stimulate a receptor tyrosine kinase to phosphorylate and activate similar intracellular substrates including MAP kinase, whose action is required for both proliferative and differentiating responses (3, 4, 50). It has been suggested that the duration of MAP kinase activation determines the biological response to growth factor stimulation (5, 51). Proliferation is associated with a transient MAP kinase activation (5, 51, 52), while agents that induce a differentiating response produce a sustained activation. It is not known whether regulation of MKPs establishes the time courses of MAP kinase inactivation. We demonstrate that both NGF and EGF induced a rapid increase in MKP-1 and MKP-2 mRNA levels with a more substantial increase in MKP-2 compared to MKP-1. Whether this induction of MKPs is responsible for the rapid inactivation of MAP kinase by EGF is not known. A recent report demonstrates that inactivation of MAP kinase by EGF is independent of MKP-1 induction (53). Our results would agree with their findings as NGF, which sustains the level of active MAP kinase for a longer duration than EGF, also resulted in elevated levels of MKP-1 and -2 for at least 4 hr of drug exposure. Therefore, it is possible that the MKPs are regulated post-transcriptionally by these agents. The differences in transcriptional regulation of MKP-1 and MKP-2 by NGF and EGF suggest that they have different mechanisms of regulating MKP activity.

In conclusion, PC12 cells express at least two related MKPs, MKP-1 and MKP-2. The identification of a family of MKPs that are expressed within the same cell suggests distinct roles for each member of this expanding family. Discrimination of the actions of these MKPs may occur through the divergent amino-termini of these proteins. Further studies are required to identify the physiological roles of each member of this unique family of phosphatases in order to gain a better understanding of the mechanisms involved in cellular proliferation, differentiation, and stress.

EXAMPLE 2

Insights into physiological roles of MKP-1 and MKP-2 have come from transient transfection studies where the extracellular signal regulated kinases (ERKs) activation was blocked by MKP overexpression (60, 68, 70, 73). For example, transient expression of MKP-1 and MKP-2 into PC12 cells inhibits ERK-dependent pathways (68). However, transient transfection, which permits transcription from multiple copies of the exogenous plasmid DNA, results in levels of expression that generally exceed those reached during physiological induction of transcription. In contrast to the action of transiently transfected MKPs, physiological induction of endogenous MKP-1 and MKP-2 in PC12 cells following NGF treatment does not correlate with the inactivation of ERKs (68). These observations suggest that the specificity of MKP's actions may depend upon their level of expression as well as other factors. Less robust expression can be achieved using stable expression of transfected genes which requires chromosomal integration and selection and therefore may mimic more closely the levels reached during physiological stimulations. In the study set forth below, we compared the effects of transient and stable expression of transfected MKP-1 and MKP-2 on signaling pathways initiated by extracellular stimuli that activate the ERK signal transduction cascade. We demonstrate that ERK activation and neuronal differentiation are differentially sensitive to MKP expression.

Materials. PC12-GR5 cells were kindly provided by Rae Nishi (Oregon Health Sciences, University, Portland, Oreg.). The Gal4-Elk-1, 5XGal4-E1B-luciferase, and RasV12 plasmids have been described previously (68). The Gal4-c-jun plasmid was a kind of gift from Richard Goodman (Vollum Institute, Portland, Oreg.). C-fos cDNA was kindly provided by Jim Douglas (Amgen, Thousand Oaks, Calif.) and the stromelysin-1 cDNA was provided by Gary Ciment (Oregon Health Sciences University). Agarose-coupled antibodies to JNK1(FL) and ERK1(C16) were from Santa Cruz Biotechnology (Santa Cruz, Calif.). NGF was from Boehringer Mannheim, EGF was from Sigma, Forskolin and PMA were from Calbiochem.

Cell culture. PC12-GR5 cells were grown at 5% $CO_2$ in Dulbecco's modified Eagle's medium (DMEM) containing 5% fetal calf serum, 10% horse serum, and L-glutamine. Prior to drug treatments, the cells were serum starved for 24 h with DMEM alone and subsequently treated with 100 ng/ml NGF, 50 ng/ml EGF, 10 $\mu$M Forskolin, or 100 nM PMA.

Plasmids. Full length MKP-1 cDNA (1.9 kb Hind III-Bam HI fragment) was subcloned into pcDNA3 (Invitrogen) under the cytomegalovirus (CMV) promoter to generate CMV-MKP1. A truncated MKP-2 cDNA fragment containing the entire coding region (2.4 kb Eco RV fragment) was also subcloned into pcDNA3 to generate CMV-MKP2 (68). pcDNA3 contains the neomycin gene driven by the SV40 promoter.

Transient transfections. 60–80% confluent cells were co-transferred using the standard calcium phosphate co-precipitation method (Gibco BRL) with the indicated combinations of the following plasmids: 10 $\mu$g of RSV-$\beta$-galactosidase, 20 $\mu$g of CMV-MKP1, 20 $\mu$g of CMV-MKP2, 10 $\mu$g of RasV12 or 5 $\mu$g of Gal5-Elk-1 and 5 $\mu$g of 5XGa14-E1B-luciferase. In order to determine the transcriptional activation of c-jun, cells were transfected with or without 1 $\mu$g of MEKK and 5 $\mu$g of both Gal4-c-jun and 5XGa14-E1B-luciferase as indicated. The parent vector pcDNA3 was added to each set of transfections to equalize the amount of DNA the cells received. Four hours following transfection, cells were glycerol shocked and allowed to recover in serum containing media overnight. Cells were then starved overnight in supplemented serum free media (N2) which contained DMEM with 5 $\mu$g/ml Insulin, 100 $\mu$g/ml apo-transferrin, 30 $\mu$M Sodium selenite, 100 $\mu$M Putrescine, and 20 nM Progesterone. Cells were then treated with the indicated drugs for 6 hours prior to harvesting. Briefly, cells were washed twice in phosphate buffered saline (PBS), scraped in PBS, spun at low speed to collect cells, and lysed by freeze-thawing three times in 100 mM $K_2PO_4$, pH 7.8. The lysate was spun at high speed and the supernatant was assayed for luciferase activity using a luminometer (AutoLumat LB953).

Histological detection of $\beta$-galactosidase. The expression of $\beta$-galactosidase was used to identify transfectants within the population of differentiating cells. For counting blue cells ($\beta$-galactosidase positive) with neurites, the transfected cells were exposed to NGF for 2 days prior to fixation. PC12 cells were fixed in 2% paraformaldehyde and 0.2% glutaraldehyde for 5 minutes after which cells were washed in PBS and subjected to a $\beta$-galactosidase assay. Cells were exposed to 2 mM $MgCl_2$, 5 mM Ferric cyanide, 5 mM Ferrous cyanide, and 0.1% X-gal in PBS overnight at 37° C.

Transfected cells were identified as those staining and were then counted to determine the percent of blue cells with neurites in each set of transfections. Each set of transfections was done in duplicate and 200 cells were counted for each experimental condition.

Stable transfections. PC12-GR5 cells were seeded at $3\times10^5$ cells per 100 mm plate 48 hours prior to transfection. Cells were transfected with 20 µg of CMV-MKP1 and 20 µg of CMV-MKP2 respectively by calcium phosphate co-precipitation and were exposed to the precipitate for 4 hours. The cells were then glycerol shocked and allowed to recover in complete media. 48 hours later, cells were split and plated in complete media containing 800 µg/ml G418. Stable neomycin-resistant cells were clonally isolated using cloning rings at 3 weeks post-transfection and maintained in media containing 600 µg/ml G418.

RNA Isolation, Riboprobe synthesis, and Northern blot analysis. RNA isolation using RNAzol B and MKP-1 and MKP-2 riboprobe synthesis has been described elsewhere (68). The c-fos transcript was detected by linearizing the 1.3 kb pGEM-c-fos plasmid with Eco RI and using SP6 RNA polymerase for antisense RNA probe synthesis in the presence of $\alpha$-$^{32}$P-UTP (40 µCi/µl). Stromelysin transcripts were detected by linearizing pGEM-TR1 with Hind III and using T7 RNA polymerase to make antisense RNA transcripts. The conditions for Northern blotting using cRNA probes has been described (68). All filters were scanned and quantitated using a Molecular Dynamics PhosphorImager 445SI.

Proliferation Assay. Equal numbers of cells (2000/well) were seeded for all three cell lines (PC12, MKP1.10, and MKP2.3) on 96-well plates. Proliferation was assessed by using the Cell Proliferation ELISA, BrdU kit (Boehringer Mannheim). Briefly, cells were labeled with 10 µM BrdU for 4 hours after which they were fixed directly on the plate. Cells were then incubated with a BrdU-antibody, washed 3 times, and incubated with substrate for 10 minutes prior to addition of the 1M $H_2SO_4$ stop dye. Results were quantized immediately on a ELISA reader at 450 nm. Each day represents an average of six independent wells for each of the three cell lines. Cells were also serum deprived by exposure to N2 media for 2 days prior to stimulation with serum containing media for the days indicated. Again, each day represents an average of six independent wells for each cell line.

ERK immune complex assay. Treated and untreated cells were lysed in a lysis buffer containing 10% Sucrose, 1% NP-40, 20 mM TrisCl pH 8.0, 137 mM NaCl, 10% glycerol, 2 mM EDTA, 1 mM PMSF, 1 µg/ml Leupeptin, 1 mM Sodium Vanadate, and 10 mM Sodium Fluoride. The lysates were spun at low speed to remove nuclei and the supernatant was assayed for ERK activity. 100 µg of total protein (as determined by Bradford Assay) was immunoprecipitated with an agarose-coupled antibody to ERK-1 (C-16) overnight at 4° C. The immunoprecipitated ERK-1 was washed 3 times in lysis buffer and was assayed for kinase activity by incubating with 10 µg myelin basic protein (MBP) and 10 µCi γ-$^{32}$P-ATP in 50 µl of buffer containing 80 mM Hepes pH 7.4, 80 mM $MgCl_2$, 0.1 mM ATP, 2 mM Sodium Vanadate, and 20 mM Sodium Fluoride for 30 minutes at 30° C. Reactions were terminated by the addition of 50 µl of Laemmli sample buffer and analyzed by SDS-PAGE. Quantitations were performed by scanning the gell using a PhosphorImager.

JNK immune complex assay. Treated and untreated cells were lysed in a lysis buffer containing 20 mM Hepes-KOH pH 7.4, 2 mM EGTA, 50 mM β-glycerophosphate, 10% Glycerol, 1% Triton X-100, 1 mM DTT, 1 mM Sodium Vanadate, 0.4 mM PMSF, 0.5 µg/ml Aprotinin, and 0.5 µg/ml Leupeptin. The lysates were spun at low speed to remove nuclei and the supernatant was assayed for JKN activity. 100 µg of total protein (as determined by Bradford Assay) was immunoprecipitated with an agarose-coupled antibody to JNK-1 (FL) overnight at 4° C. The immunoprecipitated JNK-1 was washed 3 times in each of 3 buffers (Lysis buffer, LiCl buffer {500 mM LiCl, 100 mM Tris-HCl pH 7.6, 1 mM DTT, and 0.1% Triton X-100}, and Assay buffer {20 mM MOPS pH 7.2, 10 mM $MgCl_2$, 2 mM EGTA, 1 mM DTT, and 0.1% Triton X-100}) and was assayed for kinase activity by incubating with 3 µg Gst-c-jun and 1 µCi γ-$^{32}$P-ATP in assay buffer for 30 minutes at 30° C. Reactions were terminated by the addition of 50 µl of Laemmli sample buffer and analyzed by SDS-PAGE. Quantitations were performed by scanning the gel using a PhosphorImager.

Morphological determination. Cells were grown on Primaria plates and were serum starved in N2 media for 24 hours (control) and subsequently treated with NGF in N2 media for the days indicated. Cells were washed twice with PBS and fixed in 4% paraformaldehyde and 0.1% glutaraldehyde for 5 minutes after which they were washed in PBS. Cells were photographed at 70× magnification with a Leitz Dialux 22 EB.

RESULTS

Figure 11:
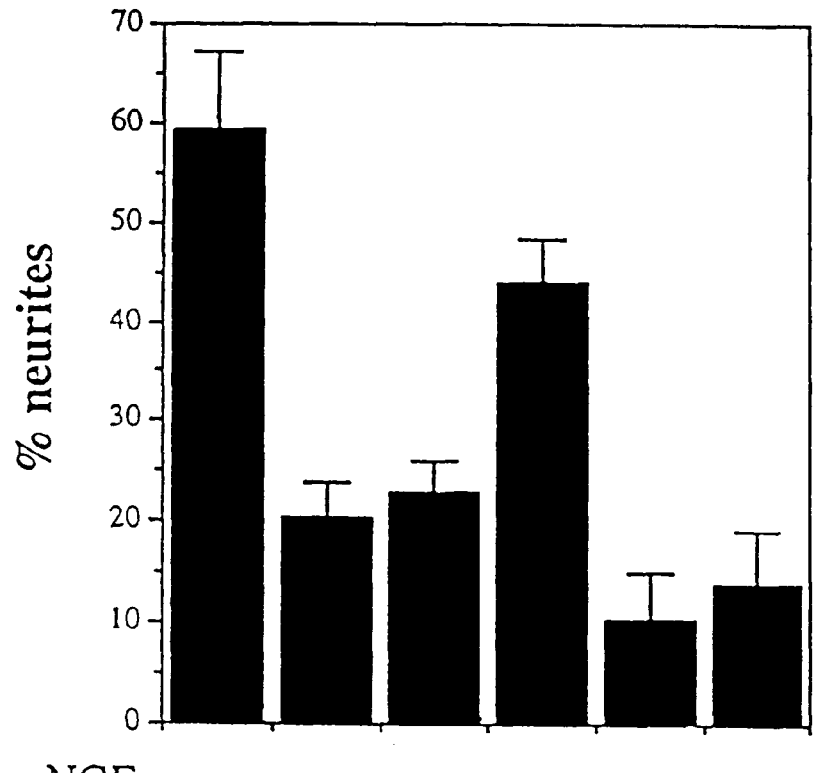
FIG. 11 shows that transient transfection of MKP-1 and MKP-2 inhibits neurite outgrowth. PC12 cells were transfected with the indicated combinations of plasmids and where indicated were also treated with 100 ng/ml NGF for 2 days after transfection. RasV12 transfected cells were also incubated for 2 days after transfection. β-galactosidase assays were performed and blue cells (β-galactosidase positive) were counted. The presented values are an average of four individual counts from separate fields of two independent sets of transfections and are represented as the percentage of blue cells that elaborated neurites.

Transient transfection of MKP-1 and MKP-2 blocked neurite outgrowth in PC12 cells. To compare the action of MKP-1 and MKP-2 in governing cellular differentiation, we transiently transfected PC12 cells with expression vectors carrying the coding regions of MKP-1 and MKP-2 or with the control vector. We also co-transfected a gene encoding β-galactosidase that provided a marker for transfected cells following histological staining for β-galactosidase activity. One set of transfections contained a vector encoding active Ras (RasV12) along with the other plasmids, while the other set was treated with NGF for 48 hours prior to performing the β-galactosidase staining (FIG. 11). Both NGF treated cells and cells receiving the RasV12 plasmid developed neurites in 40–60% of the β-galactosidase positive cells. However, following transient transfection of MKP-1 and MKP-2, only 10–20% of the β-galactosidase positive cells showed neurites (FIG. 11). These results demonstrate that a second member of the MKP family, MKP-2, can inhibit neuronal differentiation when transiently overexpressed, as we have previously shown for MKP-1 (73). In contrast, under more physiological conditions, the induction of endogenous MKP-1 and MKP-2 mRNA expression by NGF does not block neuronal differentiation (68). It is important, therefore, to examine PC12 cells where the overexpression of MKPs is maintained at more physiological levels. Therefore, we have examined stable PC12-derived cell lines that express MKPs to levels that are similar to that achieved following induction of MKPs by physiological agents.

Figure 12A:
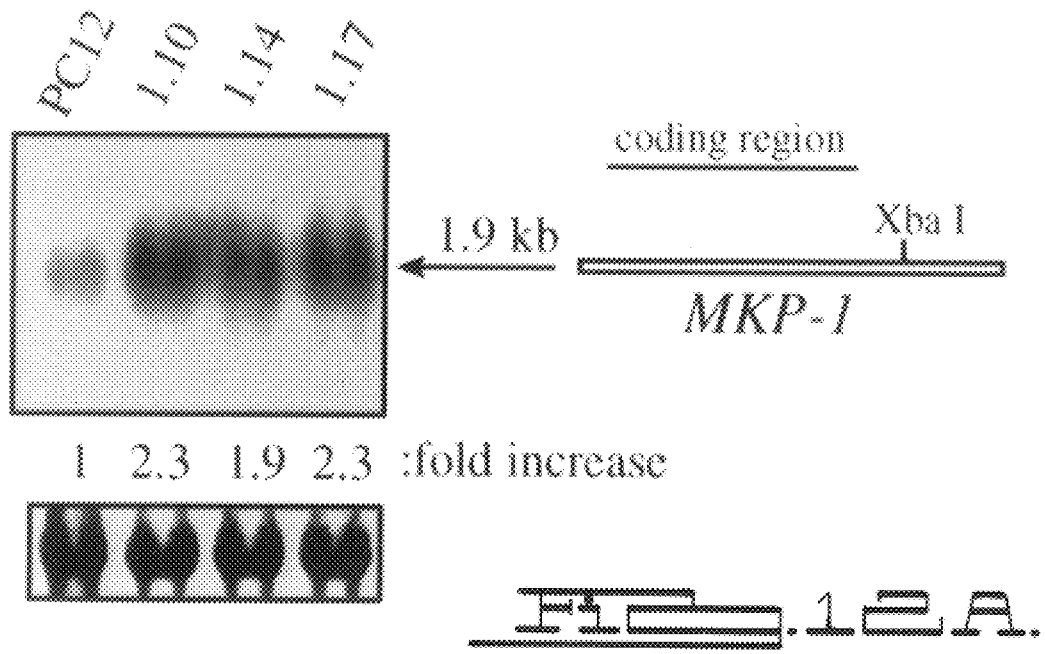
FIGS. 12A and 12B show the identification of PC12 cells stably transfected with MKP-1 or MKP-2 cDNAs. PC12 cells were transfected with CMV-MKP1 or CMV-MKP2 respectively and selected for three weeks in the presence of 800 μg/ml G418. Neomycin resistant cells were clonally isolated and 10 μg of total RNA was used for Northern blot analysis with an MKP-1 specific riboprobe (A) or an MKP-2 specific riboprobe (B). Fold inductions over control untransfected cells are indicated in A. To demonstrate equivalent amount of RNA in each lane, the 18S ribosomal RNA bands are also shown (A and B). The endogenous sizes for MKP-1 (1.9 kb), MKP-2 (6 kb), and the exogenous MKP-2 transgene (2.4 kb) are indicated.
Figure 12B:
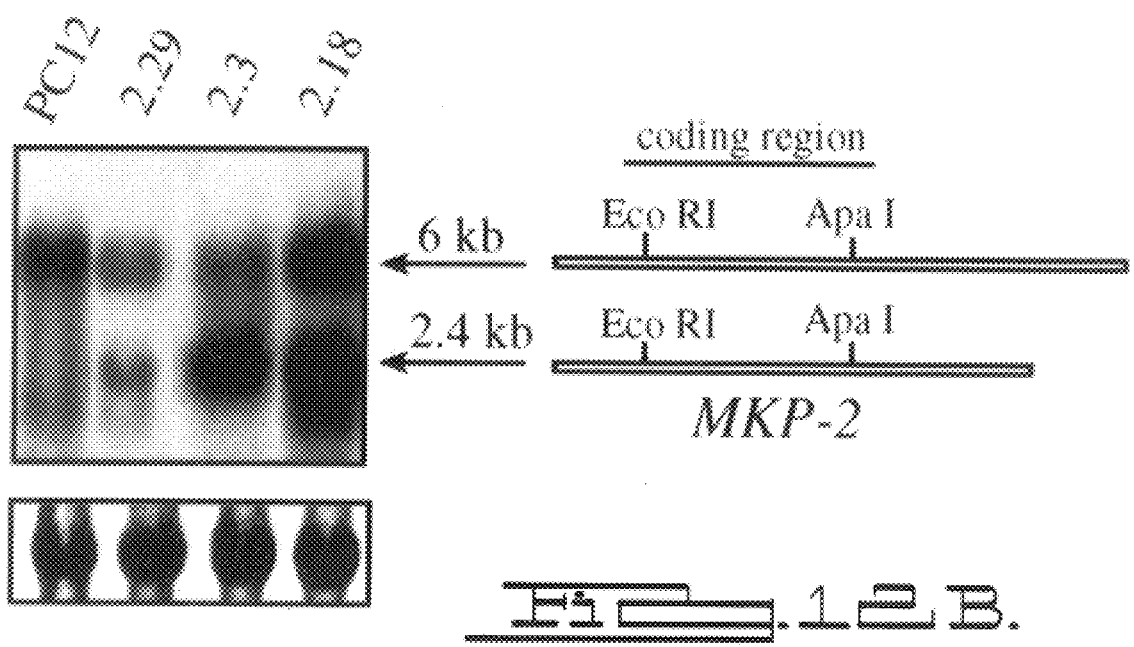

Generation of MKP-1 and MKP-2 overexpressing stable cell lines. To investigate the consequences of limited overexpression of MAP kinase phosphatases, we generated clonal isolates that stably expressed MKPs. PC12 cells were transfected with MKP-1 and MKP-2 cDNAs under the control of the CMV promoter and selected using neomycin. The percentage of neomycin-positive and MKP-1 and MKP-2-positive cells was low. Because the size of the transcribed MKP-1 transgene was identical to the endogenous MKP-1 transcript, positive cell lines were identified by quantitation of Northern blots (FIG. 12A). The MKP-2 transgene was designed to encode a short 2.4 kb transcript lacking most of the long 3' untranslated region that is present in the endogenous transcript. Positive cell lines were identified based on the presence of the additional smaller band by Northern analysis (FIG. 12B). The expression of the transgenes was only 2–3 fold over basal in every positive clone analyzed. This level of expression was similar to levels achieved following induction by NGF and EGF (68). Therefore, these clonal lines provide a model for the action of physiological levels of MKP expression. Two clones (MKP1.10 and MKP2.30 were expanded for initial study. These cells show some morphological differences compared to wild type cells. MKP1.10 cells are smaller and rounder in shape and do not clump. In contrast, MKP2.3 cells although smaller than PC12 cells, exhibit a tendency to clump and are often multinucleated (see below).

Figure 13A:
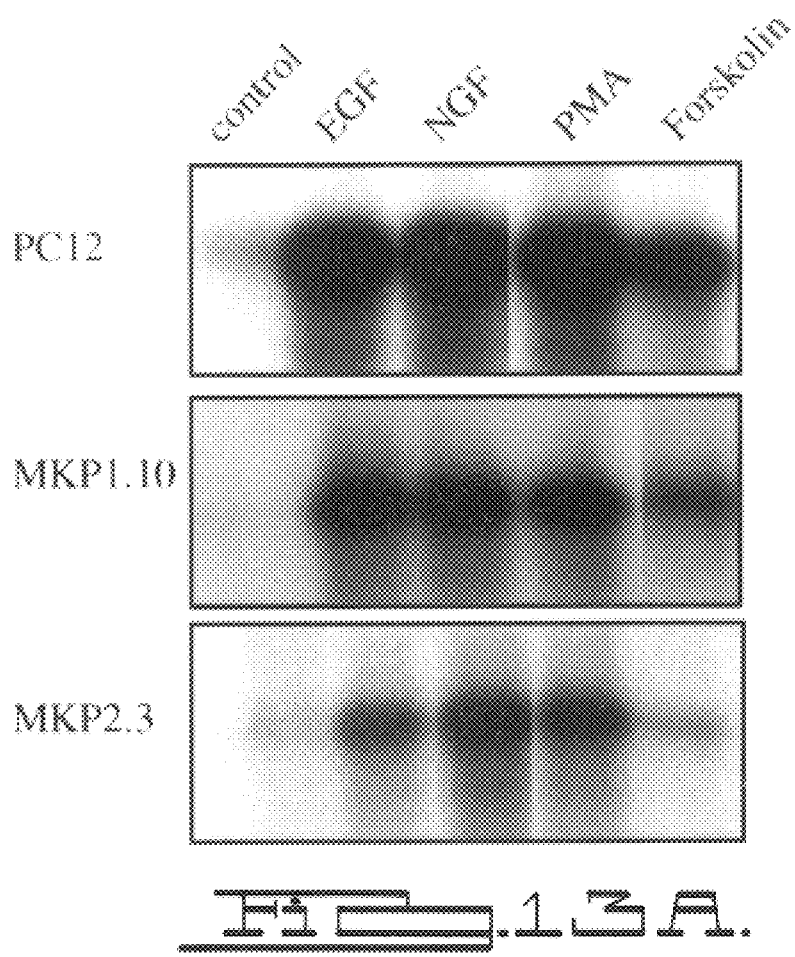
FIGS. 13A and 13B show ERK activation by growth factors, phorbol esters, and hormones is reduced in MKP-1 and MKP-2 overexpressing cells. A. PC12, MKP1.10, and MKP2.3 cells were serum starved for 24 hours and treated for 10 minutes with the indicated drugs. ERK-1 immune complex assays were performed as described using MBP as a substrate. B. Quantitative representation of ERk activity assays from an average of either three independent experiments (PC12) or from two independent experiments (MKP1.10 and MKP2.3). Presented values for all treatments represent fold induction compared with untreated control PC12 cells which were normalized as 1.
Figure 13B:
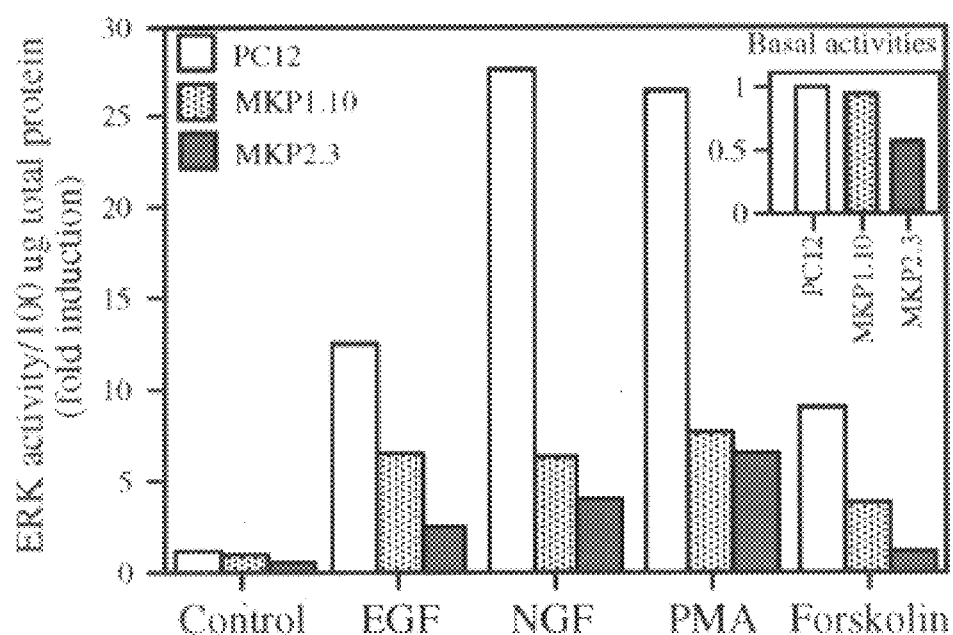

ERK activity is reduced in MKP-1 and MKP-2 overexpressing cells. Growth factor, hormone, and phorbol ester stimulation of PC12 cells has been known to activate the MAP kinase pathway and to stimulate the enzymatic activity of ERK-1 (FIGS. 13A and 13B) (61, 62, 65, 69, 71). We compared the enzymatic activity of ERK-1, in wild type cells and in MKP overexpressing cells treated with these agents. PC12 cells treated for 10 minutes with mitogenic agents such as EGF, differentiating agents such as NGF and forskolin, and the tumor promoter phorbol 12-myristate 132-acetate (PMA), produce a robust activation of ERK-1 as measured by an immune complex activity assay (FIG. 13A). MKP-1 and MKP-2 overexpressing clones were then treated with the same agents for the identical times. Both MKP1.10 and MKP2.3 cells lines showed a dramatic reduction in the ability of growth factors and hormones to activate ERK-1 (FIG. 13A). Additional positive clones were also analyzed and showed similar results (data not shown). Quantitation of the immune complex assays shows that the modest overexpression of MKP-1 and MKP-2 mRNA in PC12 cells inhibited growth factor and hormoneinduced activation of ERKs 80–90% in MKP2.3 cells and 50–80% in MKP1.0 cells compared to the fold activation seen.in wild type PC12 cells (FIG. 13B). The basal ERK activity also appeared to be lower in these MKP overexpression cells as compared to wild type cells (FIG. 13B), insert).

MKPs have been shown to dephosphorylate other MAP kinases like the JNKs (56, 64). Therefore, we examined the stimulation of JNK activity by NGF, EGF, forskolin, and PMA, as well. IN wild type PC12 cells, minimal stimulation of JNK activity was seen only by EGF (1.6-fold) (FIG. 14A). In MKP2.3 cells, both basal and EGF stimulated levels were only slightly reduced. EGF appears to be a more potent activator of ERKs (12.5-fold) rather than the JNKs (1.6-fold). Therefore, following stimulation by growth factors (EGF and NGF) and hormones (forskolin), JNKs were not activated significantly in either wild type or MKP2.3 cells. In contrast, JNK activity following PMA treatment in MKP2.3 cells was slightly higher than in wild type cells. UV light, a stimulator of JNK activity, resulted in a 3–4 fold induction over control non-irradiated PC12 cells which was similar to the fold induction observed by others (64). This fold induction of JNK activation by UV light was not reduced in both the MKP1.10 and MKP2.3 cells (data not shown). We also examined the ability of MKP2.3 cells to inhibit transcriptional activation of c-jun. Cells were transfected with or without the JNK activator, MEKK, and the chimeric reporter genes Gal4-c-jun and 5XGal4-E1B-luciferase (58). MEKK has been shown to activate c-jun through its actions on JNKs (67). MEKK activated JNKs to high levels as measured by the activation of c-jun-dependent luciferase activity (FIG. 14B). The c-jun activation stimulated by MEKK was not altered in MKP2.3 cells (FIG. 14B). These results demonstrate that the agents examined in this study preferentially activate ERKs rather than the JNKs and that the activated ERKs, to not JNKs, are the primary targets of MKP action in these cells. Therefore, we used these cells as a model system to examine the consequences of diminished ERK activation following MKP overexpression on signaling pathways via these agents.

Figure 15A:
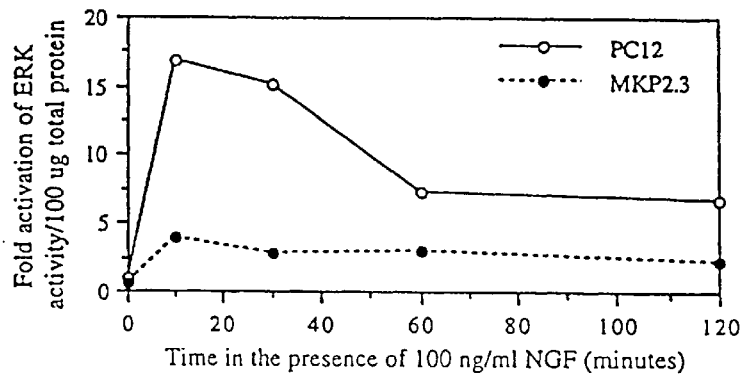
FIGS. 15A and 15B shows the comparison of the kinetics of ERK activation by growth factors in PC12 and MKP2.3 cells. PC12 and MKP2.3 cells were serum starved for 24 hours and treated with NGF (A) or EGF (B) for the indicated times. ERK-1 immune complex assays were performed and quantitated as described. Values for each treatment represent fold induction compared to untreated PC12 cells which were normalized as 1.
Figure 15B:
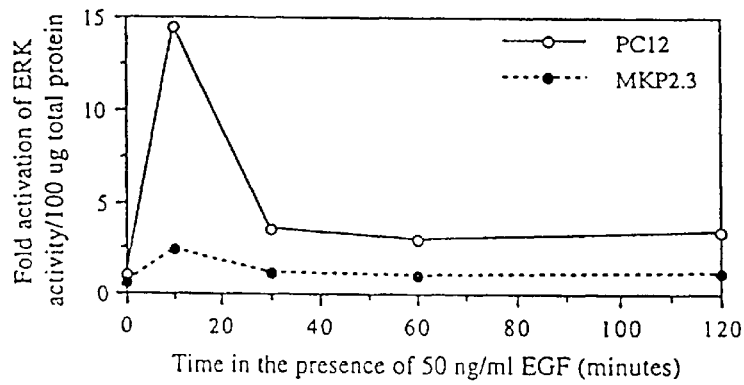

Both the duration and magnitude of ERK activation have been proposed to dictate physiological response to growth factors. Therefore, we examined the kinetics of ERK activation in MKP overexpression cells. We treated PC12 and MKP2.3 cells with NGF and EGF for the indicated times and performed immune complex assays with the ERK-1 antibody. The results were quantitated and showed that the magnitude of ERK activity by both NGF and EGF was severely blunted in MKP2.3 cells. However, the kinetics of the activation profile remained similar (FIGS. 15A and 15B). The effect of this reduction of ERK activation on the physiological response of these cells to growth factor stimulation was subsequently addressed.

Figure 16:
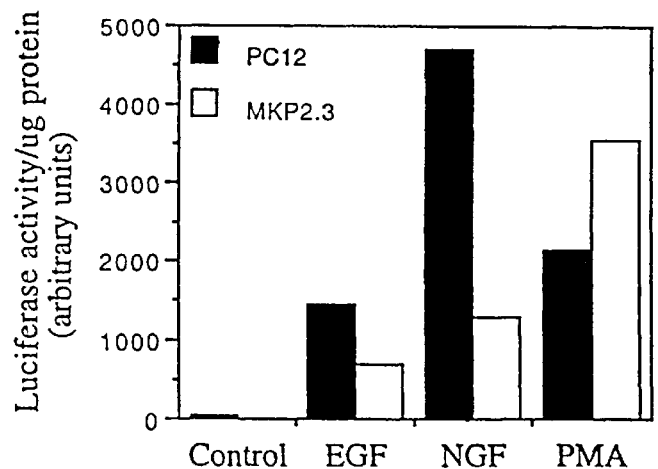
FIG. 16 shows the Elk-1 independent transcription of growth factors is reduced in MKP2.3 cells. PC12 and MKP2.3 cells were transiently transfected with Gal4-Elk-1 and 5XGal4-E1B-luciferase and were treated with the indicated drugs for 6 hours. Control represents transfected cells that were not subjected to any drug treatments. The absolute luciferase activity was then normalized to amount of protein within each lysate and the presented values are the mean of three independent experiments. Note that the basal luciferase activity in MKP2.3 control cells were undetectable.

MKP overexpression cells exhibit reduced activation of ERK-responsive transcription. In order to determine if the MKP-induced reduction in ERK-activation by growth factors and other agents led to changes in gene expression, we compared the ability of MKP overexpression cells to activate transcription of an ERK-dependent gene through the transcriptional activator, Elk-1. Several studies have shown that ERK phosphorylation sites in the carboxyl terminal transcriptional activation domain of Elk-1 are sufficient to allow transcription response to growth factors (63). Cells ere transiently transfected with the chimeric reporter genes Gal4-Elk-1 and 5XGal4-E1B-luciferase and the next day were treated with EGF or NGF for 6 hours prior to harvesting and performing luciferase assays. These agents are thought to activate Elk-1 through their action on ERKs. The physiological activation of ERKs result in increased luciferase activity (FIG. 16). The activation of Elk-1 transcription activational activity by the ERK cascade stimulators (EGF and NGF) was reduced in MKP2.3 cells. Although Elk-1 can be activated by JNKs as well as ERKs (72), neither agent activated JNKs significantly in either wild type or MKP2.3 cells (FIGS. 14A and 14B). Therefore, Elk-1 activation by these agents reflects ERK activation rather than JNK activation. WE conclude that the reduced EGF and NGF-induced ERK activity in these cells was responsible for the reduction in ERK-dependent gene expression. Although PMA-induced ERK activation was inhibited in MKP2.3 cells (FIGS. 13A and 13B), this did not result in a reduction of Elk-1 induced transcription (FIGS. 16A and 16B). Since Elk-1 can also be activated by JNKs (72), the increased Elk-1 induced transcription by PMA in MKP2.3 cells may be due to the increase in JNK activation seen following PMA treatment of these cells (FIG. 14A).

Figure 17:
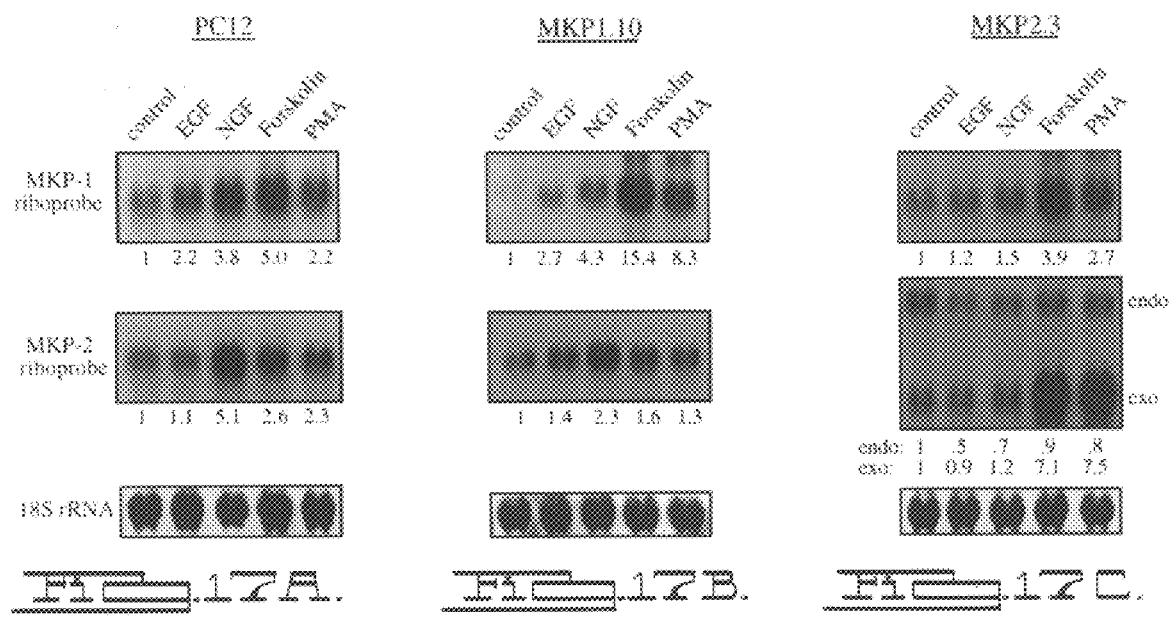
FIGS. 17A, 17B and 17C show the regulation of MKP-1 and MKP-2 mRNA expression. PC12 (panel A), MKP1.10 (panel B), and MKP2.3 (panel C) cells were serum starved for 24 hours (control) or treated with the indicated drugs for 30 minutes prior to isolation of total RNA. 10 μg of total RNA from each treatment were analyzed by Northern blot analysis using a MKP-1 specific probe as indicated. The filter was stripped and re-probed with a MKP-2 specific riboprobe as indicated. To demonstrate equivalent amount of RNA in each lane, the 18S ribosomal RNA bands are also shown. The filter was scanned and quantitated using a Phosphorlmager and the results represent a fold induction over the control untreated cells.

Regulation of endogenous MKP-1 and MKP-2 transcription in MKP overexpressing cells. MKP-1 mRNA is undetectable in quiescent fibroblasts (55). In the wild type PC12 cell line used in this study, serum starvation does not result in loss of MKP-1 and MKP-2 expression (FIG. 17A), suggesting that the basal levels of MKP expression are not dependent on serum factors in these cells. However, stimulation of these serum-starved cells with EGF, NGF, forskolin, and PMA resulted in a modest increase in MKP-1 and MKP-2 mRNA (FIG. 17A). NGF and forskolin were the strongest activators of MKP-1 and MKP-2 RNA (FIG. 17A). These agents also produced a sustained activation of ERKs suggesting that the transient MKP induction by these agents does no inhibit activation (73).

To assess the role of ERKs in the regulation of MKP mRNAs, we compared the induction of MKP-1 and MKP-2 in wild type cells to those seen in both MKP overexpressing cells line s (where ERK activation by these agents is reduced significantly) (FIGS. 13A and 13B). The induction of MKP-2 mRNA by NGF, forskolin, and PMA in the MKP1.10 cells was diminished compared to wild type cells (FIG. 17B). Because the MKP-1 transgene encodes an RNA of the same size as the endogenous transcript, the effect of these agents on the endogenous MKP-1 gene in MKP1.10 cells could not be distinguished. The robust induction of both MKP-1 and MKP-2 transgenes by forskolin and PMA in MKP overexpressing cells may be due to the presence of cAMP/PMA response elements present with the CMV promoter that was used to direct the expression of the MKP transgenes. This was most clearly seen in the transgene-specific MKP-2 band (FIG. 17C).

In cells overexpressing MKP-2, the size of the exogenous transgene was distinguishable from the endogenous MKP-2 transcript (FIG. 17C) making it possible to examine the regulation of the endogenous MKP-2 gene directly in MKP2.3 cells. In these cells, the induction of endogenous MKP-1 mRNA by EGF, NGF, and forskolin but not PMA was diminished compared to wild type cells. The induction of endogenous MKP-2 mRNA in MKP2.3 cells was more substantially reduced by EGF, NGF, forskolin, and by PMA as well (FIG. 17C). Again, the larger induction of exogenous MKP-2 by forskolin and PMA bay be due to the ability of these agents to activate the CMV promoter. Taken together, these results identify an ERK-dependent component to the regulation of both MKP-1 and MKP-2 mRNA expression. The induction of endogenous MKP-2 mRNA by agents that activate ERKs was more severely blunted in MKP-overexpressing cells, suggesting that the induction of MKP-2 mRNA may be more dependent on ERK activity than MKP-1.

Figure 18:
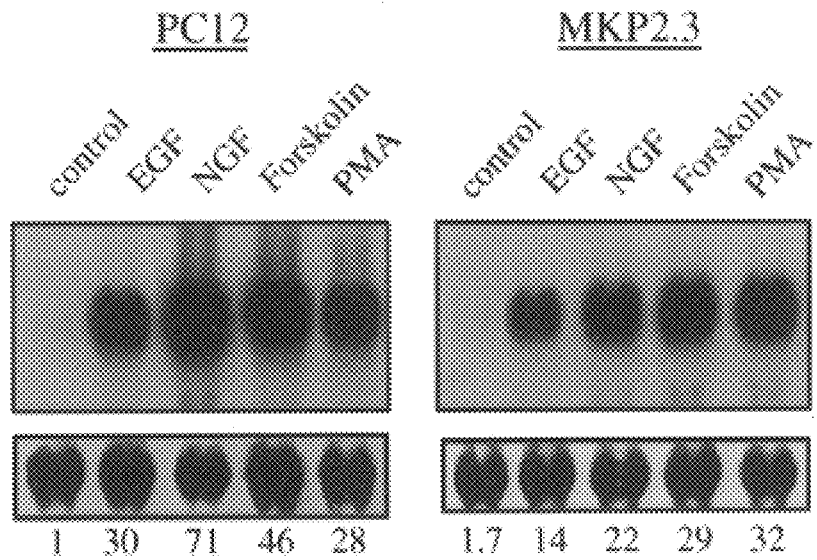
FIG. 18 shows the regulation of fos mRNA expression. PC12 and MKP2.3 cells were serum starved for 24 hours (control) or treated with the indicated drugs for 30 minutes prior to RNA isolation. 10 μg of total RNA was analyzed by Norhern blot analysis using a fos riboprobe. To demonstrate equivalent amount of RNA in each lane, the 18S ribosomal RNA bands are also shown. As both filters were incubated with the same riboprobe preparation, the presented numbers represent fold induction over PC12 control cells, arbitrarily defined as unity.

Effect of MKP overexpression on the immediate early gene, c-fos. Transient transfection of MKP-1 has been shown to reduce serum-stimulated, ERK-dependent activity of the c-fos promoter (54). Since ERK activation by growth factors and other agents was substantially reduced in the MKP2.3 cell line, the requirement of ERK activation in c-fos regulation was examined. WE assayed the expression of the immediate early gene, c-fos, 30 minutes following drug treatment. As compared to wild type PC12 cells, induced c-fos expression by NGF, EGF, and forskolin was reduced in MKP2.3 cells (FIG. 18). Modest overexpression of MKP-2, therefore, is partially able to block the signal-induced overexpression of the immediate early gene, c-fos, by multiple activators of the MAP kinase cascade. In contrast, PMA-induced expression of c-fos was not reduced in these cells (FIG. 18). This effect of PMA may be related to the paradoxical increase in JNK activation following PMA-stimulation of these cells as compared to wild type cells.

Figure 19:
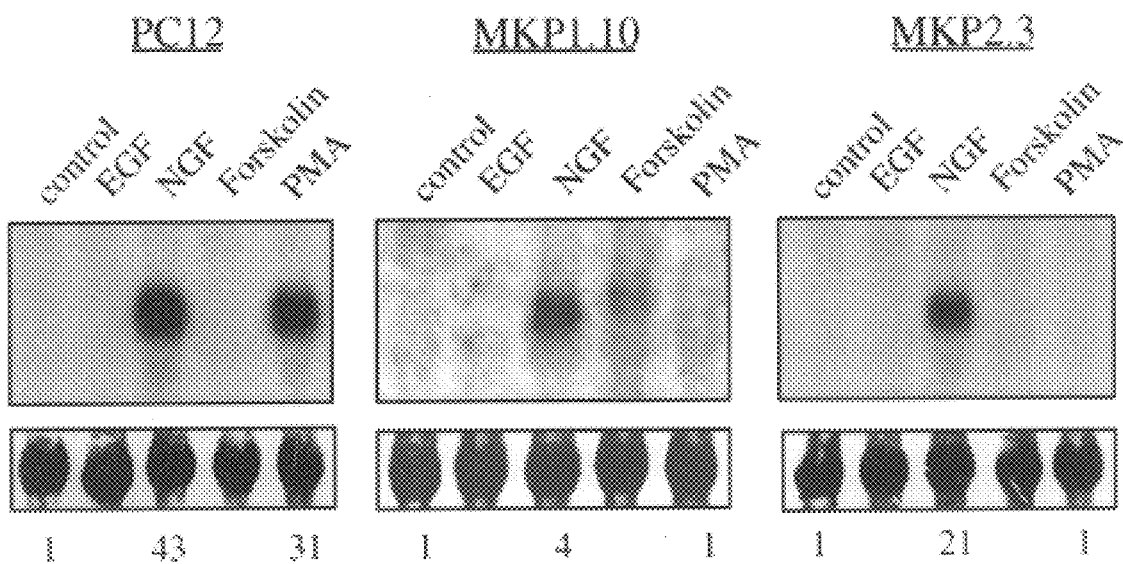
FIG. 19 shows the regulation of stromelysin mRNA expression. PC12 and MKP2.3 cells were serum starved for 24 hours (control) or treated with the indicated drugs for 24 hours prior to RNA isolation. 10 μg of total RNA was analyzed by Northern blot analysis using a stromelysin riboprobe. The 18S ribosomal RNA bands are also shown to demonstrate equivalent amounts of RNA in each lane. The presented numbers (only indicated for agents that induced expression of stromelysin) represent fold induction over the control cells that were normalized as 1.

Effect of MKP-1 and MKP-2 overexpression on the late gene, stromelysin-1 (transin). Stromelysin-1 (Transin) is a late gene that is induced in wild type PC12 cells upon treatment with NGF and PMA (FIG. 19) and its expression is associated with neuronal differentiation (59). Because stromelysin may be regulated by ERK-dependent pathways (73), we analyzed the expression of stromelysin in these cells. Stromelysin induction by NGF was almost completely locked in MKP1.10 cells and was partially blocked in MKP2.3 cells (FIG. 19). The induction of stromelysin was completely inhibited by PMA in both the MKP1.10 and MKP2.3 cells. Identical results were achieved using multiple clonal isolates of MKP overexpressing cells (data not shown). Therefore, reduction of ERK activity by these agents was associated with inhibition of the expression of the late gene stromelysin.

Figure 20A:
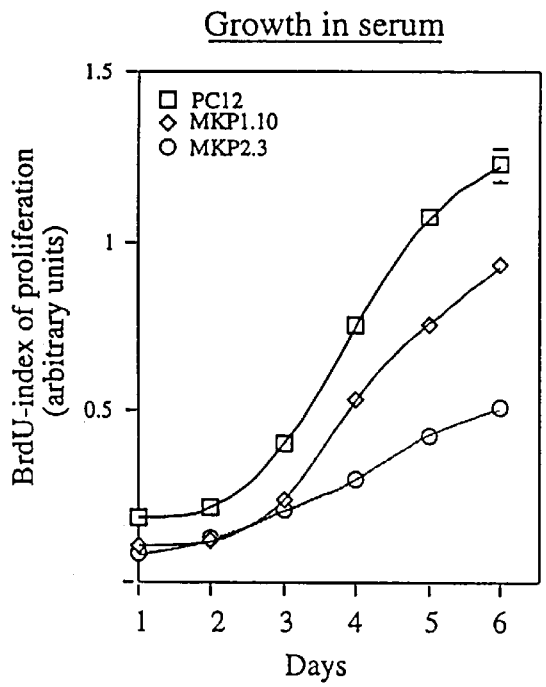
FIGS. 20A and 20B show the comparison of the rate of proliferation between PC12, MKP1.10, and MKP2.3 cells. PC12, MKP1.10, and MKP2.3 cells were seeded equally and analyzed for growth rates using BrdU incorporation as an index of proliferation. A. The growth rate was determined in cells growing in serum containing media for a period up to 6 days after plating. Each value is represented as the mean+/−standard error of six independent experiments. B. PC12, MKP1.10, and MKP2.3 cells were seeded at equal density and then serum starved for 2 days. Serum containing media was then added and the cells were analyzed at the indicated days. Again, each value is represented as the mean+/−standard error of six independent experiments.
Figure 20B:
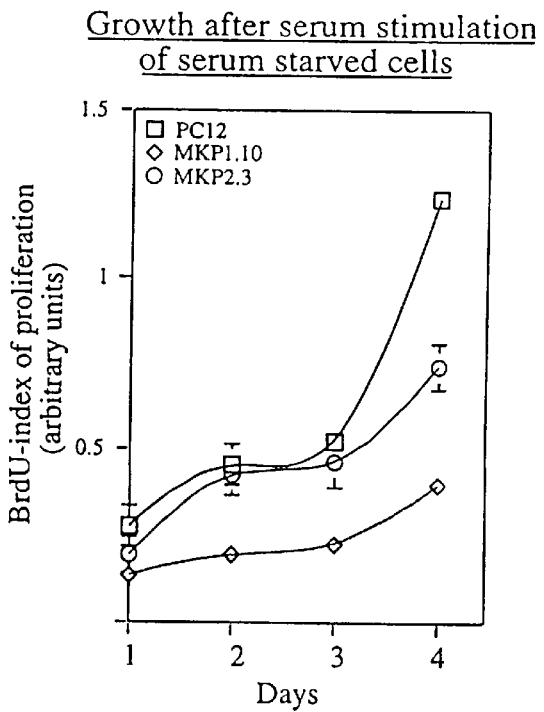

Effect of MKP-1 and MKP-2 overexpression on proliferation and differentiation. Previous reports suggest that the sustained activation of ERKs by NGF is required for PC12 cell differentiation whereas the transient activation of ERKs by EGF is required for proliferation (57, 66). In order to examine the biological consequences of MKP overexpression and reduced growth factor-inducible ERK activation, we measured the proliferation rate of MKP1.10 and MKP2.3 cells. The proliferation rate of parental PC 12 cells growing in serum was higher than that of MKP1.10 and MKP2.3 cells (FIG. 20A). MKP2.3 cells had the slowest rate of proliferation. When the cells were partially synchronized by serum starvation for 2 days and then stimulated with serum, both MKP1.10 and MKP 2.3 cells ere delayed in their entry into the cell cycle (FIG. 20B). Flow cytometric analysis on the three cell lines confirmed these results with MKP1.10 and MKP2.3 cell lines showing a decrease in the percent of cells in S phase compared to wild type cells (data not shown). These results suggest that the reduced growth factor-stimulated ERK activity is associated with a reduction in proliferation in both MKP-1 and MKP-2 overexpressing cells.

Figure 21:
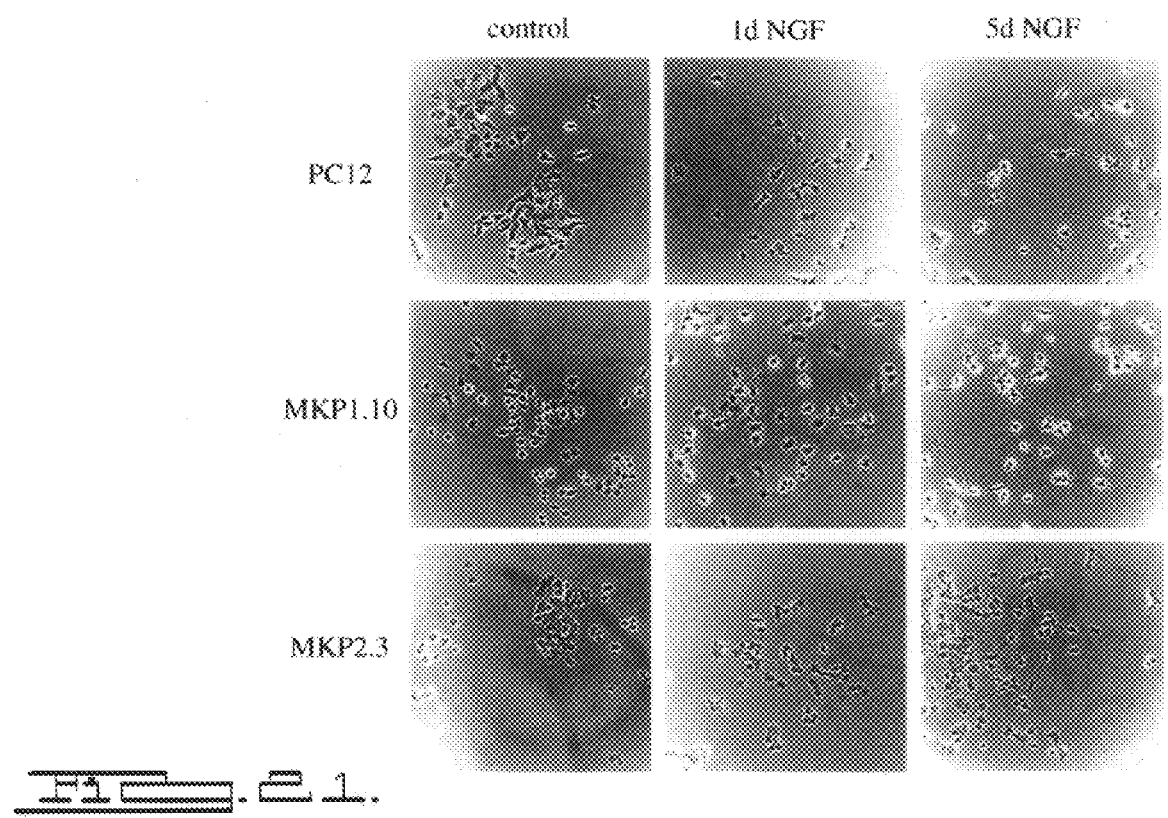
FIG. 21 shows the phase contrast micrographs of morphologically differentiated PC12, MKP1.10, and MKP2.3 cells. PC12, MKP1.10, and MKP2.3 cells were serum starved for 24 hours (control) or were treated with NGF for the indicated days before fixation. Magnification 77×.

We next examined the ability of NGF to induce differentiation in the MKP overexpressing cells. Despite the severely blunted response od MKP1.10 and MKP2.3 cells to ERK activation by NGF, these cells were able to extend neuritic process similar to their parental cell line (FIG. 21). The time course of this differentiative response in MKP overexpression cells was similar to wild type cells (FIG. 21). Additional MKP overexpressing clones were also treated with NGF and similar results were obtained (data not shown). These results suggest that high levels of sustained ERK activity are not absolutely required for morphological differentiation.

EXAMPLE 3

As discussed above, the mitogen-activated protein kinase cascade mediates signals that govern both cell growth and differentiation. The MAP kinases initially included only the extracellular signal regulated kinases (ERKs) which respond to mitogenic signals. However, another pathway is known to respond to a variety of cellular stresses by activating a related family of MAP kinases, called stress-activated protein kinases (SAP kinases) or jun N-terminal protein kinases (JNKs) (74). At least two JNKs, JNK-1 (81) and JNK-2 (75), response to a variety of Ras-dependent and Ras-independent signals to phosphorylate the proto-oncogene c-jun (74, 75, 80, 82) and Elk-1 (83). The phosphorylation of c-jun is associated with growth arrest and stimulation of apoptosis (75–78). Because MAP kinase activation and inactivation is believed to be regulated by MKP-1 and MKP-2 of the present invention, a study was performed that demonstrated that JNK-mediated signaling pathways induce apoptosis in both neuronal and fibroblast cells and that this can be partially reversed by MKPs through a mechanism that is independent of their action on ERKs. Thus, the MKP-2 of the present invention may play a critical role in determining cell fate by selective regulation of mitogenic and stress-activated pathways, e.g., inhibiting apoptosis in response to activation by growth factors on oncogenes.

Based on the foregoing, it will be appreciated that the MKP-2 of the present invention and inhibitors thereto, may be used in therapeutic applications such as cancer therapy. Expression of MKPs in human tumors including prostate, breast, colon, lung and bladder, function to direct oncogenic signals into a proliferative pathway away from apoptosis. The use of MKP inhibitors such as an inhibitor of the MKP-2 of the present invention, will selectively act on tumor cells to redirect the oncogenic signal into apoptopic pathways. It will be appreciated that such novel chemotherapeutics may be combined with current non-surgical treatment for human cancers including radiation and chemotherapy, both of which are stimulators of the stress-activated protein kinase cascade (79, 85) that kill tumor cells by triggering apoptosis (86). Moreover, because apoptosis in neuronal cells contributes to the morbidity associated with neurodegenerative diseases, stroke and Alzheimer's dementia (84), the MKP-2 of the present invention may be used in the development of novel therapeutic strategies for neurodegenerative diseases as well.

While the preferred embodiment of the invention has been illustrated and described, it will be appreciated that various changes can be made therein without departing from the spirit and scope of the invention.

All publications cited herein are incorporated by reference to the same extent as if each individual publication was specifically and individually indicated to be incorporated by reference. The invention now being fully described, it will be apparent to one of ordinary skill in the art that many changes and modifications can be made thereto without departing from the spirit or scope of the invention.

REFERENCES

1. Pagés, G., Lenormand, P., L'Allenmain, G., Chambard, J.-C., Meloche, S., and Pouysségur, J. (1993) *Proc. Nati. Acad. Sci. U.S.A.* 90, 8319–8323.
2. Blenis, J. (1993) *Proc. Natl. Acad. Sci. U.S.A.* 90, 5889–5892.
3. Cowley, S., Paterson, H., Kemp, P., and Marshall, C. J. (1994) *Cell* 77, 841–852.
4. Chao, M. V. (1992) *Cell* 68, 995–997.
5. Nguyen, T. T., Scimeca, J.-C., Filloux, C., Peraldi, P., Carpentier, J.-L., and VanObberghen, E. (1993) *J. Biol. Chem.* 268, 9803–9810.
6. Wood, K. W., Sarnecki, C., Roberts, T. M., and Blenis, K. (1992) *Cell* 68, 1041–150.
7. Alema, S., Casalbore, P., Agostini, E., and Tato, F. (1985) *Nature* 316, 557–559.
8. Thomas, S. M., DeMarco, M., D'Arcangelo, G., Halegoua, S., and Brugge, J. S. (1992) *Cell* 68,1031–1040.
9. Thomas, S. M., Hayes, M., D'Arcangelo, G., Armstrong, R. C., Meyer, B. D., Zilberstein, A., Brugge, J. S., and Halegoua, S. (1991) *Mol. Cell. Biol.* 11, 4739–4750.
10. Lloyd, E. D., and Wooten, M. W. (1992) *J. Nerochem.* 59,1099–1109.
11. Crews, C. M., and Erikson, R. L. (1993) *Cell* 74, 215–217.
12. Zheng, C.-F., and Guan, K.-L. (1993)*J. Biol. Chem.* 268, 23933–23939.
13. Sun, H., Charles, C. H., Lau, L. F., and Tonks, N. K. (1993) *Cell* 75, 487–493.
14. Allessi, D. R., Smythe, C., and Keyse, S. M. (1993) *Oncogene* 8, 2015–2020.
15. Ward, Y., Gupta, S., Jensen, P., Wartmann, M., Davis, R. J., and Kelly, K. (1994) *Nature* 367, 651–654.
16. Zheng, C.-F., and Guan, K.-L. (1993)*J. Biol. Chem.* 268, 16116–16119.
17. Traverse, S., Gomez, N., Paterson, H., Marshall, C., and Cohen, P. (1992) *Biochem. J.* 288, 351–355.
18. Kumagai, A., and Dunphy, W. G. (1992) *Cell* 70, 139–151.
19. Charles, C. H., Abler, A. S., and Lau, L. C. (1992) *Oncogene* 7, 187–190.
20. Doi, K., Garner, A., Ammerer, G., Errede, B., Shinkawa, H., Sugimoto, K., and Matsumoto, K. (1994)*EMBO J*. 13, 61–70.
21. Guan, K., Haun, R. S., Watson, S. J., Geahlen, R. L., and Dixon, J. E. (1990) *Proc. Natl. Acad. Sci. U.S.A.* 87, 1501–1505.
22. Keyse, S. M., and Emslie, E. A. (1992) *Nature* 359, 644–647.
23. Rohan, P. J., Davis, P., Moskaluk, C. A., Kearns, M., Krutzch, H., Siebenlist, and Kelly, K. (1993) *Science* 259, 1763–1766.
24. Ishibashi, T., Bottaro, D. P., Michieli, P., Kelley, C. A., and Aaronson, S. A. (1994) *J. Biol. Chem.* 269, 29897–29902.
25. Sun, H., Tonks, N. K., and Bar-Sagi, D. (1994) *Science* 266, 285–288.
26. Noguchi, T., Metz, R., Chen, L., Mattéi, M.-G., Carrasco, D., and Bravo, R. (1993) *Mol. Cell. Biol.* 13, 5195–5205.
27. Boulton, T. G., Nye, S. H., Robbins, D. J., Ip, N. Y., Radziejewska, E., Morgenbesser, S. D., DePinho, R. A., N, P., Cobb, M. H., and Yancopoulos, G. D. (1991) *Cell* 65, 663–675.
28. Greene, L. A., and Tischler, A. S. (1982) *Adv. Cell. Neurobiol.* 3, 373–414.
29. Thomas, K. R., Musci, T. S., Neumann, P. E., and Capecchi, M. R. (1991) *Cell* 67, 969–976.
30. Druker, B., Okuda, K., Matulonis, U., Saigia, R., Roberts, T., and Griffin, J. D. (1992) *Blood* 79, 2215–2220.
31. Sanger, F., Milken, S., and Coulson, A. R. (1977) *Proc. Natl. Acad. Sci. U.S.A.* 74, 5463–5467.
32. Misra-Press, A., Cooke, N. E., and Liebhaber, S. A. (1994) *J. Biol. Chem.* 269, 23220–23229.
33. Arriza, J. L., Stoler, M. H., and Angerer, R. C. (1988) *Neuron* 1, 887–900.
34. Bruder, J. T., Heidecker, G., and Rapp, U. R. (1992) *Genes & Develop.* 6, 545–556.
35. Howley, P. M., Sarver, N., and Law, M. F. (1983) *Methods Enzymol.* 101, 387402.
36. Luehrsen, K. R., Wet, J. R. d., and Walbot, V. (1992) *Methods Enzymol.* 216, 397–414.
37. Bradford, M. M. (1976) *Anal. Biochem.* 72, 248–254.
38. Stork, P., Misra-Press, A., and Pan, M-G. (1995) Receptor-coupled phosphatases. Methods Neurosci. Academic Press, Orlando, Fla. (in press).
39. Bialojan, C., and Takai, A. (1988) *Biochem J*. 256, 283–290.
40. MacKintosh, C., Beattie, K. A., Klumpp, S., Cohen, P., and Codd, G. A. (1990) *FEBS Lett.* 264,187–192.
41. Marais, R., Wynne, J., and Treisman, R. (1993) *Cell* 73, 381–393.
42. Kwak, S. P., Hakes, D. M., Martell, K. J., and Dixon, J. E. (1994) *J. Biol. Chem.* 269, 3596–604.
43. Shaw, G. and Kamen, R. (1986) *Cell* 46, 659–667.
44. Fiore, R. S., Bayer, V. E., Pelech, S. L., Posada, J., Cooper, J. A., and Baraban, J. M. (1993) *Neurosci* 55, 463–472.
45. Boulton, T. G., Nye, S. H., Robbins, D. J., Ip, N. Y., Radziejewska, E., Morgenbesser, S. D., DePinho, R. A., Panayotatos, N., Cobb, M. H., and Yancopoulos, G. D. (1991) *Cell* 65, 663–675.
46. Bading, H., and Greenberg, M. E. (1991) *Science* 253, 912–914.

47. Friedman, L. K., Pellegrini-Giampietro, D. E., Sperber, E. F., Bennett, M. V. L., Moshé, S. L., and Zukin, R. S. (1994) *J. Neurosci.* 14, 2697–2707.
48. Pennypacker, K. R., Walczak, D., Thai, L., Fannin, R., Mason, E., Douglass, J., and Hong, J. S. (1993) *J. Neurochem.* 60, 204–211.
49. Derijard, B., Hibi, M., Wu, I.-H., Barrett, T., Su, B., Deng, T., Karin, M., and Davis, R. J. (1994) *Cell* 76, 1025–1037.
50. Loeb, D. M., Stephens, T. M., Copeland, T., Kaplan, D. R., and Greene, L. A. (1994) *J. Biol. Chem.* 269, 8901–8910.
51. Young, S. W., Dickens, M., and Tavare, J. M. (1994) *FEBS Lett.* 338, 212–216.
52. Traverse, S., Seedorf, K., Paterson, H., Marshall, C. H., Cohen, P., and Ullrich, A. (1994) *Curr. Biol.* 4, 694–701.
53. Wu, J., Lau, L. F., and Sturgill, T. W. (1994) *FEBS Lett.* 353, 9–12.
54. Brondello, J. M., McKenzie, F. R., Sun, H., Tonks, N. K., and Pouyssegur, J. (1995) *Oncogene* 10, 1895–1904.
55. Charles, C. H., Abler, A. S., and Lau, L. F. (1992) *Oncogene* 7,187–190.
56. Chu, Y., Solski, P. A., Khosravi-Far, R., Der, C. J. and Kelly, K. (1996) *J. Biol. Chem.* 11, 6497–6501.
57. Cowley, S., Paterson, H., Kemp, P. and Marshall, C. J. (1994) *Cell* 77, 841–852.
58. Derijard, B., Hibi, M., Wu, I. H., Barrett, T., Su, B. Deng, T., Karin, M. and Davis, R. J. (1994) *Cell* 76, 1025–1037.
59. Fillmore, H. L., Mainardi, C. L. and Hasty, K. A. (1992) *J. Neurosci Res.* 31, 662–669.
60. Fukuda, M., Gotoh, Y., Tachibana, T., Dell, K., Hattori, S., Yoneda, Y. and Nishida, E. *Oncogene* 11, 239–344.
61. Hill, C. S. and Treisman, R. (1995) *Cell* 80, 199–211.
62. Jaiswal, R. K., Murphy, M. B. and Landreth, G. E. (1993) *J. Biol. Chem.* 268, 7055–7063.
63. Janknecht, R., Ernst, W. H., Pingound, V. and Nordheim, A. (1993) *EMBO J.* 12, 5097–5104.
64. Liu, Y., M. Gorospe, C. Yang, and N. J. Holbrook (1995) *J. Biol. Chem.* 270, 8377–8380.
65. Lloyd, E. D., and M. W. Wooten (1992) *J. Nerochem.* 59,1099–1109.
66. Marshall, C. J. (1995) *Cell* 80, 179–185.
67. Minden, A., A. Lin, T. Smeal, B. Derijard, M. Cobb, R. Davis, and M. Karin (1994) *Mol. Cell. Biol.* 14, 6683–6688.
68. Misra-Press, A., C. S. Rim, H. Yao, M. S. Roberson, and P. J. S. Stork (1995) *J. Biol. Chem.* 270, 14587–14596.
69. Qui, M.-S., and S. H. Green (1991) *Neuron* 7, 937–946.
70. Roberson, M. S., A. Misra-Press, M. E. Laurance, P. J. S. Stork, and R. A. Maurer (1995) *Mol. Cell Biol.* 17, 3531–3539.
71. Rosen, L. B., D. D. Ginty, M. J. Weber, and M. E. Greenberg (1994) *Neuron* 12, 1207–1221.
72. Whitemarsh, A. J., P. Shore, A. D. Sharrocks, and R. J. Davis (1995) *Science* 269, 403–407.
73. Yao, H., K. Labudda, C. Rim, P. Capodieci, M. Loda, and P. J. S. Stork (1995) *J. Biol. Chem.* 270, 20748–20753.
74. Kyriakis, J. M., Banerjee, P., Nikolakaki, E., Dai, T., Rubie, E. A., Ahmad, M. F., Avruch, J. and Woodgett, J. R. (1994) *Nature* 369, 156.
75. Sluss, H. K., Barrett, T., Derijard, B. and Davis, R. J. (1994) *Mol. Cell. Biol.* 14, 8376–8384.
76. Cano, E. and Mahadevan, L. C. (1995) *TIBS* 20, 117–122.
77. Yao, R. and Cooper, G. (1995) *Science* 267, 2003–2007.
78. Milne, D. M., Campbell, L. E., Campbell, D. G., and Meek, D. W. (1995) *J. Biol. Chem.* 270, 5511–5518.
79. Liu, Y., Gorospe, M., Yang, C. and Halbrook, N. J. (1995) *J. Biol. Chem.* 270, 8377–8380.
80. Minden, A., Lin, A., McMahon, M., Lange-Carter, C., Derijard, B., Davis, R. J., Johnson, G. L., and Karin, M. (1994) *Science* 266, 1719–1723.
81. Derijard, B., Hibi, M., Wu, I. H., Barrett, T., Su, B., Deng, T., Karin, M. and Davis, R. J. (1994) *Cell* 76, 1025–1037.
82. Kallunki, T., Su, B., Tsigelny, I., Sluss, H. K., Derijard, B., Moore, G., Davis, R., and Karin, M. (1994) *Genes & Dev.* 8, 2996–3007.
83. Whitmarsh, A. J., Shore, P., Sharrocks, A. D. and Davis, R. J. (1995) *Science* 269, 403–407.
84. Thompson, C. B. (1995) *Science* 267, 1456–1462.
85. Kharbanda, S., Saleem, A., Shafman, T., Emoto, Y., Taneja, N., Rubin, E., Weichselbaum, R., Woodgett, J., Avruch, J., Kyriakis, J. and Kufe, D. (1995) *J. Biol. Chem.* 270, 18871–18874.
86, Kerr, J. F. R., Winterford, C. M. and Harmon, B. V. (1994) *Cancer* 73, 2013–2026.

---

We claim:

1. An isolated and purified rat MKP-2 protein.

2. The MKP-2 protein of claim 1, wherein the MKP-2 protein comprises the amino acid sequence set forth in SEQ ID No:5.

3. The MKP-2 protein of claim 1, wherein the MKP-2 protein consists of the amino acid sequence set forth in SEQ ID No:5.

* * * * *